US011696822B2

(12) United States Patent
Kubiak et al.

(10) Patent No.: US 11,696,822 B2
(45) Date of Patent: Jul. 11, 2023

(54) DEVICES, SYSTEMS, AND METHODS FOR REPAIRING SOFT TISSUE AND ATTACHING SOFT TISSUE TO BONE

(71) Applicant: CONEXTIONS, INC., Salt Lake City, UT (US)

(72) Inventors: Erik N. Kubiak, Las Vegas, NV (US); Roy M. Taylor, Salt Lake City, UT (US); Zackery K. Evans, Woods Cross, UT (US); Barrett J. Yates, Bountiful, UT (US); Daniel K. Smith, Woods Cross, UT (US); Cody L. Gehrke, South Jordan, UT (US)

(73) Assignee: CONEXTIONS, INC., Salt Lake City, UT (US)

( * ) Notice: Subject to any disclaimer, the term of this patent is extended or adjusted under 35 U.S.C. 154(b) by 0 days.

(21) Appl. No.: 16/226,573

(22) Filed: Dec. 19, 2018

(65) Prior Publication Data

US 2019/0209289 A1    Jul. 11, 2019

Related U.S. Application Data

(63) Continuation-in-part of application No. 15/907,202, filed on Feb. 27, 2018, which is a continuation-in-part
(Continued)

(51) Int. Cl.
*A61F 2/08* (2006.01)
*A61B 17/04* (2006.01)
(Continued)

(52) U.S. Cl.
CPC .......... *A61F 2/0811* (2013.01); *A61B 17/0401* (2013.01); *A61B 17/062* (2013.01);
(Continued)

(58) Field of Classification Search
CPC .......... A61F 2/08; A61B 17/04; A61B 17/064
See application file for complete search history.

(56) References Cited

U.S. PATENT DOCUMENTS

| 3,166,072 A | 1/1965 | Sullivan et al. |
| 4,388,926 A | 6/1983 | Shalaby et al. |

(Continued)

FOREIGN PATENT DOCUMENTS

| CN | 104023649 | 9/2014 |
| JP | 2006503655 | 2/2006 |

(Continued)

OTHER PUBLICATIONS

Office Action with English Translation issued in CN 201580066314.4 dated Jun. 22, 2018.
(Continued)

*Primary Examiner* — Matthew W Schall
(74) *Attorney, Agent, or Firm* — David L. Stott

(57) ABSTRACT

Devices, systems and/or methods for repairing soft tissue adjacent a soft tissue repair site. In one embodiment, the repair device includes an anchor member having a base with at least four legs extending from the base. The base extends with a generally flat circular profile defining an upper surface and an underside surface with a central opening extending therethrough. Further, the at least four legs extend from the base with an elongated angled portion, the elongated angled portion being oriented at an angle less than seventy-five degrees relative to the underside surface of the base. With this arrangement, the anchor member may be fixated to soft tissue by rotating the base with a delivery tool so that the elongated angled portion of the at least four legs facilitates the anchor member sinking into the soft tissue and fixating thereto.

18 Claims, 24 Drawing Sheets

Related U.S. Application Data of application No. 15/870,447, filed on Jan. 12, 2018, which is a continuation-in-part of application No. 15/719,346, filed on Sep. 28, 2017.

(60) Provisional application No. 62/633,000, filed on Feb. 20, 2018, provisional application No. 62/608,533, filed on Dec. 20, 2017, provisional application No. 62/581,031, filed on Nov. 2, 2017, provisional application No. 62/464,300, filed on Feb. 27, 2017, provisional application No. 62/445,596, filed on Jan. 12, 2017, provisional application No. 62/401,042, filed on Sep. 28, 2016.

(51) Int. Cl.
*A61B 17/064* (2006.01)
*A61B 17/062* (2006.01)
*A61B 17/068* (2006.01)
*A61B 17/06* (2006.01)
*A61B 17/00* (2006.01)
*A61B 17/10* (2006.01)

(52) U.S. Cl.
CPC ........ *A61B 17/068* (2013.01); *A61B 17/0642* (2013.01); *A61B 17/0643* (2013.01); *A61B 17/0686* (2013.01); *A61B 17/10* (2013.01); *A61B 2017/00473* (2013.01); *A61B 2017/0403* (2013.01); *A61B 2017/044* (2013.01); *A61B 2017/045* (2013.01); *A61B 2017/0409* (2013.01); *A61B 2017/0412* (2013.01); *A61B 2017/0414* (2013.01); *A61B 2017/0427* (2013.01); *A61B 2017/0437* (2013.01); *A61B 2017/0641* (2013.01); *A61B 2017/0647* (2013.01); *A61B 2017/06052* (2013.01); *A61F 2/0805* (2013.01); *A61F 2002/0823* (2013.01); *A61F 2002/0829* (2013.01); *A61F 2002/0864* (2013.01); *A61F 2002/0888* (2013.01); *A61F 2220/0016* (2013.01); *A61F 2220/0025* (2013.01)

(56) References Cited

U.S. PATENT DOCUMENTS

| | | |
|---|---|---|
| 4,414,967 A | 11/1983 | Shapiro |
| 4,454,875 A | 6/1984 | Pratt et al. |
| 4,461,298 A | 7/1984 | Shalaby et al. |
| 4,469,101 A | 9/1984 | Coleman et al. |
| 4,489,875 A | 12/1984 | Crawford et al. |
| 4,532,926 A | 8/1985 | O'Holla |
| 4,534,350 A | 8/1985 | Golden et al. |
| 4,548,202 A | 10/1985 | Duncan |
| 4,610,250 A | 9/1986 | Green |
| 4,655,222 A | 4/1987 | Florez et al. |
| 4,655,980 A | 4/1987 | Chu |
| 4,741,330 A | 5/1988 | Hayhurst |
| 4,776,890 A | 10/1988 | Chu |
| 4,796,612 A | 1/1989 | Reese |
| 4,810,549 A | 3/1989 | Abrams et al. |
| 4,873,976 A | 10/1989 | Schreiber |
| 4,942,875 A | 7/1990 | Hlavacek et al. |
| 4,946,467 A | 8/1990 | Ohi et al. |
| 4,960,420 A | 10/1990 | Goble et al. |
| 4,983,184 A | 1/1991 | Steinemann |
| 5,047,103 A | 9/1991 | Abrams et al. |
| 5,061,283 A | 10/1991 | Silvestrini |
| 5,163,956 A | 11/1992 | Liu et al. |
| 5,207,841 A | 5/1993 | Abrams |
| 5,209,756 A | 5/1993 | Seedhom et al. |
| 5,250,049 A | 10/1993 | Michael |
| 5,290,552 A | 3/1994 | Sierra et al. |
| 5,292,334 A | 3/1994 | Howansky |
| 5,306,290 A | 4/1994 | Martins et al. |
| 5,306,500 A | 4/1994 | Rhee et al. |
| 5,312,023 A | 5/1994 | Green et al. |
| 5,326,013 A | 7/1994 | Green et al. |
| 5,329,943 A | 7/1994 | Johnson |
| 5,342,376 A | 8/1994 | Ruff |
| 5,346,746 A | 9/1994 | Abrams |
| 5,370,662 A | 12/1994 | Stone et al. |
| 5,389,098 A | 2/1995 | Tsuruta et al. |
| 5,413,791 A | 5/1995 | Rhee et al. |
| 5,446,091 A | 8/1995 | Rhee et al. |
| 5,447,265 A | 9/1995 | Vidal et al. |
| 5,458,636 A | 10/1995 | Brancato |
| 5,465,894 A | 11/1995 | Clark et al. |
| 5,480,644 A | 1/1996 | Freed |
| 5,510,418 A | 4/1996 | Rhee et al. |
| 5,523,348 A | 6/1996 | Rhee et al. |
| 5,527,341 A | 6/1996 | Gogolewski et al. |
| 5,542,594 A | 8/1996 | McKean et al. |
| 5,556,428 A | 9/1996 | Shah |
| 5,575,803 A | 11/1996 | Cooper et al. |
| 5,580,923 A | 12/1996 | Yeung et al. |
| 55,973,637 | 1/1997 | Abrams et al. |
| 5,603,443 A | 2/1997 | Clark et al. |
| 5,607,094 A | 3/1997 | Clark et al. |
| 5,630,824 A | 5/1997 | Hart |
| 5,630,842 A | 5/1997 | Brodniewicz |
| 5,649,937 A | 7/1997 | Bito et al. |
| 5,665,112 A | 9/1997 | Thal |
| 5,667,839 A | 9/1997 | Berg |
| 5,706,997 A | 1/1998 | Green et al. |
| 5,711,472 A | 1/1998 | Bryan |
| 5,713,903 A | 2/1998 | Sander et al. |
| 5,716,981 A | 2/1998 | Hunter et al. |
| 5,723,008 A | 3/1998 | Gordon |
| 5,728,110 A | 3/1998 | Vidal et al. |
| 5,732,871 A | 3/1998 | Clark et al. |
| 5,756,678 A | 5/1998 | Shenoy et al. |
| 5,766,250 A | 6/1998 | Chervitz et al. |
| 5,785,713 A | 7/1998 | Jobe |
| 5,800,544 A | 9/1998 | Demopulos et al. |
| 5,807,581 A | 9/1998 | Rosenblatt et al. |
| 5,840,078 A | 11/1998 | Yerys |
| 5,858,156 A | 1/1999 | Abrams et al. |
| 5,860,229 A | 1/1999 | Morgenstern |
| 5,865,361 A | 2/1999 | Milliman et al. |
| 5,908,427 A | 6/1999 | McKean et al. |
| 5,916,224 A | 6/1999 | Esplin |
| 5,947,999 A | 9/1999 | Groiso |
| 5,961,520 A | 10/1999 | Beck, Jr. et al. |
| 5,964,774 A | 10/1999 | McKean et al. |
| 5,980,524 A | 11/1999 | Justin et al. |
| 5,997,811 A | 12/1999 | Esposito |
| 6,010,764 A | 1/2000 | Abrams |
| 6,013,083 A | 1/2000 | Bennett |
| 6,027,523 A | 2/2000 | Schmieding |
| 6,030,410 A | 2/2000 | Zurbrugg |
| 6,045,560 A | 4/2000 | McKean et al. |
| 6,079,606 A | 6/2000 | Milliman et al. |
| 6,080,192 A | 6/2000 | Demopulos et al. |
| 6,083,242 A | 7/2000 | Cook |
| 6,083,332 A | 7/2000 | Abrams |
| 6,086,547 A | 7/2000 | Hanssen et al. |
| 6,099,538 A | 8/2000 | Moses et al. |
| 6,106,556 A | 8/2000 | Demopulos et al. |
| 6,110,560 A | 8/2000 | Abrams |
| 6,111,165 A | 8/2000 | Berg |
| 6,206,886 B1 | 3/2001 | Bennett |
| 6,241,139 B1 | 6/2001 | Milliman et al. |
| 6,241,747 B1 | 6/2001 | Ruff |
| 6,250,532 B1 | 6/2001 | Green et al. |
| 6,277,394 B1 | 8/2001 | Sierra |
| 6,330,965 B1 | 12/2001 | Milliman et al. |
| 6,333,347 B1 | 12/2001 | Hunter et al. |
| 6,358,557 B1 | 3/2002 | Wang et al. |
| 6,383,199 B2 | 5/2002 | Carter et al. |
| 6,413,742 B1 | 7/2002 | Olsen et al. |
| D462,766 S | 9/2002 | Jacobs et al. |
| 6,464,706 B1 | 10/2002 | Winters |

(56) References Cited

U.S. PATENT DOCUMENTS

| | | |
|---|---|---|
| 6,472,171 B1 | 10/2002 | Toman et al. |
| 6,485,503 B2 | 11/2002 | Jacobs et al. |
| 6,491,714 B1 | 12/2002 | Bennett |
| 6,495,127 B1 | 12/2002 | Wallace et al. |
| 6,515,016 B2 | 2/2003 | Hunter |
| 6,517,579 B1 | 2/2003 | Paulos et al. |
| 6,533,802 B2 | 3/2003 | Bojarski et al. |
| 6,544,273 B1 | 4/2003 | Harari et al. |
| 6,551,315 B2 | 4/2003 | Kortenbach et al. |
| 6,569,186 B1 | 5/2003 | Winters et al. |
| 6,575,976 B2 | 6/2003 | Grafton |
| 6,644,532 B2 | 11/2003 | Green et al. |
| 6,645,226 B1 | 11/2003 | Jacobs et al. |
| 6,648,893 B2 | 11/2003 | Dudasik |
| 6,652,563 B2 | 11/2003 | Dreyfuss |
| 6,656,183 B2 | 12/2003 | Colleran et al. |
| 6,656,215 B1 | 12/2003 | Yanez et al. |
| 6,666,873 B1 | 12/2003 | Cassell |
| 6,669,073 B2 | 12/2003 | Milliman et al. |
| 6,689,803 B2 | 2/2004 | Hunter |
| 6,712,830 B2 | 3/2004 | Esplin |
| 6,716,226 B2 | 4/2004 | Sixto, Jr. et al. |
| 6,740,100 B2 | 5/2004 | Demopulos et al. |
| 6,743,233 B1 | 6/2004 | Baldwin et al. |
| 6,743,240 B2 | 6/2004 | Smith et al. |
| 6,773,450 B2 | 8/2004 | Leung et al. |
| 6,824,548 B2 | 11/2004 | Smith et al. |
| 6,830,174 B2 | 12/2004 | Hillstead et al. |
| 6,843,794 B2 | 1/2005 | Sixto, Jr. et al. |
| 6,877,647 B2 | 4/2005 | Green et al. |
| 6,893,452 B2 | 5/2005 | Jacobs |
| 6,905,513 B1 | 6/2005 | Metzger |
| 6,945,979 B2 | 9/2005 | Kortenbach et al. |
| 6,953,138 B1 | 10/2005 | Dworak et al. |
| 6,953,139 B2 | 10/2005 | Milliman et al. |
| 6,962,594 B1 | 11/2005 | Thevenet |
| 6,991,643 B2 | 1/2006 | Saadat |
| 7,016,194 B1 | 3/2006 | Wong |
| 7,056,331 B2 | 6/2006 | Kaplan et al. |
| 7,070,602 B2 | 7/2006 | Smith et al. |
| 7,074,203 B1 | 7/2006 | Johanson et al. |
| 7,090,685 B2 | 8/2006 | Kortenbach et al. |
| 7,121,446 B2 | 10/2006 | Arad et al. |
| 7,129,209 B2 | 10/2006 | Rhee |
| 7,156,862 B2 | 1/2007 | Jacobs et al. |
| 7,172,615 B2 | 2/2007 | Morriss et al. |
| 7,176,256 B2 | 2/2007 | Rhee et al. |
| 7,189,238 B2 | 3/2007 | Lombardo et al. |
| 7,226,468 B2 | 6/2007 | Ruff |
| 7,229,413 B2 | 6/2007 | Violante et al. |
| 7,232,445 B2 | 6/2007 | Kortenbach et al. |
| 7,275,674 B2 | 10/2007 | Racenet et al. |
| 7,296,724 B2 | 11/2007 | Green et al. |
| 7,303,107 B2 | 12/2007 | Milliman et al. |
| 7,303,577 B1 | 12/2007 | Dean |
| 7,309,346 B2 | 12/2007 | Martinek |
| 7,328,829 B2 | 2/2008 | Arad et al. |
| 7,343,920 B2 | 3/2008 | Toby et al. |
| 7,354,627 B2 | 4/2008 | Pedrozo et al. |
| 7,398,907 B2 | 7/2008 | Racenet et al. |
| 7,401,720 B1 | 7/2008 | Durrani |
| 7,438,209 B1 | 10/2008 | Hess et al. |
| 7,442,202 B2 | 10/2008 | Dreyfuss |
| 7,464,848 B2 | 12/2008 | Green et al. |
| 7,510,566 B2 | 3/2009 | Jacobs et al. |
| 7,530,484 B1 | 5/2009 | Durrani |
| 7,530,990 B2 | 5/2009 | Perriello et al. |
| 7,565,993 B2 | 7/2009 | Milliman et al. |
| 7,568,604 B2 | 8/2009 | Ehrenfels et al. |
| 7,600,663 B2 | 10/2009 | Green |
| 7,604,151 B2 | 10/2009 | Hess et al. |
| 7,611,038 B2 | 11/2009 | Racenet et al. |
| 7,611,521 B2 | 11/2009 | Lubbers et al. |
| 7,615,058 B2 | 11/2009 | Sixto, Jr. et al. |
| 7,624,487 B2 | 12/2009 | Trull et al. |
| 7,635,074 B2 | 12/2009 | Olson et al. |
| 7,635,367 B2 | 12/2009 | Groiso |
| 7,640,617 B2 | 1/2010 | Kennedy et al. |
| 7,641,091 B2 | 1/2010 | Olson et al. |
| 7,665,646 B2 | 2/2010 | Prommersberger |
| 7,708,759 B2 | 5/2010 | Lubbers et al. |
| 7,727,246 B2 | 6/2010 | Sixto, Jr. et al. |
| 7,727,248 B2 | 6/2010 | Smith et al. |
| 7,731,718 B2 | 6/2010 | Schwammberger et al. |
| 7,771,468 B2 | 8/2010 | Whitbourne et al. |
| 7,794,484 B2 | 9/2010 | Stone et al. |
| 7,819,896 B2 | 10/2010 | Racenet |
| 7,824,426 B2 | 11/2010 | Racenet et al. |
| 7,828,189 B2 | 11/2010 | Holsten et al. |
| 7,842,097 B2 | 11/2010 | Yamamoto et al. |
| 7,845,533 B2 | 12/2010 | Marczyk et al. |
| 7,861,907 B2 | 1/2011 | Green et al. |
| 7,887,551 B2 | 2/2011 | Bojarski et al. |
| 7,891,531 B1 | 2/2011 | Ward |
| 7,909,224 B2 | 3/2011 | Prommersberger |
| 7,926,692 B2 | 4/2011 | Racenet et al. |
| 7,942,304 B2 | 5/2011 | Taylor et al. |
| 7,942,885 B2 | 5/2011 | Sixto, Jr. et al. |
| 7,950,561 B2 | 5/2011 | Aranyi |
| 8,006,700 B2 | 8/2011 | Demopulos et al. |
| 8,008,598 B2 | 8/2011 | Whitman et al. |
| 8,011,550 B2 | 9/2011 | Aranyi et al. |
| 8,016,177 B2 | 9/2011 | Bettuchi et al. |
| 8,016,178 B2 | 9/2011 | Olson et al. |
| 8,021,378 B2 | 9/2011 | Sixto, Jr. et al. |
| 8,029,563 B2 | 10/2011 | House et al. |
| 8,033,439 B2 | 10/2011 | Racenet et al. |
| 8,038,045 B2 | 10/2011 | Bettuchi et al. |
| 8,043,328 B2 | 10/2011 | Hahnen et al. |
| 8,057,524 B2 | 11/2011 | Meridew |
| 8,062,314 B2 | 11/2011 | Sixto, Jr. et al. |
| 8,062,330 B2 | 11/2011 | Prommersberger et al. |
| 8,062,363 B2 | 11/2011 | Hirpara et al. |
| 8,066,721 B2 | 11/2011 | Kortenbach et al. |
| 8,070,033 B2 | 12/2011 | Milliman et al. |
| 8,083,118 B2 | 12/2011 | Milliman et al. |
| 8,083,119 B2 | 12/2011 | Prommersberger |
| 8,083,120 B2 | 12/2011 | Shelton, IV et al. |
| 8,087,563 B2 | 1/2012 | Milliman |
| 8,113,409 B2 | 2/2012 | Cohen et al. |
| 8,114,129 B2 | 2/2012 | Lubbers et al. |
| 8,118,834 B1 | 2/2012 | Goraltchouk et al. |
| 8,123,101 B2 | 2/2012 | Racenet al. |
| 8,141,762 B2 | 3/2012 | Bedi et al. |
| 8,157,151 B2 | 4/2012 | Ingmanson et al. |
| 8,186,557 B2 | 5/2012 | Cohen et al. |
| 8,186,560 B2 | 5/2012 | Hess et al. |
| 8,205,620 B2 | 6/2012 | Taylor et al. |
| 8,210,414 B2 | 7/2012 | Bettuchi et al. |
| 8,210,416 B2 | 7/2012 | Milliman et al. |
| 8,256,654 B2 | 9/2012 | Bettuchi et al. |
| 8,256,656 B2 | 9/2012 | Milliman et al. |
| 8,292,152 B2 | 10/2012 | Milliman et al. |
| 8,298,286 B2 | 10/2012 | Trieu |
| 8,308,041 B2 | 11/2012 | Kostrzewski |
| 8,308,042 B2 | 11/2012 | Aranyi |
| 8,308,046 B2 | 11/2012 | Prommersberger |
| 8,322,455 B2 | 12/2012 | Shelton, IV et al. |
| 8,328,061 B2 | 12/2012 | Kasvikis |
| 8,342,377 B2 | 1/2013 | Milliman et al. |
| 8,343,186 B2 | 1/2013 | Dreyfuss et al. |
| 8,348,129 B2 | 1/2013 | Bedi et al. |
| 8,439,936 B2 | 5/2013 | McClellan |
| 8,453,905 B2 | 6/2013 | Holcomb et al. |
| 8,453,910 B2 | 6/2013 | Bettuchi et al. |
| 8,464,925 B2 | 6/2013 | Hull et al. |
| 8,469,252 B2 | 6/2013 | Holcomb et al. |
| 8,480,692 B2 | 7/2013 | McClellan |
| 8,485,412 B2 | 7/2013 | Shelton, IV et al. |
| 8,491,600 B2 | 7/2013 | McDevitt et al. |
| 8,500,776 B2 | 8/2013 | Ebner |
| 8,518,091 B2 | 8/2013 | McDevitt et al. |
| 8,540,131 B2 | 9/2013 | Swayze |
| 8,550,325 B2 | 10/2013 | Cohen et al. |

(56) References Cited

U.S. PATENT DOCUMENTS

| | | |
|---|---|---|
| 8,574,275 B2 | 11/2013 | Stone et al. |
| 8,585,721 B2 | 11/2013 | Kirsch |
| 8,602,286 B2 | 12/2013 | Crainich et al. |
| 8,608,765 B1 | 12/2013 | Jurbala |
| 8,613,384 B2 | 12/2013 | Pastorelli et al. |
| 8,616,430 B2 | 12/2013 | Stopek |
| 8,623,052 B2 | 1/2014 | Dreyfuss et al. |
| 8,636,766 B2 | 1/2014 | Milliman et al. |
| 8,668,130 B2 | 3/2014 | Hess et al. |
| 8,684,249 B2 | 4/2014 | Racenet et al. |
| 8,720,766 B2 | 5/2014 | Hess et al. |
| 8,740,034 B2 | 6/2014 | Morgan et al. |
| 8,801,732 B2 | 8/2014 | Harris et al. |
| 8,801,755 B2 | 8/2014 | Dreyfuss et al. |
| 8,814,904 B2 | 8/2014 | Bennett |
| 8,834,543 B2 | 9/2014 | McDevitt et al. |
| 8,840,003 B2 | 9/2014 | Morgan et al. |
| 8,845,686 B2 | 9/2014 | Bennett |
| 8,905,287 B2 | 12/2014 | Racenet et al. |
| 8,939,983 B2 | 1/2015 | Stone et al. |
| 9,204,960 B2 | 12/2015 | Albertorio et al. |
| 9,277,909 B2 | 3/2016 | Brunsvold |
| 9,307,979 B1 | 4/2016 | Bennett et al. |
| 9,427,309 B2 | 8/2016 | Kubiak et al. |
| 9,439,645 B2 | 9/2016 | Stone et al. |
| 9,451,961 B2 | 9/2016 | Kubiak |
| 9,486,207 B2 | 11/2016 | Dooney, Jr. et al. |
| 9,642,610 B2 | 5/2017 | Albertorio et al. |
| 9,655,625 B2 | 5/2017 | Kubiak et al. |
| 9,700,305 B2 | 7/2017 | Bennett et al. |
| 10,219,804 B2 | 3/2019 | Linder et al. |
| 10,299,842 B2 | 5/2019 | Hollis et al. |
| 10,835,241 B2 | 11/2020 | Kubiak et al. |
| 2001/0044637 A1 | 11/2001 | Jacobs et al. |
| 2001/0051815 A1 | 12/2001 | Esplin |
| 2002/0013298 A1 | 1/2002 | Hunter |
| 2002/0022861 A1 | 2/2002 | Jacobs et al. |
| 2002/0055666 A1 | 5/2002 | Hunter et al. |
| 2002/0077661 A1 | 6/2002 | Saadat |
| 2002/0123750 A1 | 9/2002 | Eisermann et al. |
| 2002/0173807 A1 | 11/2002 | Jacobs |
| 2002/0192280 A1 | 12/2002 | Hunter et al. |
| 2003/0065360 A1 | 4/2003 | Jacobs et al. |
| 2003/0069602 A1 | 4/2003 | Jacobs et al. |
| 2003/0105489 A1 | 6/2003 | Eichhorn et al. |
| 2003/0120309 A1 | 6/2003 | Colleran et al. |
| 2003/0130694 A1 | 7/2003 | Bojarski et al. |
| 2003/0130735 A1 | 7/2003 | Rogalski |
| 2003/0153972 A1 | 8/2003 | Helmus |
| 2003/0157170 A1 | 8/2003 | Liggins et al. |
| 2003/0181371 A1 | 9/2003 | Hunter et al. |
| 2003/0203976 A1 | 10/2003 | Hunter et al. |
| 2004/0006352 A1 | 1/2004 | Nobles et al. |
| 2004/0010276 A1 | 1/2004 | Jacobs et al. |
| 2004/0039404 A1 | 2/2004 | Dreyfuss |
| 2004/0059336 A1 | 3/2004 | Lombardo et al. |
| 2004/0060410 A1 | 4/2004 | Leung et al. |
| 2004/0076672 A1 | 4/2004 | Hunter et al. |
| 2004/0088003 A1 | 5/2004 | Leung et al. |
| 2004/0153153 A1 | 8/2004 | Elson et al. |
| 2004/0193217 A1 | 9/2004 | Lubbers et al. |
| 2004/0199241 A1 | 10/2004 | Gravett et al. |
| 2004/0219214 A1 | 11/2004 | Gravett et al. |
| 2004/0220591 A1 | 11/2004 | Bonutti |
| 2004/0220616 A1 | 11/2004 | Bonutti et al. |
| 2004/0224023 A1 | 11/2004 | Hunter et al. |
| 2004/0254609 A1 | 12/2004 | Esplin |
| 2004/0260340 A1 | 12/2004 | Jacobs et al. |
| 2004/0267362 A1 | 12/2004 | Hwang et al. |
| 2005/0090827 A1 | 4/2005 | Gedebou |
| 2005/0152941 A1 | 7/2005 | Hunter et al. |
| 2005/0175665 A1 | 8/2005 | Hunter et al. |
| 2005/0186261 A1 | 8/2005 | Avelar et al. |
| 2005/0192428 A1 | 9/2005 | Berg et al. |
| 2005/0197699 A1 | 9/2005 | Jacobs et al. |
| 2006/0127445 A1 | 6/2006 | Hunter et al. |
| 2006/0135994 A1 | 6/2006 | Ruff et al. |
| 2006/0147332 A1 | 7/2006 | Jones |
| 2006/0149349 A1 | 7/2006 | Garbe |
| 2006/0240064 A9 | 10/2006 | Hunter et al. |
| 2006/0240113 A1 | 10/2006 | Hunter et al. |
| 2006/0247641 A1 | 11/2006 | Re et al. |
| 2007/0021779 A1 | 1/2007 | Garvin et al. |
| 2007/0026043 A1 | 2/2007 | Guan et al. |
| 2007/0027527 A1 | 2/2007 | Williams et al. |
| 2007/0065663 A1 | 3/2007 | Trull et al. |
| 2007/0123984 A1 | 5/2007 | Hodorek |
| 2007/0156158 A1 | 7/2007 | Herzberg et al. |
| 2007/0162022 A1 | 7/2007 | Zhang et al. |
| 2007/0196421 A1 | 8/2007 | Hunter et al. |
| 2007/0208355 A1 | 9/2007 | Ruff |
| 2007/0208377 A1 | 9/2007 | Kaplan et al. |
| 2008/0003394 A1 | 1/2008 | Eke |
| 2008/0027443 A1 | 1/2008 | Lambert |
| 2008/0027445 A1 | 1/2008 | Brown, Jr. et al. |
| 2008/0027446 A1 | 1/2008 | Stone et al. |
| 2008/0027486 A1 | 1/2008 | Jones et al. |
| 2008/0051888 A1 | 2/2008 | Ratcliffe et al. |
| 2008/0058579 A1 | 3/2008 | Hunter et al. |
| 2008/0124400 A1 | 5/2008 | Liggins et al. |
| 2008/0195204 A1 | 8/2008 | Zhukauskas et al. |
| 2008/0234731 A1 | 9/2008 | Leung et al. |
| 2008/0247987 A1 | 10/2008 | Liggins et al. |
| 2008/0281325 A1 | 11/2008 | Stone et al. |
| 2008/0312315 A1 | 12/2008 | Daniloff et al. |
| 2009/0012560 A1 | 1/2009 | Hunter et al. |
| 2009/0018577 A1 | 1/2009 | Leung et al. |
| 2009/0020584 A1 | 1/2009 | Soltz et al. |
| 2009/0048537 A1 | 2/2009 | Lydon et al. |
| 2009/0048616 A1 | 2/2009 | Gonzalez-Hernandez |
| 2009/0060973 A1 | 3/2009 | Hunter et al. |
| 2009/0107965 A1 | 4/2009 | D'Agostino |
| 2009/0112259 A1 | 4/2009 | D'Agostino |
| 2009/0117070 A1 | 5/2009 | Daniloff et al. |
| 2009/0125094 A1 | 5/2009 | Rust |
| 2009/0143819 A1 | 6/2009 | D'Agostino |
| 2009/0149884 A1 | 6/2009 | Snyder et al. |
| 2009/0156980 A1 | 6/2009 | Eaton et al. |
| 2009/0216326 A1 | 8/2009 | Hirpara et al. |
| 2009/0222039 A1 | 9/2009 | Dreyfuss et al. |
| 2009/0226500 A1 | 9/2009 | Avelar et al. |
| 2009/0228021 A1 | 9/2009 | Leung |
| 2009/0234386 A1 | 9/2009 | Dean et al. |
| 2009/0280153 A1 | 11/2009 | Hunter et al. |
| 2009/0299386 A1* | 12/2009 | Meridew ............... A61F 2/0811 606/151 |
| 2009/0324720 A1 | 12/2009 | He et al. |
| 2010/0016872 A1 | 1/2010 | Bayton et al. |
| 2010/0023052 A1 | 1/2010 | Heinrich et al. |
| 2010/0160718 A1 | 6/2010 | Villafana et al. |
| 2010/0193568 A1 | 8/2010 | Scheib et al. |
| 2010/0198258 A1 | 8/2010 | Heaven et al. |
| 2010/0217314 A1 | 8/2010 | Holsten et al. |
| 2010/0228078 A1 | 9/2010 | Sater |
| 2010/0249802 A1 | 9/2010 | May et al. |
| 2010/0324676 A1 | 12/2010 | Albertorio et al. |
| 2011/0106253 A1 | 5/2011 | Barwood et al. |
| 2011/0124956 A1 | 5/2011 | Mujwid |
| 2011/0125287 A1 | 5/2011 | Hotter et al. |
| 2011/0155787 A1 | 6/2011 | Baxter, III et al. |
| 2011/0288565 A1 | 11/2011 | Kubiak et al. |
| 2011/0288566 A1 | 11/2011 | Kubiak |
| 2011/0301706 A1 | 12/2011 | Brooks et al. |
| 2012/0080336 A1 | 4/2012 | Shelton, IV et al. |
| 2012/0130374 A1 | 5/2012 | Bouduban et al. |
| 2012/0203253 A1 | 8/2012 | Kubiak |
| 2012/0245629 A1 | 9/2012 | Gross et al. |
| 2013/0131781 A1 | 5/2013 | Greenhalgh et al. |
| 2013/0144310 A1 | 6/2013 | Gordon et al. |
| 2013/0197580 A1 | 8/2013 | Perriello et al. |
| 2014/0039551 A1 | 2/2014 | Donahue |
| 2014/0067061 A1 | 3/2014 | Kubiak et al. |
| 2014/0214037 A1* | 7/2014 | Mayer .................. A61B 17/68 606/75 |

(56) References Cited

U.S. PATENT DOCUMENTS

| | | | |
|---|---|---|---|
| 2015/0245841 A1 | 9/2015 | Linder et al. |
| 2015/0272567 A1 | 10/2015 | Feezor et al. |
| 2015/0289866 A1 | 10/2015 | Bowen et al. |
| 2016/0066900 A1 | 3/2016 | Brunsvold et al. |
| 2016/0066907 A1 | 3/2016 | Cheney et al. |
| 2016/0100835 A1 | 4/2016 | Linder et al. |
| 2016/0100933 A1 | 4/2016 | Linder et al. |
| 2016/0174965 A1 | 6/2016 | Brunsvold |
| 2016/0242771 A1 | 8/2016 | Weinstein et al. |
| 2017/0027578 A1 | 2/2017 | Friedman et al. |
| 2017/0056158 A1 | 3/2017 | Saing |
| 2017/0156847 A1 | 6/2017 | Ricci et al. |
| 2017/0333026 A1 | 11/2017 | Dreyfuss et al. |
| 2018/0078253 A1 | 3/2018 | Kubiak et al. |
| 2018/0200042 A1 | 7/2018 | Kubiak et al. |
| 2021/0100545 A1 | 4/2021 | Thies |

FOREIGN PATENT DOCUMENTS

| | | |
|---|---|---|
| WO | WO2004037094 | 5/2004 |
| WO | WO2016061530 | 4/2016 |
| WO | WO2016138033 | 9/2016 |
| WO | WO2019164853 | 8/2019 |

OTHER PUBLICATIONS

Supplementary European Search Report issued in EP 15850646.9 dated Jun. 25, 2018.

International Search Report dated Feb. 26, 2016 for International Application No. PCT/US2015/56059 (14 pages).

International Search Report dated Jul. 20, 2015 for International Application No. PCT/US2015/020231 (10 pages).

International Search Report dated Oct. 10, 2013 for International Application No. PCT/US2013/052735 (7 pages).

McKenzie, "An Experimental Multiple Barbed Suture For The Long Flexor Tendons Of The Palm And Fingers," Journal of Bone and Joint Surgery, Aug. 1967, pp. 440-447, vol. 49 B, No. 3.

Momose et al., "Suture Techniques With High Breaking Strength And Low Gliding Resistance: Experiments In The Dog Flexor Digitorum Pofundus Tendon," Acta Orthop Scand, 2001, 72(6):635-641.

Leung et al., "Barbed, Bi-Directional Medical Sutures: Biomechanical Properties And Wound Closure Efficacy Study," Society for Biomaterials 28ths Annual Meeting Transactions, 2002, p. 724.

Chunfeng et al., "Enhancing The Strength Of The Tendon-Suture Interface Using 1-Ethyl-3-(3-dimethylaminoproply) Carbodimide Hydrochloride And Cyanoacrylate," Journal of Hand Surger, 2007, 32(5): 606-11.

Burkhead et al., "Use Of Graft Jacket As An Augmentation For Massive Rotator Cuff Tears," Semin Arthro, 2007, 18(1): 11-18.

Hirpara et al., "A Barbed Device For Digital Flexor Tendon Repair," http://proceedings.jbjs.org.uk/cgi/content/abstract/92-B/SUPP_II/291-d, Mar. 2010.

Office Action issued in EP 15850646.9 dated Sep. 19, 2019.

International Search Report dated May 8, 2019 for International Application No. PCT/US2019/018628 (14 pages).

Supplementary European Search Report dated Oct. 20, 2021 for European App. No. 19756761 (10 pages).

Office Action with English Translation in Japanese App. No. 2020-566536 dated Nov. 29, 2022 (7 pages).

Office Action in Chinese App. No. 201980014553.3 dated Feb. 10, 2023 (9 pages).

* cited by examiner

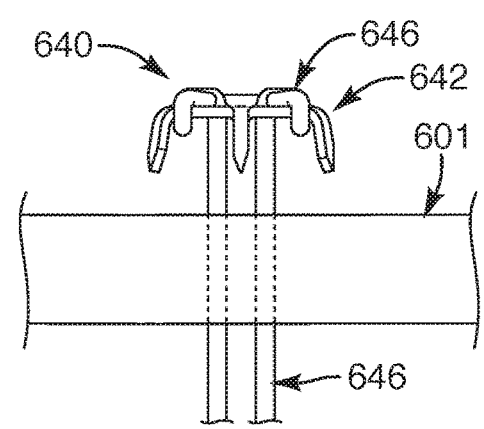
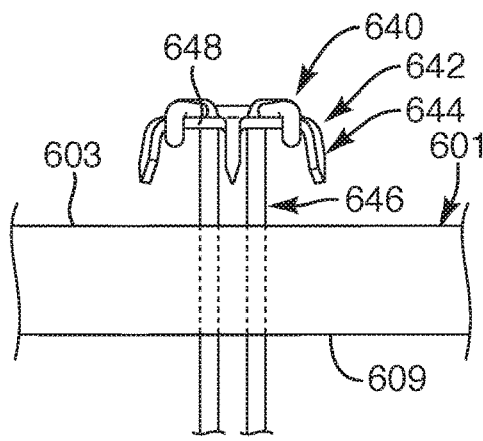
FIG. 42
FIG. 43
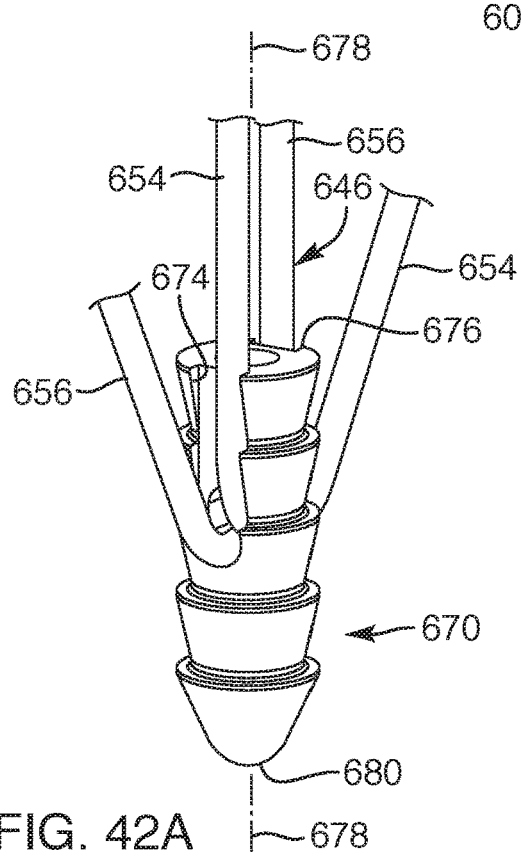
FIG. 42A

DEVICES, SYSTEMS, AND METHODS FOR REPAIRING SOFT TISSUE AND ATTACHING SOFT TISSUE TO BONE

CROSS-REFERENCE TO RELATED APPLICATIONS

The present application claims the benefit of U.S. Provisional Application No. 62/608,533, filed Dec. 20, 2017, and U.S. Provisional Application No. 62/633,000, filed Feb. 20, 2018, the disclosures of each are hereby incorporated by reference in their entirety. Further, the present application is a continuation-in-part of U.S. application Ser. No. 15/907,202, filed Feb. 27, 2018, which claims the benefit of U.S. Provisional Application No. 62/464,300, filed Feb. 27, 2017, U.S. Provisional Application No. 62/608,533, filed Dec. 20, 2017, and U.S. Provisional Application No. 62/633,000, filed Feb. 20, 2018, the disclosures of each are hereby incorporated by reference in their entirety. Further, U.S. patent application Ser. No. 15/907,202 also claims the benefit, and is a continuation-in-part of, U.S. patent application Ser. No. 15/870,447, filed Jan. 12, 2018, which claims the benefit of U.S. Provisional Application No. 62/581,031, filed Nov. 2, 2017, U.S. Provisional Application No. 62/464,300, filed Feb. 27, 2017, and U.S. Provisional Application No. 62/445,596, filed Jan. 12, 2017, the disclosures of each are hereby incorporated by reference herein in their entirety. Further, U.S. patent application Ser. No. 15/870,447 also claims the benefit, and is a continuation-in-part of, U.S. patent application Ser. No. 15/719,346, filed Sep. 28, 2017, which claims the benefit of U.S. Provisional Application No. 62/401,042, filed Sep. 28, 2016, the disclosures of which are hereby incorporated by reference herein in their entirety.

TECHNICAL FIELD

The present invention relates generally to soft tissue repair sites. More particularly, the present invention relates to devices, systems, and methods for repairing soft tissue and attaching soft tissue to bone.

BACKGROUND

One of the most common needs in orthopedic surgery is the fixation of soft tissue, such as ligament or tendon, to bone. Typically, fixating soft tissue to bone is implemented with a bone anchor and suture material with suture coupled between the soft tissue and the bone anchor such that the soft tissue is cinched in against the bone. However, coupling suture to soft tissue is time consuming and often requires complex suture patterns for effective fixation, often requiring specialized surgeons. While this can provide a good initial repair, the strength and quality of the repair may quickly degrade with subsequent loading and mobilization, depending on the activity level of the patient, which often results. As such, it would be advantageous to eliminate the complexity and the time consuming nature of this type of surgery while also increasing the long term effectiveness of the procedure.

BRIEF SUMMARY OF THE INVENTION

Embodiments of the present invention are directed to various devices, systems and methods for repairing soft tissue at a soft tissue repair site. For example, in some embodiments, such repair devices may be sized and configured to directly or indirectly couple to a bone anchor. In one embodiment, the repair device includes an anchor member configured to fixate to soft tissue. The anchor member includes a base with at least four legs extending from the base. The base extends with an upper side and an underside defining an outer periphery therebetween such that the upper side and the underside define a central opening therein. The at least four legs each extend from the outer periphery and extend downward in a maintained fixed orientation.

In one embodiment, the repair device further includes a flexible member wrapped over the base so as to couple to the base and extend along the central opening of the base. In another embodiment, the flexible member includes one or more filaments, the one or more filaments being wrapped around portions of the base. In still another embodiment, the flexible member includes one or more sutures coupled to the base with portions of the flexible member extending downward from the base.

In another embodiment, the at least four legs include one or more barbs extending therefrom. In another embodiment, the at least four legs extend downward from the base with an angled portion such that the angled portion extends at an angle that is less than seventy-five degrees relative to the underside of the anchor member. In still another embodiment, the at least four legs extend downward from the base with an angled portion such that the angled portion extends at an angle that is within the range of about twenty-five degrees and sixty-five degrees relative to the underside of the anchor member. In yet another embodiment, the at least four legs extend radially from the outer periphery of the base and then extend straight downward generally at a right angle relative to the underside of the base.

In accordance with another embodiment of the present invention, a repair device for fixating to soft tissue at a soft tissue repair site is provided. The repair device includes an anchor member having a base with at least four legs extending from the base. The base extends with a generally flat circular profile defining an upper surface and an underside surface with a central opening extending therethrough. The at least four legs extends from the base with an elongated angled portion, the elongated angled portion being oriented at an angle less than seventy-five degrees relative to the underside surface of the base.

In one embodiment, the repair device further includes a flexible member wrapped over the base so as to couple to the base and extend along the central opening of the base. In another embodiment, the flexible member includes one or more sutures. In yet another embodiment, the flexible member includes one or more filaments, the flexible member extending across portions of the central opening defined in the base. In still another embodiment, the repair device further includes a flexible element, the flexible element being elongated and configured to be coupled to the flexible member.

In another embodiment, the angle of the elongated angled portion of the at least four legs extends within the range of about twenty-five degrees and about sixty-five degrees relative to the underside of the anchor member. In another embodiment, the at least four legs extends radially from an outer periphery of the base and then extends downward to the elongated angled portion. In still another embodiment, the at least four legs include one or more barbs extending therefrom. In another embodiment, the at least four legs extend downward from the base in a maintained fixed orientation.

In accordance with another embodiment of the present invention, a method for fixating to soft tissue at a soft tissue repair site is provided. The method includes the steps of:

providing an anchor member with a base and at least four legs integrally extending from the base, the at least four legs extending from the base with an angled portion, the angled portion being oriented at an angle less than seventy-five degrees relative to the underside surface of the base; and sinking the at least four legs of the anchor member into soft tissue with rotation of the base of the anchor member.

In another embodiment, the method step of providing includes providing the anchor member with a flexible member wrapped over the base of the anchor member such that the flexible member extends over portions of a central opening defined in the base of the anchor member. In another embodiment, the method further includes the step of coupling the anchor member to a bone anchor positioned in bone with the soft tissue sandwiched therebetween such that the anchor member and soft tissue is synched adjacent the bone anchor with a flexible element coupled between the anchor member and the bone anchor.

In accordance with another embodiment of the present invention, a repair device for fixating to soft tissue at a soft tissue repair site is provided. The repair device includes an anchor member and a flexible member. The anchor member includes a base with multiple legs extending from an outer periphery of the base, the base extending with a central opening defined therein. The flexible member is wrapped over the base of the anchor member to act as coupling structure for the repair device.

BRIEF DESCRIPTION OF THE SEVERAL VIEWS OF THE DRAWINGS

The foregoing and other advantages of the invention will become apparent upon reading the following detailed description and upon reference to the drawings in which:

FIG. 42 is a side view of the repair device and a bone anchor, depicting portions of the flexible member extending from the repair device and through the bone anchor, according to another embodiment of the present invention;

FIG. 42A is a perspective view of the flexible member engaged with the bone anchor, according to another embodiment of the present invention;

FIG. 43 is a side view of the repair device and the bone anchor with the flexible member extending therebetween, depicting the bone anchor partially anchored within bone, according to another embodiment of the present invention;

DETAILED DESCRIPTION OF THE INVENTION

Various embodiments are disclosed herein of a soft tissue repair device and system. Such repair device and system may be sized and configured to approximate and fuse, for example, soft tissue to bone. The various embodiments may provide structure that maintains the soft tissue against bone in an abutting relationship, without gapping. In this manner, the repair device and system of the present invention may provide the proper healing required for fusing the soft tissue to bone.

Figure 1:
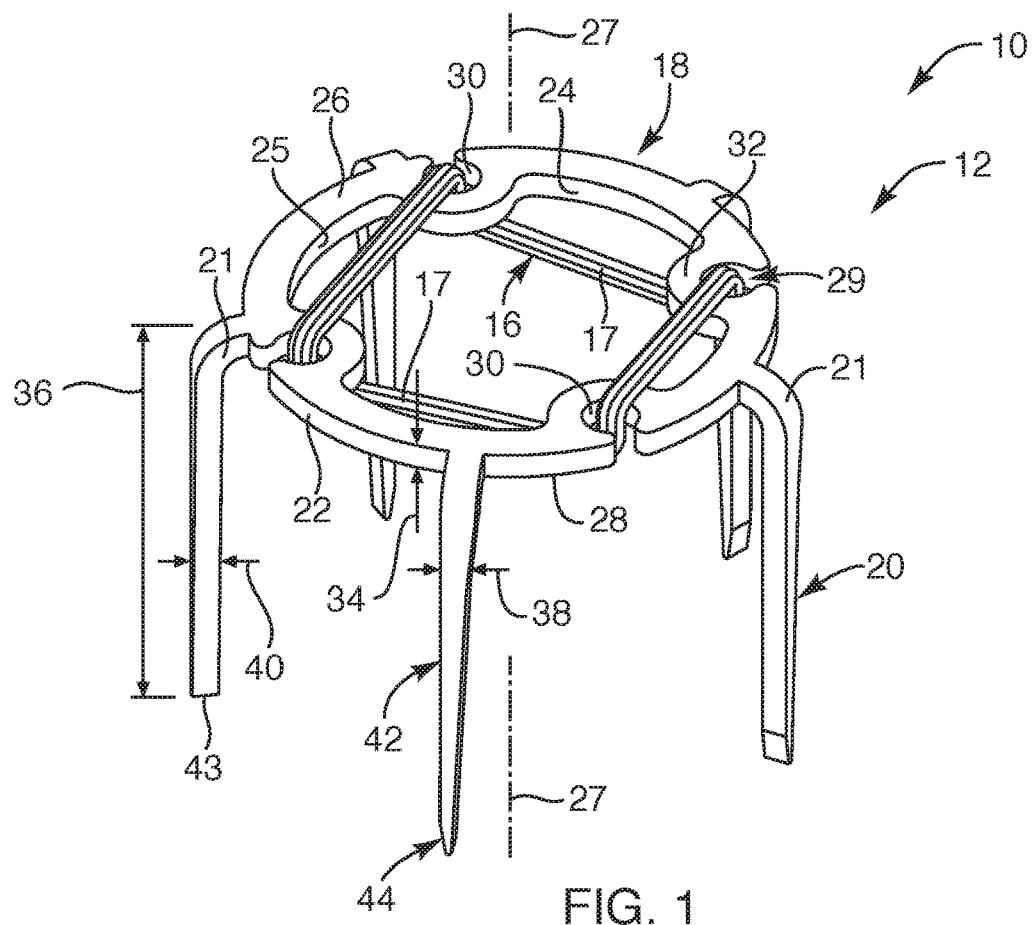
FIG. 1 is a perspective view of an anchor member of a repair device, depicting the anchor member having one or more flexible members attached thereto, according to an embodiment of the present invention.
Figure 2:
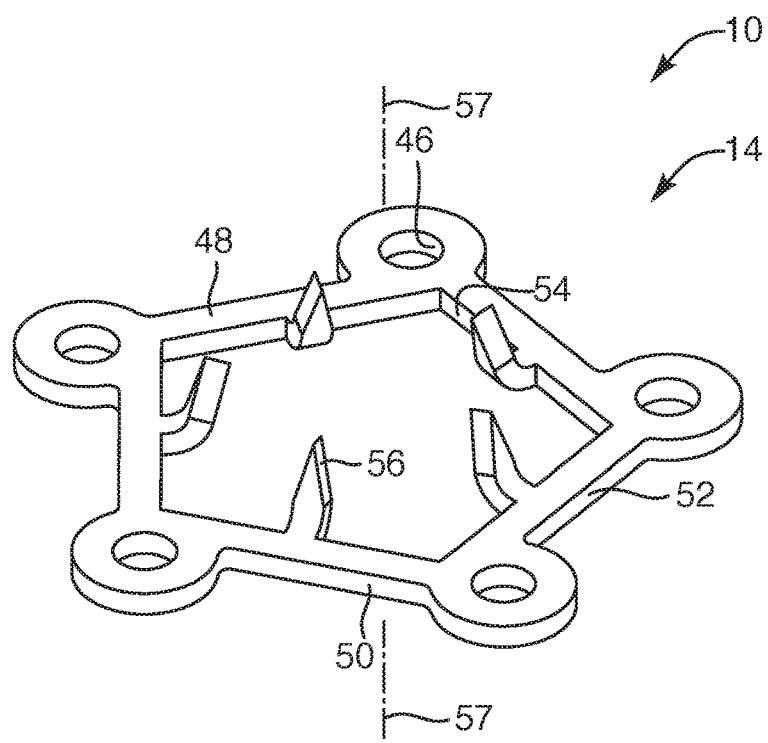
FIG. 2 is a perspective view of a capture member of the repair device for coupling to the anchor member of FIG. 1, according to another embodiment of the present invention.

Now with reference to FIGS. 1 and 2, one embodiment of a repair device 10 that may include an anchor member 12 and a capture member 14 is provided. The anchor member 12 may be sized and configured to cooperate with the capture member 14 for coupling to soft tissue, such as tendon or ligament type soft tissue. Such repair device 10 may include one or more flexible members 16 that may be coupled thereto for coupling to, for example, a bone anchor 152 (FIG. 12) with the soft tissue held against the bone and over or adjacent the bone anchor 152. Further, the repair device 10 may be deployed from a delivery device 11 (FIG. 8) so that the repair device may be fixated to soft tissue.

With respect to FIG. 1, the anchor member 12 of this embodiment may include one or more flexible members 16, such as a first flexible member 17, that may be coupled to the anchor member 12. Further, the anchor member 12 may include a base 18 with legs 20 extending downward from the base 18. The base 18 may include a circular structure or profile, such as a ring like structure, or any other suitable structure sized and configured to couple the one or more flexible members 16 thereto and having the legs 20 extending therefrom. The base 18 may include an outer periphery 22 and an inner periphery 24 such that the legs 20 may extend from the outer periphery 22. In another embodiment, the legs 20 may extend from the inner periphery 24. Further, the base 18 may define an upper surface 26 and a lower surface 28 extending to the outer periphery 22 and the inner periphery 24 of the base 18. The base 18 may define a tissue anchor axis 27 extending centrally and axially relative to the base 18 and extending substantially parallel relative to the legs 20. Further, in another embodiment, the legs 20 may extend from the outer periphery 22 with a curvature or curved portion 21 to then continue extending away from the base 18 in a substantially linear or straight manner so that the legs 20 may extend substantially perpendicular relative to the lower surface 28 or underside of the base 18.

In one embodiment, the base 18 may include coupling structure 29 for coupling the one or more flexible members 16 to the base 18. Such coupling structure 29 may include recesses, notches, protrusions, and/or openings formed in the base 18. The coupling structure 29 of the anchor member 12 may also include a portion of the legs 20, such as the curved portion 21 of the legs 20 or leg portions adjacent the base 18. In this manner, the legs 20 may be employed, at least in part, as the coupling structure 29. For example, the coupling structure 29 formed in the base 18 may include multiple recesses 30 defined in the base, the recesses 30 sized and configured to facilitate wrapping the first flexible member 17 to the base 18 of the anchor member 12. Such recesses 30 may be defined in the outer periphery 22 of the base 18 and may extend between the upper surface 26 and the lower surface 28 of the base 18. The inner periphery 24 of the base 18 may extend with bumps 32 or protrusions that correspond with the recesses 30 defined in the base 18.

The one or more flexible members 16 may be formed from one or more filaments or fibers. The filaments or fibers may be formed from a polymeric material or a natural fiber. In one embodiment, the filaments or fibers may be a polyethylene material, such as ultra-high-molecular-weight polyethylene ("UHMWPE"), a polyester material, a polypropylene material, or the like. In another embodiment, the one or more flexible members 16 may be formed of suture material and/or extend as a suture. In another embodiment, the polymeric filament or fiber may be a bioresorbable material, such as polylactide ("PLA"), polycaprolactone ("PCL"), polydioxanone ("PDX"), or the like, or any other suitable bioresorbable material as known to one of ordinary skill in the art. In another embodiment, the filaments or fibers may be formed in a woven or braided configuration or may extend with strands wound in a side-by-side configuration, or may extend with strands wound side-by-side and in a twisted configuration or any other suitable configuration to form a flexible member. In another embodiment, the one or more flexible members 16 may be a continuous loop. In another embodiment, the continuous loop may include a woven or braided structure. In another embodiment, the one or more flexible members 16 may extend with at least two free ends.

The anchor member 12 may be laser cut from sheet material or cut from the sheet material with any other suitable process. As such, the anchor member 12 may be a monolithic structure or a seamless unitary structure. The base 18 may include an outer diameter and an inner diameter, the outer diameter defined by the outer periphery 22 and the inner diameter defined by the inner periphery 24. The inner periphery 24 of the base 18 may define a central opening 25 of the base 18. In one embodiment, the tissue anchor axis 27 may be centrally located so that the tissue anchor axis 27 extends axially through the central opening 25. The base 18 may also define a thickness 34 similar to the thickness of the sheet material. As such, the base 18 may extend with a substantially flat structure or configuration with the upper surface 26 and the lower surface 28 being substantially planar. The outer periphery 22 and inner periphery 24 of the base 18 may extend radially relative to the tissue anchor axis 27 (or about the axis 27) along a majority of the outer and inner peripheries 22, 24 such that the outer and inner peripheries exhibit a generally circular profile (as viewed from the top or bottom of the anchor member 12). Further, the legs 20 may include a length 36, a width 38, and a depth 40, the depth being similar to the thickness of the base 18, which also may correspond with the thickness of the sheet material. The width 38 may include multiple tapers along the longitudinal length 36 of the legs 20. For example, the width 38 may include a first taper 42 and a second taper 44, each of which may be sized and configured to manipulate a direction and orientation for the legs 20 to curl and/or wrap upon being compressed against an anvil (not shown), discussed further herein. The first taper 42 may extend from adjacent to the curved portion 21 of the legs along a majority of the length 36 of the legs 20. The second taper 44 may extend from an end of the first taper to a free end 43 of the legs 20 such that the second taper 44 is shorter than the first taper 42.

With reference to FIGS. 1 and 2, the capture member 14 will now be described. The capture member 14 may be sized and configured to be captured by the legs 20 of the anchor member 12 with tissue therebetween (see FIG. 1). The capture member 14 may include a pentagon type profile, or any other suitable profile, such as a circular profile or the like that may be employed for cooperating with and capturing the legs 20 of the anchor member 12. The capture member 14 may include coupling structure that may define apertures 46, recesses, notches or protrusions therein. Such coupling structure of the capture member 14, such as the apertures 46, recesses, notches, protrusions or any other suitable structure, may be sized and configured to receive and couple to the legs 20 of the anchor member 12. In this manner, the apertures 46 may be sized and positioned in the capture member 14 to correspond with the legs 20 of the anchor member 12.

Further, the capture member 14 may include an upper surface 48 and a lower surface 50 such that the apertures 46 extend through and between the upper and lower surfaces 48, 50 of the capture member 14. The capture member 14 may also define an outer periphery 52 and an inner periphery 54 such that the inner periphery 54 may define a central opening of the capture member 14. The upper surface 48 and the lower surface 50 of the capture member may extend to the outer and inner peripheries 52, 54 of the capture member 14. The capture member 14 may also include tines 56 extending upward above the upper surface 48. The tines 56 may extend from the inner periphery 54 and may be sized and configured to engage with soft tissue. Further, the tines 56 may extend in an inward canted manner or may extend substantially perpendicular relative to the upper surface 48 of the capture member 14. Such capture member 14, similar to the anchor member 12, may be formed as a monolithic, seamless structure from sheet material. As such, but for the tines 56, the capture member may be a substantially flat structure or configuration. Further, the upper surface 48 and lower surface 50 may extend in a planar manner. Further, the structure of the capture member 14 may define a capture member axis 57 that may extend centrally and axially relative to the structure of the capture member 14 such that the capture member axis 57 may extend substantially perpendicular relative to the upper and lower surfaces 48, 50 of the capture member 14.

In one embodiment, the sheet material for forming the anchor member 12 and the capture member 14 may be formed from a metallic material, such as stainless steel, titanium, or Nitinol, or any other suitable medical grade material or combinations of materials. As previously set forth, such anchor member 12 and capture member 14 may be laser cut from the sheet material or cut using any suitable technique known in the art. In another embodiment, the anchor member 12 may be formed from a polymeric material or a bioresorbable material, formed and manufactured as known by one of ordinary skill in the art. Upon being cut from the sheet material, the legs 20 of the anchor member 12 may be bent to position the legs downward or moved to orient the legs to extend away from a single side or underside of the anchor member 12. Similarly, the tines 56 of the capture member 14 may be bent upward, such as at a canted orientation or substantially perpendicular relative to the upper surface 48 of the capture member 14. Once the legs 20 or tines 56 have been appropriately oriented and bent into position, the anchor member 12 and capture member 14 may undergo an electro polishing or chemical polishing process, as known to one of ordinary skill in the art. In another embodiment, the anchor member 12 and/or the capture member 14 may be formed from a medical grade polymeric material, as known to one of ordinary skill in the art. In another embodiment, the anchor member 12 and/or the capture member may be formed from a bioresorbable material, as known to one of ordinary skill in the art.

Figure 3:
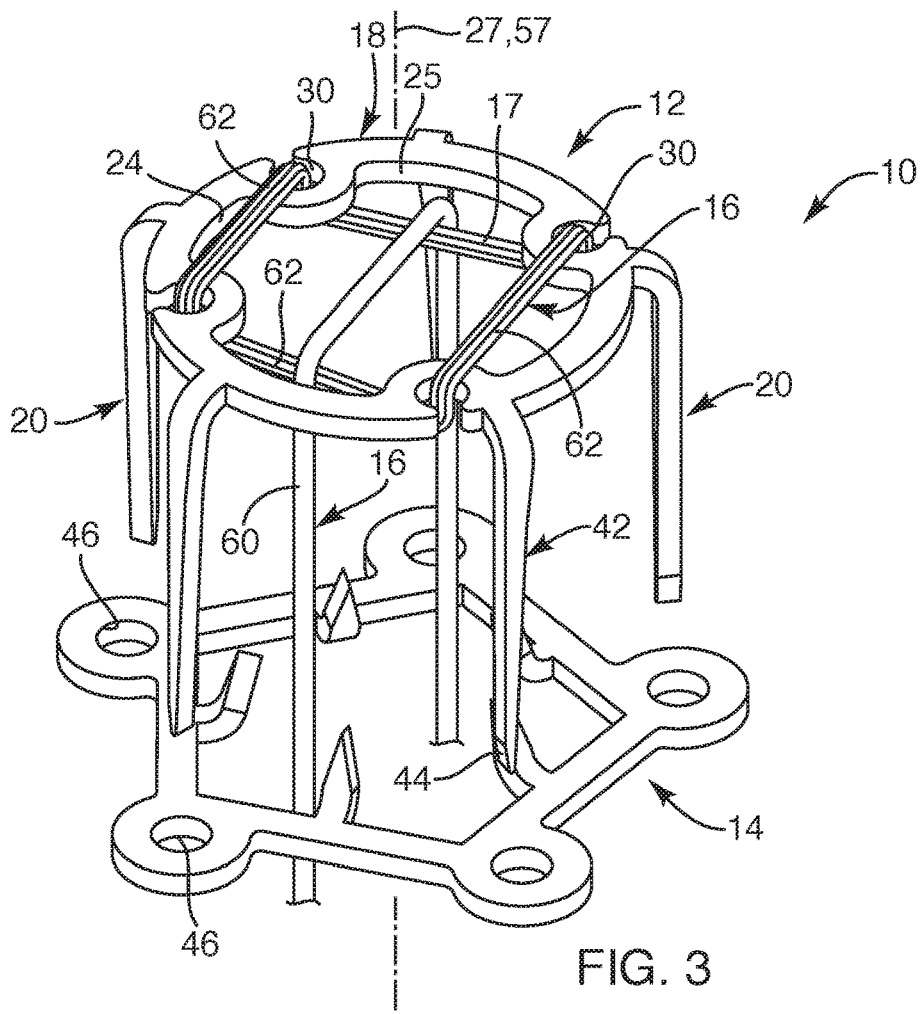
FIG. 3 is a perspective view of the repair device in a pre-deployed state, depicting legs of the anchor member aligned relative to coupling structure of the capture member, according to another embodiment of the present invention.
Figure 4:
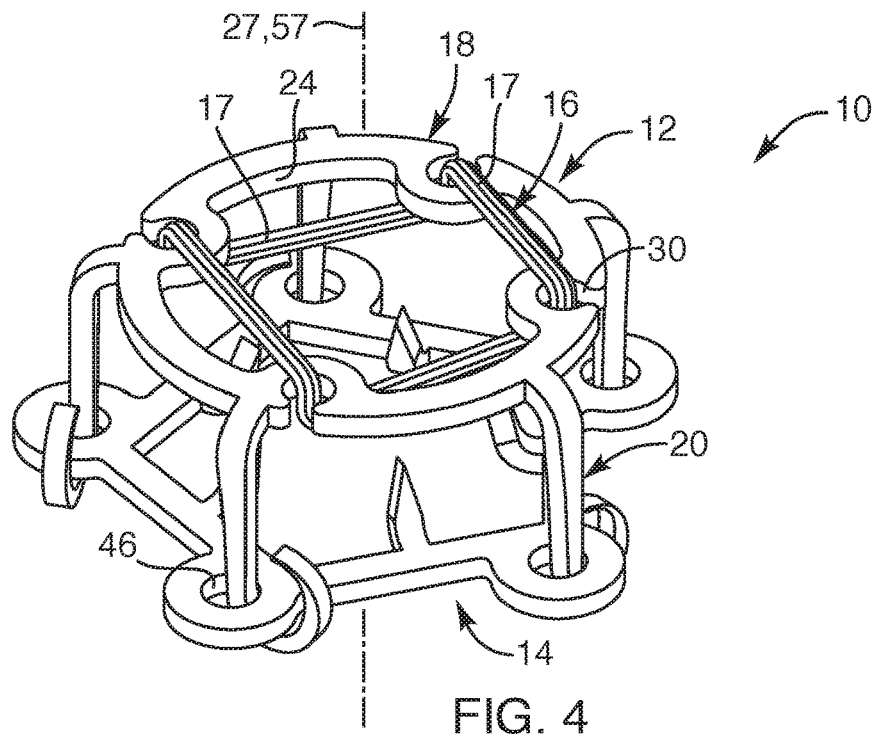
FIG. 4 is a perspective view of the repair device of FIG. 3 in a deployed and coupled state, depicting legs of the anchor member formed around coupling structure of the capture member, according to another embodiment of the present invention.

Now with reference to FIGS. 3 and 4, the anchor member 12 may be sized and configured to be coupled to the capture member 14, as depicted. For example, prior to the anchor member 12 and the capture member 14 being coupled together, the legs 20 of the anchor member 12 may be aligned with the apertures 46 of the capture member 14, as depicted in FIG. 3, such that the tissue anchor axis 27 and the capture member axis 57 may be substantially coaxial or substantially parallel relative to each other. The legs 20 of the anchor member 12 may be aligned to pass through the apertures 46 and moved to a formed position so that the legs 20 may curl and wrap around structural portions of the capture member 14. The first and second tapers 42, 44 defined in the width 38 (FIG. 1) of the legs 20 may be sized and configured to manipulate and provide consistency in the legs 20 being moved from a substantially straight, non-formed first position (FIG. 3) to a formed second position (FIG. 4). The formed second position of the legs 20 may exhibit a curled configuration along an end portion of the legs 20. In this manner, the capture member 14 may be captured by the legs 20 of the anchor member 12 with soft tissue (not shown) therebetween, discussed in more detail herein. In another embodiment, the capture member 14 may include structure, such as notches, protrusions or recesses defined therein, sized and configured to cooperate with the legs 20 so that the legs 20 of the anchor member 12 may curl or wrap around structural portions of the capture member 14, in a similar manner depicted in FIG. 4. Further, as depicted in FIG. 4, upon coupling the anchor member 12 to the capture member 14, the tissue anchor axis 27 and the capture member axis 57 may extend substantially coaxial or substantially parallel relative to each other.

In one embodiment, as depicted in FIG. 3, the one or more flexible members 16 may include the first flexible member 17 and a second flexible member 60. Although not shown in FIGS. 1 and 4, the second flexible member 60 may be pre-coupled to the first flexible member 17, as shown simplistically in FIG. 3 and described in further detail herein. For example, as previously set forth, the first flexible member 17 may be coupled to the base 18 of the anchor member 12. Such first flexible member 17 may be employed as a coupling for the second flexible member 60. The second flexible member 60 may extend over one or more portions of the first flexible member 17. For example, the first flexible member 17 may be coupled to the base 18 and extend adjacent the base 18 and along the inner periphery 24 of the base 18 so as to exhibit multiple lengths 62 or expanses of the first flexible member 17 extending between attachment points at the recesses 30 defined in the base 18. The second flexible member 60 may be coupled to the first flexible member 17 along, for example, the lengths 62 or a portion of the first flexible member 17. Such coupling of the second flexible member 60 to the first flexible member 17 is depicted in FIG. 3 in a simplified manner as extending over the first flexible member 17, but such coupling may be wrapped over or around portions of the first flexible member 17 along each length 62 or expanse between attachment points so as to be tied or wrapped in a fixed manner to the first flexible member 17. As can be appreciated, such coupling of the second flexible member 60 to the first flexible member 17 may be employed with a variety of configurations. Additional examples of the one or more flexible members 16 and the coupling thereof may be found in commonly owned U.S. Provisional Application No. 62/633, 000, the disclosure of which is hereby incorporated herein by reference in its entirety.

In one embodiment, the second flexible member 60 may extend with two free ends. In another embodiment, the second flexible member 60 may extend as a continuous loop. Such free ends or an end portion of a continuous loop may be configured to be coupled to a bone anchor (not shown), discussed further herein. In this manner, along such lengths 62 or portions of the first flexible member 17 being the coupling structure, the second flexible member 60 may be wrapped and coupled to the first flexible member 17. With this arrangement, the coupling between the second flexible member 60 and the first flexible member 17 may be more resistant to fatigue, fraying and/or deterioration since the coupling is between flexible members, without rigid edges between the coupling thereof. Further, such coupling may be advantageous because the first flexible member 17 may act somewhat resiliently to any force placed on the second flexible member 60. Further, upon a force being placed upon the second flexible member 60, such as from being coupled to a bone anchor, the coupling of the second flexible member 60 to the first flexible member 17, such as at each length 62 or expanse, may distribute the force along the base 18 of the anchor member 12. In this manner, the one or more flexible members 16 may act to distribute the force along the tissue adjacent the repair device 10 as well as minimize the stress being placed upon the soft tissue and the one or more flexible members 16 to, thereby, maintain the repair device 10 intact with the soft tissue.

Figure 5:
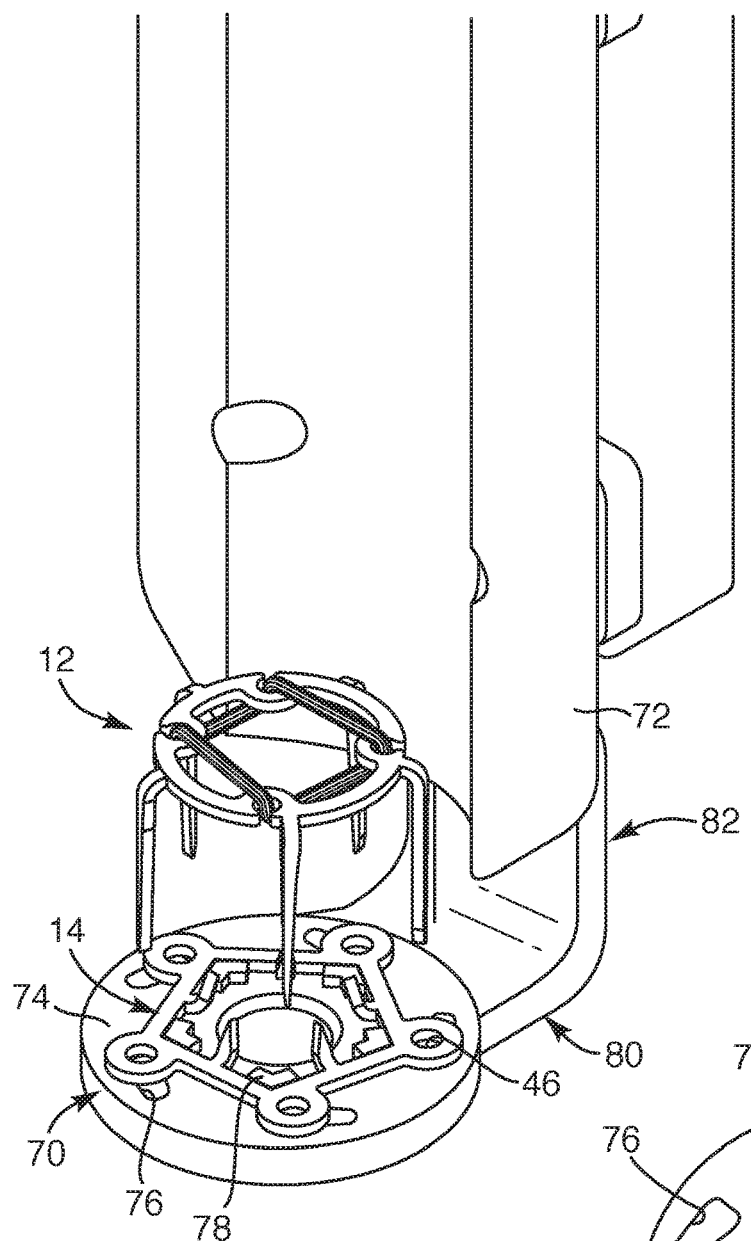
FIG. 5 is a perspective view of the repair device associated with an anvil, depicting the anchor member in the pre-deployed state as positioned within a cartridge (not shown) and positioned above the capture member disposed on the anvil, according to another embodiment of the present invention.
Figure 6:
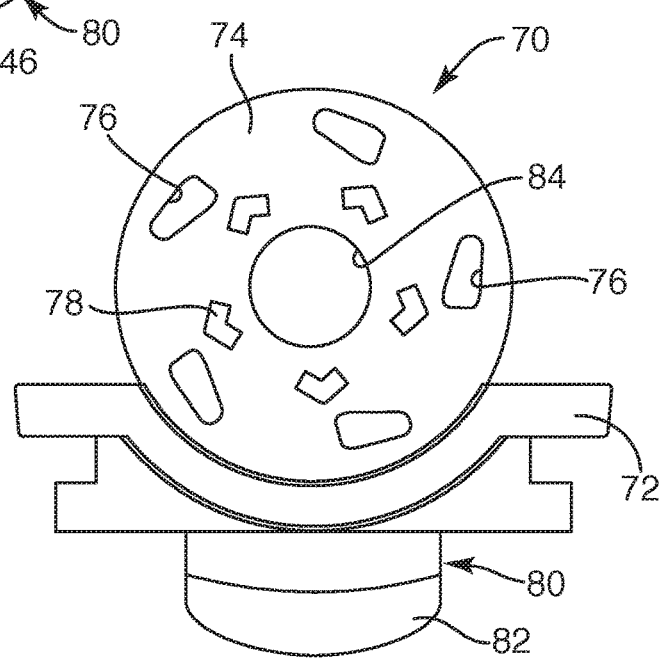
FIG. 6 is a top view of the anvil of FIG. 5, according to another embodiment of the present invention.

Now with reference to FIGS. 5 and 6, a portion of an implant delivery member 65 configured to couple the anchor member 12 to the capture member 14 is provided. The implant delivery member 65 may include, in part, an anvil 70 coupled to a guide portion 72 such that the implant delivery member 65 may be configured to couple to a delivery device (not shown). The guide portion 72 may include rails or the like for a cartridge (not shown) to be slidingly coupled thereto, discussed in further detail herein. The anvil 70 may include an anvil upper surface 74 with anvil buckets 76 defined therein. The anvil buckets 76 may be sized and configured to receive and engage the legs 20 of the anchor member 12 to facilitate curling the legs 20 (see FIG. 4) into the soft tissue (not shown) positioned over the anvil upper surface 74. Further, if employing the capture member 14, the capture member 14 may be positioned and temporarily secured over the anvil upper surface 74. For example, the anvil upper surface 74 may include multiple protrusions 78 positioned thereon to assist in precisely positioning the capture member 14 over the anvil upper surface 74 such that the protrusions 78 may be positioned to correspond with corners of the inner periphery 54 of the capture member 14. In this manner, the capture member 14 may be positioned so that the apertures 46 defined in the capture member 14 may be positioned over the anvil buckets 76 defined in the anvil upper surface 74. With the capture member 14 positioned on the anvil 70, the anchor member 12 may be positioned and aligned above the capture member 12 so that the legs 20 may be aligned with the apertures 46 of the capture member 14. Such anchor member 12 may be aligned and positioned above the capture member 14 by being held within a cartridge (not shown), discussed in further detail herein.

Figure 12:
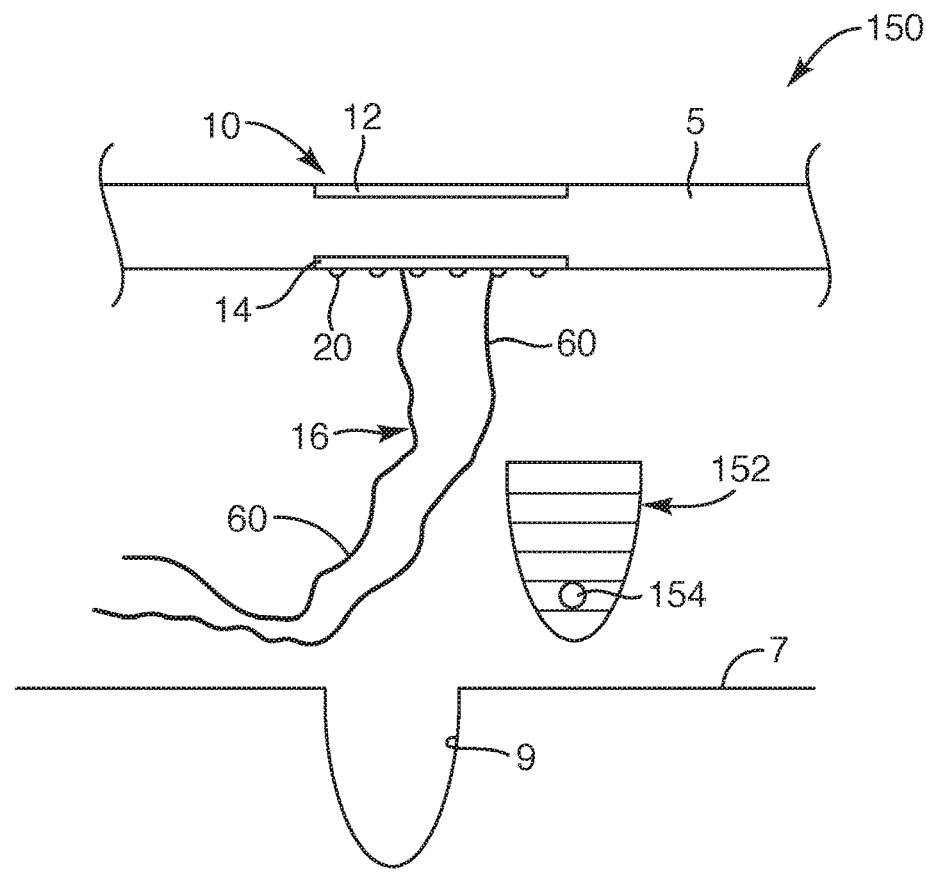
FIG. 12 is a simplified side view of the repair device coupled to soft tissue, depicting a bone anchor and a suture extending from the repair device, according to another embodiment of the present invention.

Once the capture member 14 may be positioned over the anvil upper surface 74, the soft tissue may then be positioned over the capture member 14. The anvil 70 may also include a neck portion 80 extending laterally from the anvil upper surface 74 with an upward extension 82 spaced from the anvil upper surface 74. The upward extension 82 of the neck portion 80 may be coupled to the guide portion 72. With this neck portion 80, there is additional space for positioning the soft tissue over the anvil upper surface 74 of the anvil 70. Upon positioning the soft tissue 5 over the anvil 70 (see FIG. 10), the anchor member 12 may then be delivered so as to compress the legs 20 through the soft tissue, through apertures 46 of the capture member 14, and into the anvil buckets 76. The anvil buckets 76 may be positioned and oriented in the anvil upper surface 74 such that the legs 20 of the anchor member 12 curl and wrap around structural portions of the capture member 14. In this manner, the anchor member 12 may be coupled to the capture member 14 with the soft tissue therebetween, as depicted in FIG. 4. Furthermore, the anvil upper surface 74 may define an aperture 84 extending through the anvil 70. Such aperture 84 may be employed for the one or more flexible members 16 or second flexible member 60 (see FIG. 3) to extend therethrough so that the one or more flexible members 16 may be coupled to a bone anchor 152 (FIG. 12).

Figure 7:
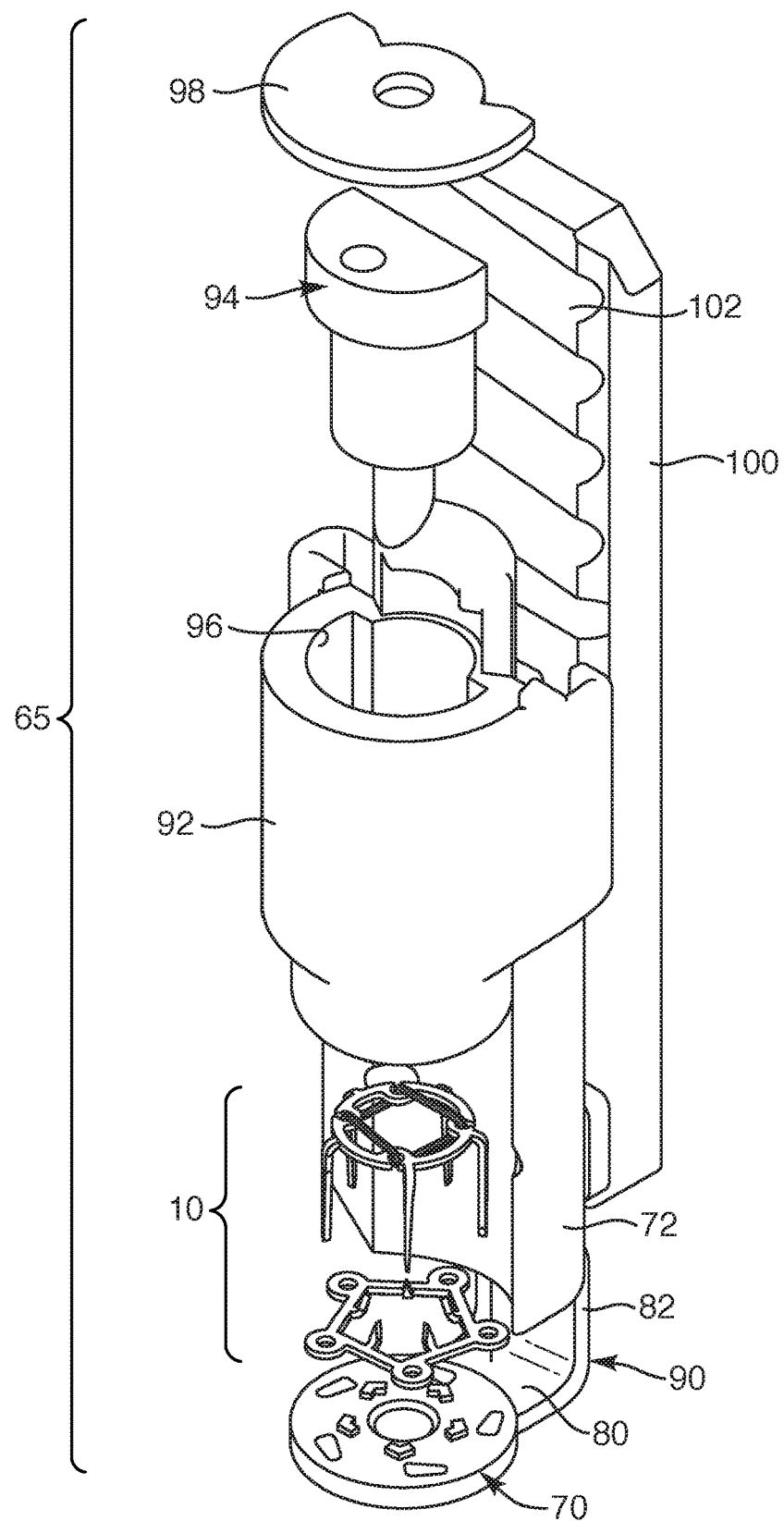
FIG. 7 is an exploded view of an implant delivery member and the repair device, according to another embodiment of the present invention.
Figure 8:
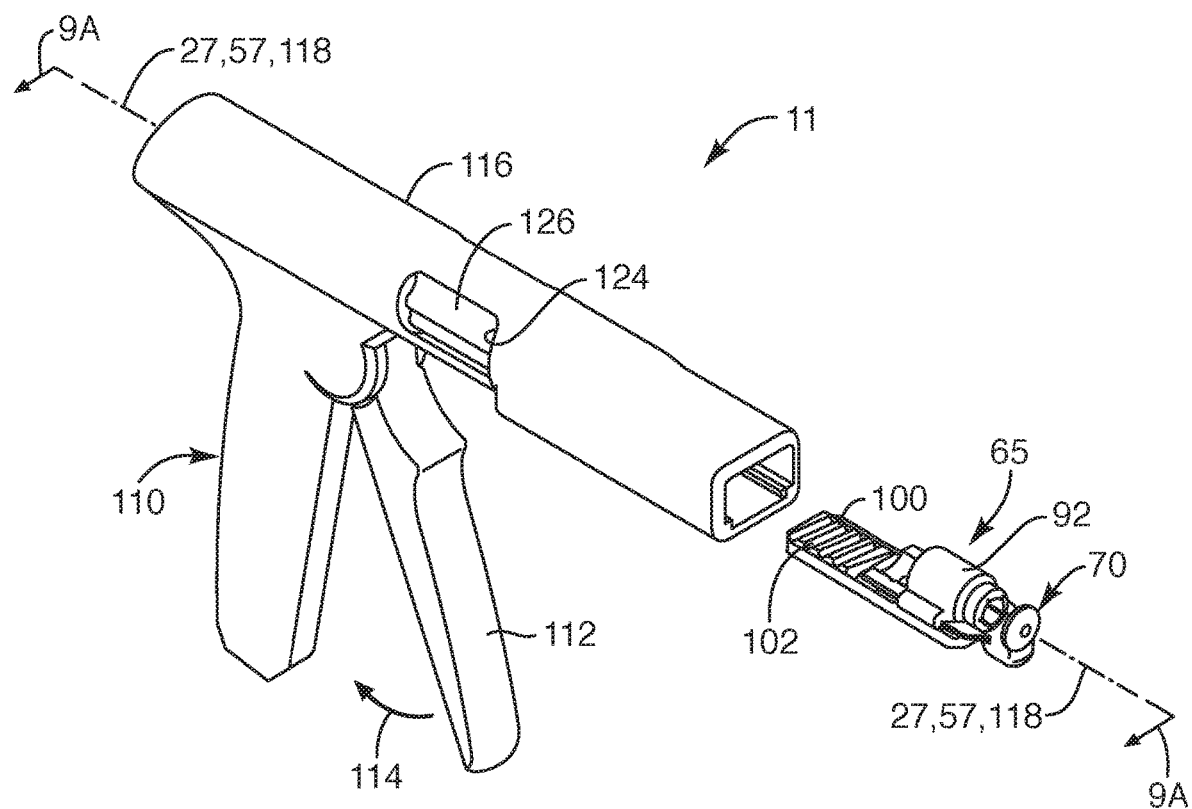
FIG. 8 is a perspective of a delivery device disengaged with the implant delivery member, according to another embodiment of the present invention.
Figure 8A:
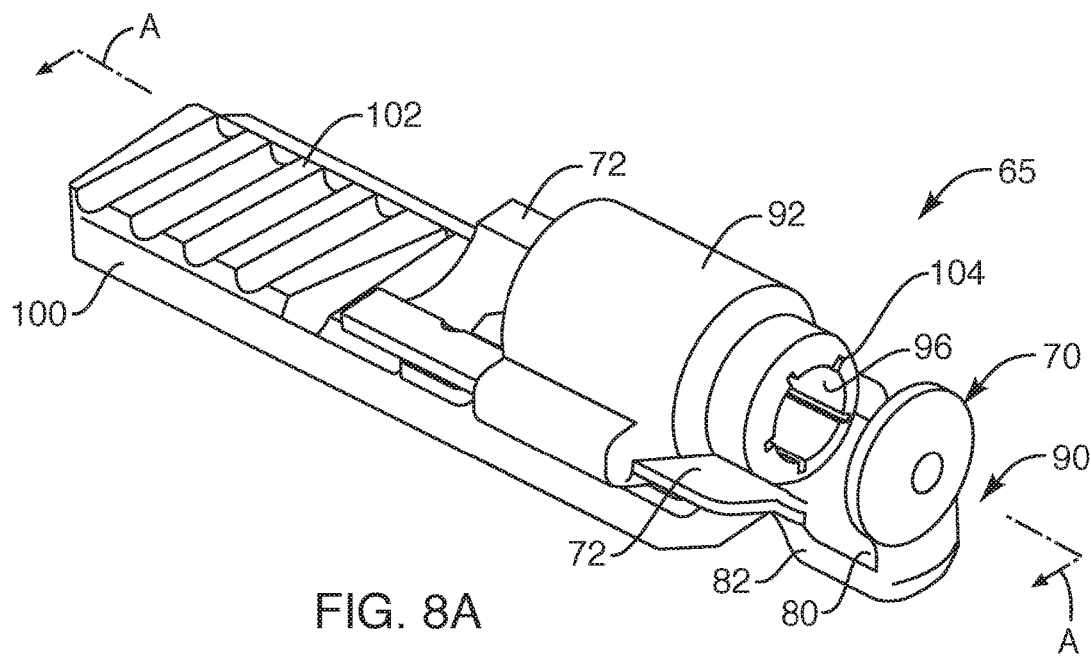
FIG. 8A is an enlarged perspective view of the implant delivery member, according to the present invention.

With reference to FIGS. 7 and 8A, the implant delivery member 65 will now be further described. As previously set forth, the implant delivery member 65 may be sized and configured to temporarily hold and house the repair device 10. Such implant delivery member 65 may be removably engaged with a delivery device 11 (FIG. 8), for example. The implant delivery member 65 may include various components that interact and cooperate with the delivery device 11 so that the repair device 10 may be deployed and fixated to soft tissue with the anvil 70 at an end portion of the implant delivery member 65 and the delivery device 11.

The implant delivery member 65 may include a cradle 90, a cartridge 92 and a pusher member 94, each of which may be sized and configured to cooperate with the repair device 10. The cartridge 92 may be linearly slidable along and coupled to the guide portion 72 with a c-arm or channel or the like extending along an underside of the cartridge 92. The guide portion 72 may be fixedly coupled to an elongated extension 82 of the cradle 90. The cartridge 92 may be hollow or define a hollow portion so as to define an opening 96 that may extend through opposite sides of the cartridge 92. The pusher member 94 may be positionable within a proximal side of the hollow portion or opening 96 of the cartridge 92. The proximal side of the opening 96 may be covered by a cap 98. Adjacent a distal side of the opening 96 or hollow portion, the anchor member 12 may be positioned distally adjacent the pusher member 94 within the cartridge 92. Further, the cartridge 92 may define internal grooves 104 in structure along the distal side of the hollow portion or opening 96, the internal grooves 104 sized and configured to hold the legs 20 of the anchor member 12 such that legs 20 of the anchor member 12 may be pushed through the cartridge 92 and along the internal grooves 104.

In one embodiment, the elongated extension 82 extending from the neck portion 80 of the cradle 90 may be fixedly coupled to a tongue portion 100. Such tongue portion 100 may be coupled to an underside of the elongated extension 82, the tongue portion 100 and elongated extension 82 may act and be referenced as a base or base portion of the implant delivery member 65. Further, the tongue portion 100 may include threads 102 along a portion thereof, such as along an upper side of the tongue portion 100, the threads 102 sized and configured to engage threads within the delivery device 11 (FIG. 8). In this manner, the implant delivery member 65 may be readily removed from and coupled to the delivery device 11.

Figure 9A:
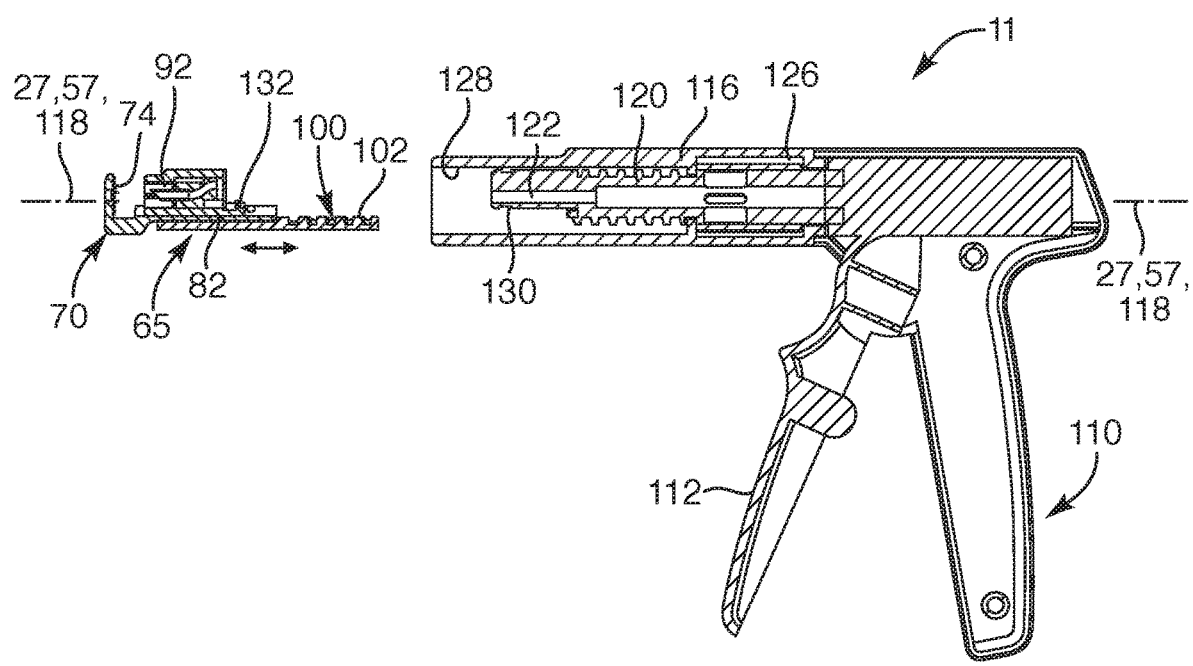
FIG. 9A is a cross-sectional view of the delivery device taken along section line 9A-9A of FIG. 8, according to another embodiment of the present invention.
Figure 9B:
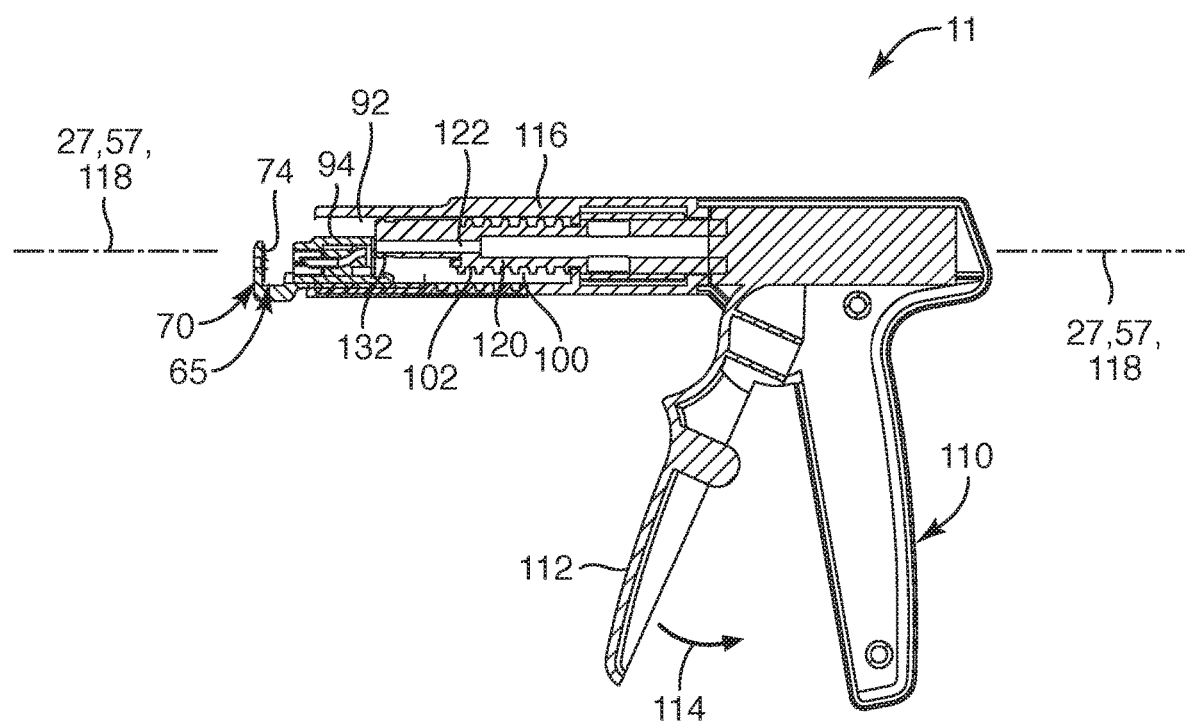
FIG. 9B is a cross-sectional view of the delivery device, depicting the implant delivery member engaged with the delivery device, according to another embodiment of the present invention.

Now with reference to FIGS. 8, 9A and 9B, the delivery device 11 sized and configured to deploy the repair device 10 (as depicted in FIG. 4) with the implant delivery member 65 will now be described. The delivery device 11 may include a trigger gun 110 with a trigger 112. The trigger gun 110 may be manually actuatable in a physician's hand by manually gripping or actuating the trigger 112, as shown with arrow 114. The delivery device 11 may also include a barrel housing 116 defining an axis 118. Such axis 118 of the delivery device 11 may extend coaxial relative to, or parallel with, the tissue anchor axis 27 of the anchor member 12 positioned in the cartridge 92 and the capture member axis 57 of the capture member 14 positioned over the anvil 70. The barrel housing 116 may house a worm drive 120 and a push rod 122 co-axial with the worm drive 120 and extending longitudinally through the worm drive 120. Such push rod 122 may be elongated so as to be co-axial or parallel with the axis 118. Further, such push rod 122 may be configured to cooperate with the trigger 112 so as to distally actuate upon actuating the trigger 112. A detailed description of a suitable trigger handle, capable of providing the force necessary to actuate the push rod 122, is disclosed in U.S. Pat. No. 5,344,061, the disclosure of which is hereby incorporated herein by reference in its entirety. The barrel housing 116 may also include one or more openings 124 or opposing openings defined therein such that a thumb wheel 126 may be positioned and accessible for manually rotating therein. Further, the delivery device 11 includes the replaceable and removable implant delivery member 65 such that the implant delivery member 65 may be removable relative to the barrel housing 116.

The thumb wheel 126 of the delivery device 11 may be manually rotatable to cooperate with the worm drive 120. As such, the physician may position the tongue 100 within an end opening 128 or within a bore of the barrel housing 116 and, for example, position the tongue 100 within a space below the push rod 122. Once positioned, the physician may rotate the thumb wheel 126 so that the worm drive 120 may engage the threads 102 of the tongue 100 and linearly move and pull the tongue 100 within the barrel housing 116. Upon engaging the tongue 100, the physician may continue to rotate the thumb wheel 126 so that the tongue 100 continues proximally so that the push rod 122 moves and slides the cartridge 92 distally until the cartridge 92 abuts and stops against the anvil 70 of the cradle 90. The push rod 122 may include a recess 130 at a distal end portion of the push rod 122. Upon the cartridge 92 being moved to a distal stop against the anvil 70 or cradle, further movement of the thumb wheel 126 may move the push rod 122 over a lip 132 adjacent a proximal side of the cartridge 92 so that the recess 130 in the push rod 122 engages and may be captured by the lip 132. The physician may hear, for example, a click as an assurance that the cartridge 92 is engaged with the push rod 122.

At this juncture, the push rod 122 may be engaged with the cartridge 92 such that reverse movement of the thumb wheel 126 may move the push rod 122 and the cartridge 92 proximally with linear movement. The physician may then move the cartridge 92 proximally a desired distance to then position soft tissue 5 over the anvil surface 74 and neck portion 80 (see FIG. 10). The cartridge 92 may then be moved linearly and distally to an appropriate position adjacent the soft tissue with the thumb wheel 126. Once the soft tissue and cartridge 92 are appropriately positioned, the trigger 112 of the delivery device 11 may be actuated to move the push rod 122 distally, extending along the axis 118, to push against the pusher member 94 to then push the repair device 10 from the cartridge 92 and into the soft tissue. As previously set forth, as the legs 20 of the anchor member 12 compress against the anvil buckets 76, the legs 20 move to a formed or curled position to wrap around portions of the capture members 18 (see FIGS. 4 and 5). At this juncture, the physician may then rotate the thumb wheel 126 to move the tongue 100 and cradle 90 distally so that the cartridge 92 is backed-off from the anvil 70 and so that the user may then readily remove the soft tissue with the deployed repair device 10 therein and from the cradle 70.

If it is desired to implant a second repair device in the soft tissue, the user may then continue to rotate the thumb wheel 126 to continue to move the implant delivery member 65 distally until the worm drive 120 is disengaged from the threads 102 of the tongue 100 of the implant delivery member 65. At this stage, the physician may take a second one of the implant delivery member 65 and position it within the barrel housing 116 for engaging with the delivery device 11 as described above to then position a second repair device in the soft tissue, if desired. In this manner, the implant delivery member 65 is removable and replaceable relative to the delivery device 11 so that the delivery device 11 may be repeatably employed with multiple implant delivery members 65.

The components of the delivery device 11 and implant delivery member 65 may be formed and made with medical grade materials, such as stainless steel, titanium, Nitinol, and/or alloys thereof or any other suitable metallic material or polymeric materials, such as liquid crystal polymers or acrylonitrile butadiene styrene ("ABS") or any other suitable polymeric materials known to one of ordinary skill in the art. Such components of the delivery device 11 may be formed by employing molding and/or machining techniques, or any other suitable techniques and processes known to one of ordinary skill in the art.

Figure 10:
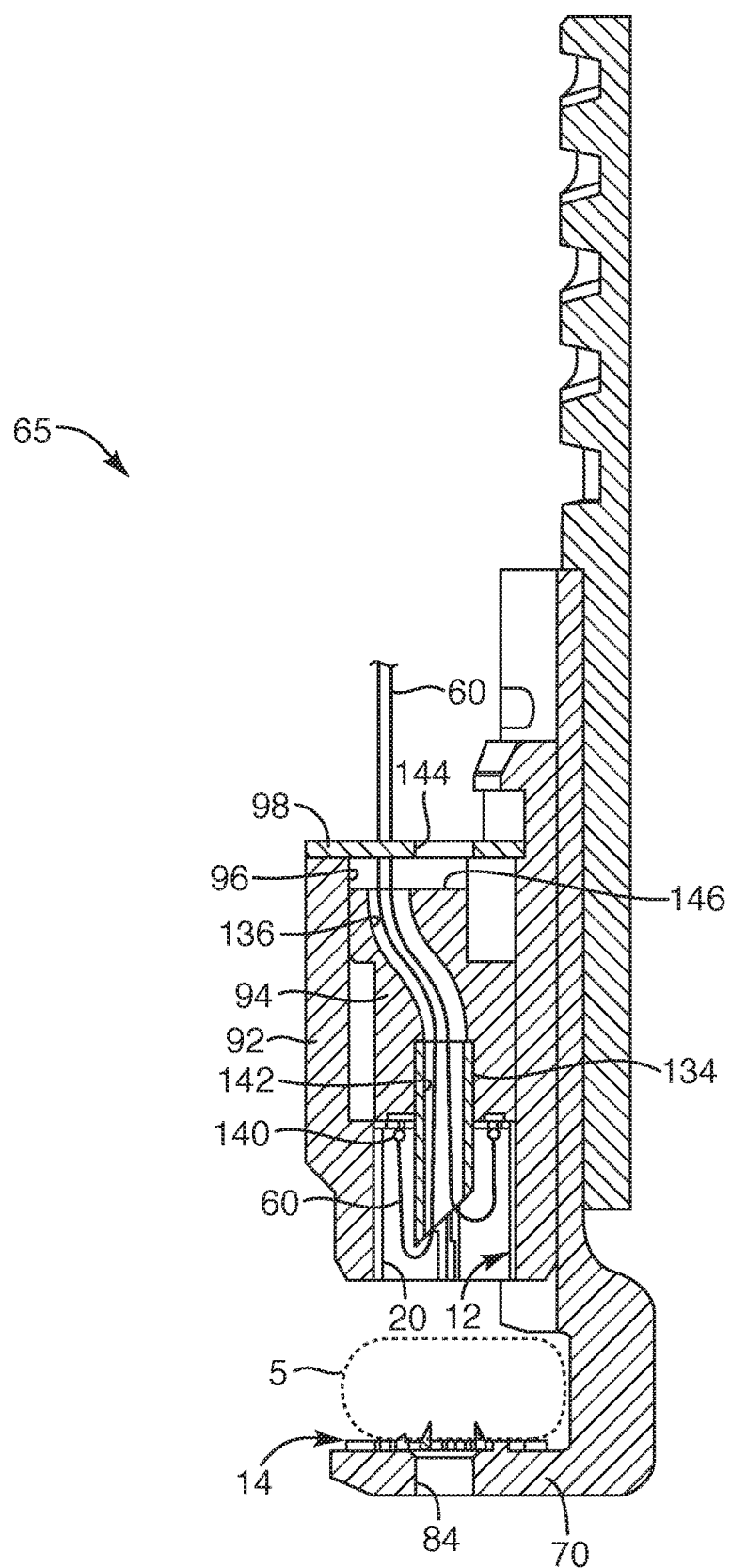
FIG. 10 is a cross-sectional view of the implant delivery member taken along section line A-A of FIG. 8A, according to another embodiment of the present invention.

With reference to FIG. 10, in one embodiment, the cartridge 92 of the implant delivery member 65 may include structure for manipulating a position of the one or more flexible members, such as the second flexible member 60, relative to the anchor member 12 of the repair device 10 (see also FIG. 3). For example, as previously set forth, the cartridge 92 may include the pusher member 94 positionable along a proximal side of the opening 96 or hollow portion defined in the cartridge 92. Further, the pusher member 94 may include a hollow needle 134 extending from a distal side of the pusher member 94. The hollow needle 134 may correspond with a hole 136 defined in the pusher member 94 that may extend with a curve through the pusher member 94. The hollow needle 134 may be sized and configured to correspond with the aperture 84 defined in the anvil 70. Further, the hollow needle 134 fixedly coupled to the pusher member 94 may be sized and configured to extend through the central opening 25 of the anchor member 12 positioned within a proximal side of the opening 96 of the cartridge 92. With this hollow needle 134 extending distally from the pusher member 94, the second flexible member 60 may extend from the first flexible member 17 at a coupling 140 between the first and second flexible members 17, 60 (see FIG. 3) such that the second flexible member 60 may extend distally to extend around an end of the hollow needle 134. The second flexible member 60 may then extend proximally through a conduit 142 of the hollow needle 134 and through the hole 136 defined in the pusher member 94 to continue proximally, for example, through an opening (not shown) in the cap 98 to be clipped or the like to an external surface of the implant delivery member 65. With this arrangement, the anchor member 12 may be deployed with the push rod 122 (FIG. 9B) extending through an aperture 144 defined in the cap 98 to engage a proximal surface 146 of the pusher member 94. The pusher member 94 may then move the anchor member 12 from the cartridge 92 to compress the legs 20 against the anvil buckets 76 to move the legs 20 around portions of the capture member 14 (See FIG. 5). Further, as the legs 20 are compressed by the pushing force of the pusher member 94, the hollow needle 134 is also pushed through the soft tissue 5 and through a central opening defined by the inner periphery 54 of the capture member 14 (FIG. 2) and through the aperture 84 defined in the anvil 70. Upon the hollow needle 134 extending through the aperture 84 of the anvil 70, the second flexible member 60 is pulled distally with the hollow needle 134 with portions of the second flexible member 60 extending through the soft tissue 5. The physician may then fully pull the second flexible member 60 completely through the soft tissue 5 and the aperture 84 defined in the anvil 70. In this manner, the delivery device or implant delivery member 65 may be sized and configured with a needle like structure to deliver the one or more flexible members, such as the second flexible member 60, to the underside of the soft tissue 5. As previously set forth, the cartridge 92 may be backed-off from the soft tissue 5 by rotating the thumb wheel 126 so that the soft tissue 5 may be removed from the anvil 70 (see also FIG. 9B) with the second flexible member 60 extending from an underside of the soft tissue 5, as depicted in FIG. 11.

Figure 11:
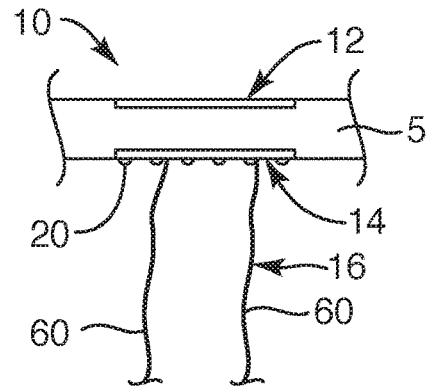
FIG. 11 is a simplified side view of the repair device of FIG. 4 coupled to soft tissue, depicting a flexible member extending from the repair device and the soft tissue, according to another embodiment of the present invention.

With reference to FIGS. 4 and 11, the anchor member 12 and capture member 14 of the repair device 10 may be coupled together with soft tissue 5 therebetween such that the legs 20 may extend through the soft tissue 5 to be moved to a curled, formed position, as previously set forth, to wrap around portions of the capture member 14. Further, the one or more flexible members may include the second flexible member 60 extending from, and coupled to, the first flexible member 17 such that the second flexible member 60 extends from the anchor member 12, through the soft tissue 5, and from an underside of the soft tissue 5. In this manner, the repair device 10 may be securely fixated to the soft tissue 5 with the second flexible member 60 extending therefrom. Such second flexible member 60 may be fixedly coupled, for example, to bone with a bone anchor (not shown) or any other structure desired by a physician.

Figure 11A:
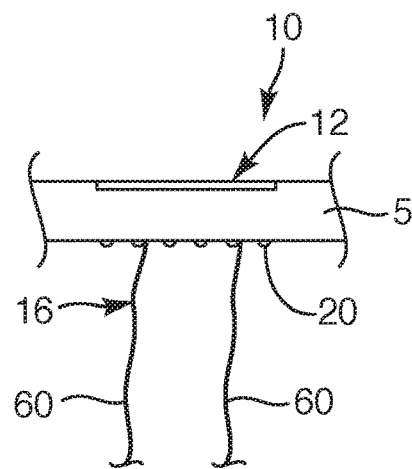
FIG. 11A is a simplified side view of another embodiment of a repair device coupled to soft tissue, depicting a flexible member extending from an anchor member and the soft tissue, according to the present invention.

Now with reference to FIGS. 1 and 11A, in another embodiment, the anchor member 12 of the repair device 10 may be fixated to soft tissue (without the capture member 14 of FIG. 2), as depicted in FIG. 11A, such that the legs 20 may be moved to the curled, formed position within the soft tissue 5 so that the anchor member 12 may be anchored to the soft tissue. In this embodiment, similar to the previous embodiment, the anchor member 12 may include the one or more flexible members 16 with, for example, the second flexible member 60 extending from the anchor member 12 such that the second flexible member 60 may extend through the soft tissue 5 and extend from an underside of the soft tissue 5.

With reference to FIGS. 4 and 12, an embodiment of a repair device system 150 for coupling soft tissue 5 to bone 7 is provided. In this embodiment, the repair device system 150 may include a bone anchor 152 and the repair device 10 having the anchor member 12 and the capture member 14, similar to that previously described. The bone anchor 152 may extend with an elongated structure defining a bone anchor axis along and axially relative to the elongated structure. Such bone anchor 152 may include structure along its external surface, such as ribs or threads, to assist the bone anchor 152 to couple to a pre-formed hole 9 in the bone 7. The bone anchor 152 may include a through hole 154 therein or other coupling feature, such as a notch or protruding extensions, sized and configured to couple the one or more flexible members 16, such as the second flexible member 60, to the bone anchor 152. Upon the repair device 150 being coupled to soft tissue 5 with the second flexible member extending from the anchor member 12, as described and depicted in FIGS. 9B, 10 and 11, the one or more flexible members may be threaded through, for example, the hole 154 defined in the bone anchor 152 to be coupled thereto. The bone anchor 152 may then be seated into and anchored in a pre-formed hole 9 in the bone 7 with the soft tissue cinched against the bone coupled thereto with the one or more flexible members 16. With this arrangement, the repair device 10 may be employed for fixating soft tissue 5 to bone 7.

Figure 13:
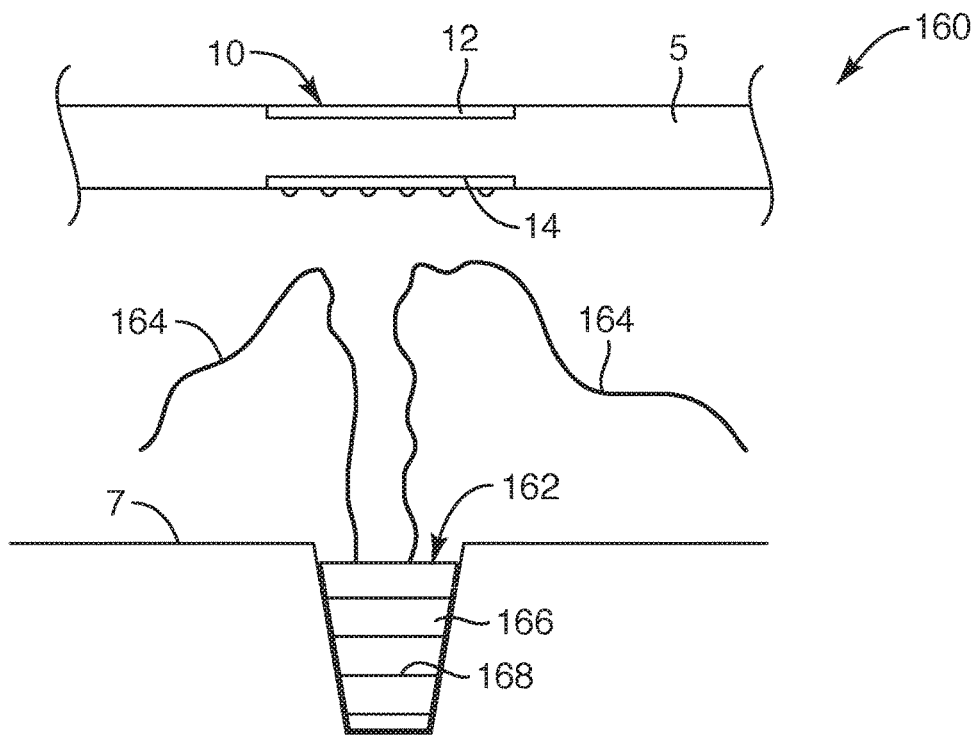
FIG. 13 is a simplified side view of the repair device coupled to soft tissue, depicting a bone anchor seated within bone with a flexible member extending from the bone anchor, according to the present invention.

Now with reference to FIGS. 4 and 13, another embodiment of a repair device system 160 for coupling soft tissue 5 to bone 7 is provided. In this embodiment, the repair device system may include a bone anchor 162 and the repair device 10. As previously set forth, the repair device 10 may include the anchor member 12 that may be coupled to soft tissue 5 with the capture member 14, similar to previous embodiments. The bone anchor 162 may include one or more flexible members 164 coupled to and extending from the bone anchor 162. Such one or more flexible members 164 may be suture type filaments or the like and may be pre-coupled to the bone anchor 162 or may be coupled to the bone anchor 162 through the procedure of seating the bone anchor 162 into the bone 7. The bone anchor 162 may include an outer surface 166 defining ridges 168 or threads to facilitate coupling to the bone 7 or a base structure previously embedded in the bone 7. Such bone anchor 162 employed in the repair device system 160 may be any suitable bone anchor 162 with one or more flexible members 164 coupled thereto. Upon embedding the bone anchor 162 in the bone 7 and the repair device 10 being coupled to the soft tissue 5, such as tendon or ligament, the one or more flexible members 164 may be threaded through the soft tissue 941 and through the central opening 25 of the anchor member 12. The one or more flexible members 164 may then be tied and knotted to the first flexible member 17 coupled to the anchor member 12. Through the process of coupling the one or more flexible members 164 to the first flexible member 17, the soft tissue 5 and repair device 10 may be cinched in against or adjacent to the bone 7 and/or bone anchor 162 with the one or more flexible members 164. Once the one or more flexible members 164 are coupled to the anchor member 12 via the first flexible member 17, any excess portions of the one or more flexible members 164 may be clipped-off by the physician.

Figure 14:
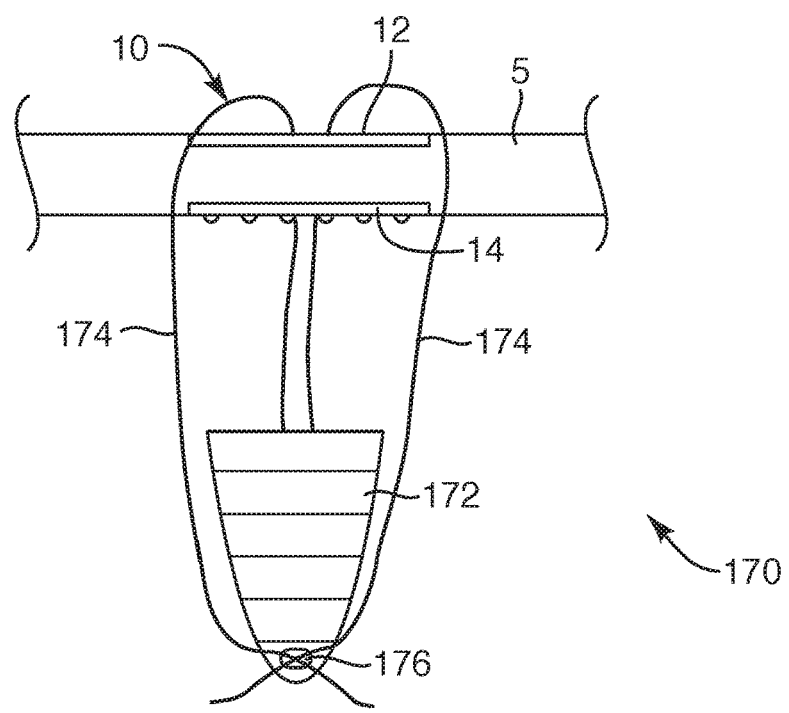
FIG. 14 is a simplified side view of the repair device coupled to soft tissue, depicting a bone anchor coupled to the repair device with a flexible member, according to another embodiment of the present invention.

Now with reference to FIGS. 4 and 14, another embodiment and method of coupling soft tissue to bone with a repair device system 170 is provided. In this embodiment, similar to previous embodiments, the repair device system 170 includes a bone anchor 172 and the repair device, the repair device 10 including the anchor member 12 and the capture member 14. The repair device 10 may be coupled to soft tissue 5 adjacent a soft tissue repair site and may be employed to be coupled to the bone anchor 172 such that the anchor member may include the one or more flexible members, such as the first flexible member 17. The bone anchor 172 may include one or more flexible members 174 coupled thereto that extend from the bone anchor 172. Upon the repair device 10 being coupled to the soft tissue, the one or more flexible members 174 of the bone anchor 172 may by threaded through the inner periphery 54 of the capture member 14, through the soft tissue 5 and through the central opening 25 defined in the anchor member 12. The one or more flexible members 174 may then be threaded over the repair device 10 and through the soft tissue 5 and through a hole 176 of the bone anchor or other coupling structure of the bone anchor. The ends of the one or more flexible members 174 may then be pulled to cinch the soft tissue 5 to a desired position, such as adjacent the bone anchor 172. The bone anchor 172 with the soft tissue 5 and repair device 10 cinched thereto may then be seated in a pre-formed hole in bone (not shown). In this manner, the repair device 10 of this embodiment may be employed to fixate soft tissue 5 to bone.

Figure 15:
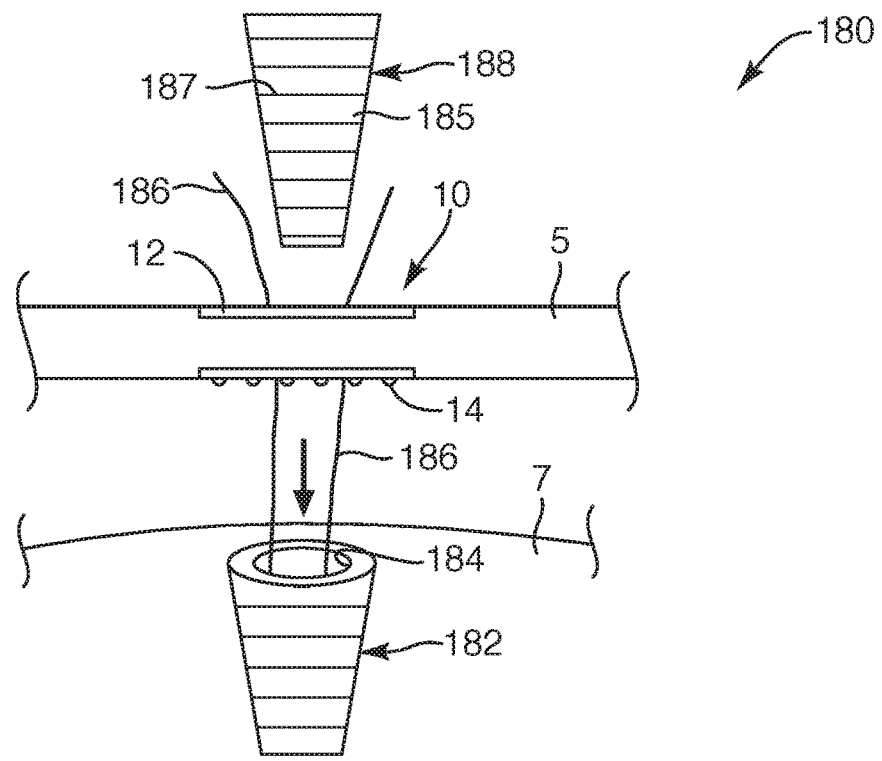
FIG. 15 is a simplified side view of another embodiment of the repair device coupled to soft tissue, depicting a post configured to cooperate with the repair device, a flexible member and a bone anchor, according to another embodiment of the present invention.

With reference to FIGS. 4 and 15, another embodiment of a repair device system 180 including the repair device 10 that may be employed with a bone anchor 182 is provided. As in the previous embodiments, the repair device 10 may include the anchor member 12 and the capture member 14 for fixating to the soft tissue and may be employed for coupling to a bone anchor 182. For example, the bone anchor 182 may define a central bore 184 extending within at least one end of the bone anchor 182. The bone anchor 182 may also include one or more flexible members 186 extending therefrom, such as, extending from within the bore 184 that may be pre-coupled to the bone anchor 182. Upon seating and/or coupling the bone anchor 182 into bone 7 and upon deploying the repair device 10 to couple to the soft tissue 5, the one or more flexible members 186 may be threaded through the capture member 14, the soft tissue 5 and through the central opening 25 of the anchor member 12. The soft tissue 5 may then be cinched down to the bone anchor 182 while the physician holds the one or more flexible members 186 taut so that the central opening 25 of the anchor member 12 and the capture member 14 are substantially aligned with the bore 184 of the bone anchor 182. The soft tissue 5 may then be coupled to the bone 7 and bone anchor 182 by inserting a post 188 through the central opening 25 of the anchor member 12 and the capture member 14 and into the bore 184 of the bone anchor 182. The post 188 may define fastening structure on an outer surface 185 of the post 188, such as ribs 187 and/or threads, sized and configured to couple to the bone anchor 182 and the repair device 10. As such, the post 188 may be sized and configured with tolerances to fit tight within the central opening 25 of the repair device 10 and the bore 184 of the bone anchor 182 such that the one or more flexible members 186 may be sandwiched between the outer surface 185 of the post 188 and the corresponding inner surfaces of the repair device 10 and the bone anchor 182. In this manner, it may not be necessary for a physician to tie off the one or more flexible members 186 with knots since the post facilitates a coupling between the one or more flexible members 186 and the repair device 10. Further, if desired, the physician may loop and thread the one or more flexible members 186 around and through the repair device 10 multiple times and tie-off the one or more flexible members 186 to the repair device 10 and then insert the post 188, as previously set forth, thereby providing a more fail safe dual coupling of the one or more flexible members 186 and the post 188. In either case, the repair device 10 of this embodiment may be employed with the post 188 and the one or more flexible members 186 for coupling the soft tissue 5 to bone 7.

Figure 16:
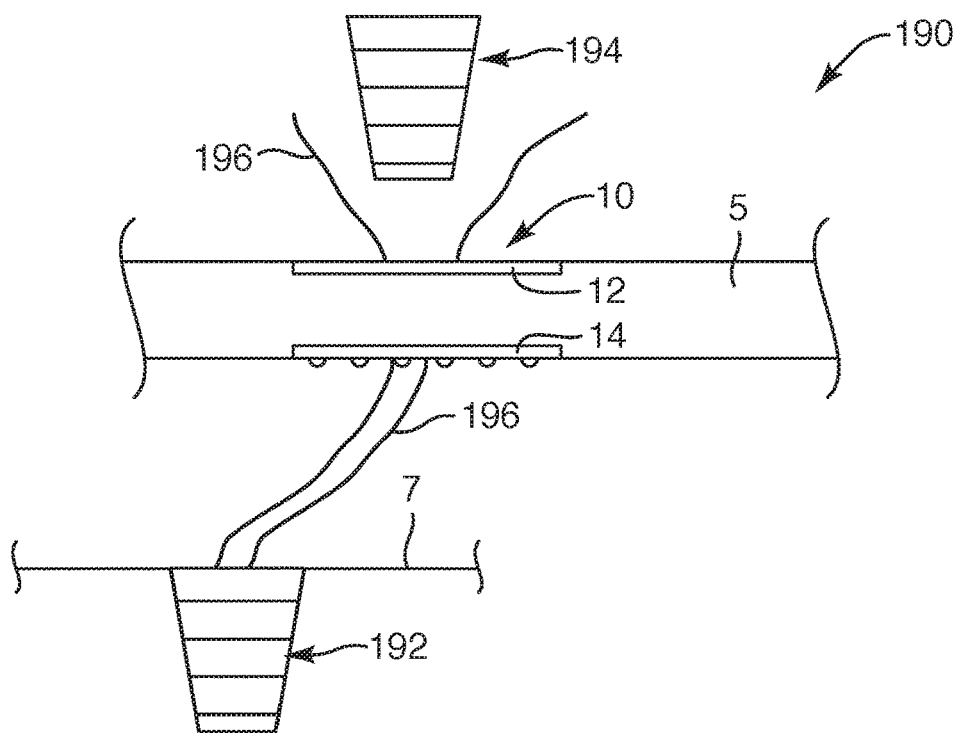
FIG. 16 is a simplified side view of another embodiment of the repair device coupled to soft tissue, depicting a post configured to cooperate with the repair device and a flexible member extending from a bone anchor seated within bone, according to another embodiment of the present invention.

With respect to FIGS. 4 and 16, another embodiment and method for coupling soft tissue to bone with a repair device system 190 is provided. In this embodiment, the repair device system 190 may include the repair device 10 that may be employed with a bone anchor 192 and a post 194. This embodiment is similar to the previous embodiment except the post 194 may be sized to only couple to the repair device 10 and not directly to the bone anchor 192. Similar to the previous embodiment, the post 194 may sandwich one or more flexible members 196 extending from and coupled to the bone anchor 192 between an outer surface 195 of the post 194 and the inner surface defining the central opening 25 of the anchor member 12 and the inner periphery 54 defining a hole of the capture member 14, thereby, coupling the soft tissue 5 to the bone 7. In this embodiment, the physician may not need to align the central opening 25 of the repair device 10 with the bone anchor 192, but may cinch the soft tissue 5 toward the bone 7 to a desired position to then simply insert the post 194 into the repair device 10, which in turn, fastens the one or more flexible members 196 to the repair device 10. In this manner, the repair device 10 may be employed for coupling to the soft tissue 7 so that the soft tissue 5 can be coupled and fixated to the bone 7 with the bone anchor 192 and post 194 arrangement.

Figure 17A:
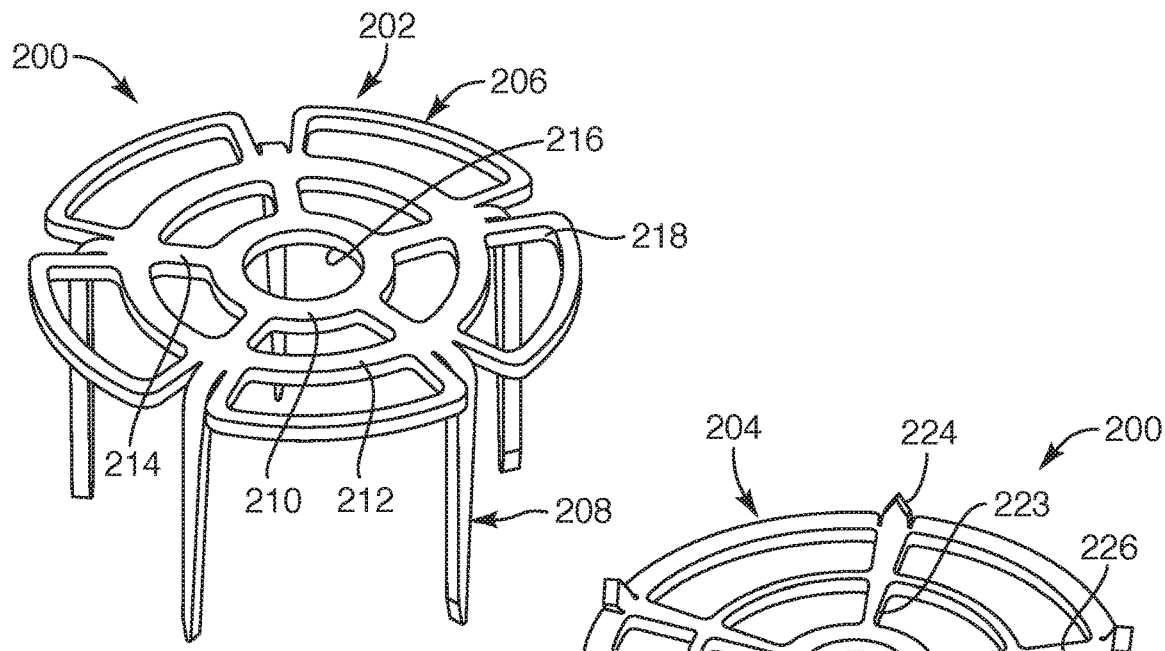
FIG. 17A is a perspective view of another embodiment of an anchor member of a repair device, according to the present invention.
Figure 17B:
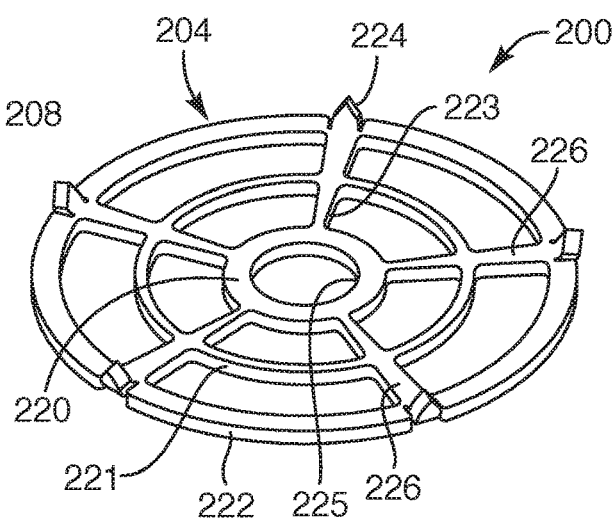
FIG. 17B is a perspective view of another embodiment of a capture member, according to the present invention.

Now with reference to FIGS. 17A and 17B, another embodiment of a repair device 200 with an anchor 202 and a capture member 204 is provided. The anchor 202 may be sized and configured to be deployed into soft tissue to couple to the capture member 204 with the soft tissue therebetween, similar to previous repair device embodiments. The repair device 200 of this embodiment may be employed for coupling to soft tissue, such as tendon or ligament, in the shoulder or ankle regions, for example, to be coupled to bone with a bone anchor.

With respect to FIG. 17A, the anchor 202 may include a base 206 with legs 208 extending therefrom. The base 206 may exhibit a circular profile and define an inner ring portion 210 and an outer ring portion 212 with spokes 214 extending radially between the inner ring portion 210 and the outer ring portion 212. The inner ring portion 210 of the anchor may define a central opening 216 of the anchor 202. In addition, the outer ring portion 212 may include wing portions 218 extending radially outward from the outer ring portion 212. Further, the legs 208 may extend downward from the outer ring portion 212 between adjacently extending wing portions 218. The wing portions 218 may extend outward beyond the legs 208 to facilitate a larger area for the anchor 202 to sandwich the soft tissue with the capture member 204. The legs 208 may include structural characteristics similar to legs 208 of previous embodiments such that the legs 208 may be sized and configured to be deployed through soft tissue and configured to move to a curled position through the tissue.

With respect to FIGS. 17A and 17B, the capture member 204 may be sized and configured to be engaged and coupled to the legs 208 of the anchor 202, the capture member 204 including a circular profile with features that correspond with the anchor 202. For example, the capture member 204 may include an inner circular portion 220, a middle circular portion 221, and an outer circular portion 222 with spoke portions 203 extending radially from the inner circular portion 220 to the outer circular portion 222. The capture member 204 may also include multiple tines 224 extending from a surface of the outer circular portion 222, the tines 224 sized and configured to engage soft tissue. In one embodiment, the tines 224 may be positioned to be aligned with and adjacent to outer ends of the spoke portions 223. Further, the capture member 204 may also include a central hole 225 sized to correspond with the central opening 216 of the anchor 202. Similar to previous embodiments, the capture member 204 may be positioned on a anvil upper surface of a anvil and the anchor 202 may be positioned within a cartridge. Upon positioning soft tissue over the capture member 204 and over the anvil upper surface, the anchor 202 may be deployed from the cartridge such that the legs 208 of the anchor 202 may extend through the soft tissue, engage anvil buckets defined in the anvil so that the legs 208 move to the curled position and wrap around a portion of the capture member 204. For example, the capture member 204 and anchor 202 may be positioned such that the legs 208 curl around outer spoke portions 226 of the capture member 204. With this arrangement, the anchor 202 and capture member 204 may be employed for coupling soft tissue to bone similar to that depicted in FIG. 11 such that one or more flexible members may be coupled to the anchor 202 so that the one or more flexible members may be coupled to a bone anchor, similar to that set forth in any one of the embodiments depicted and described in FIGS. 12-14.

Figure 18A:
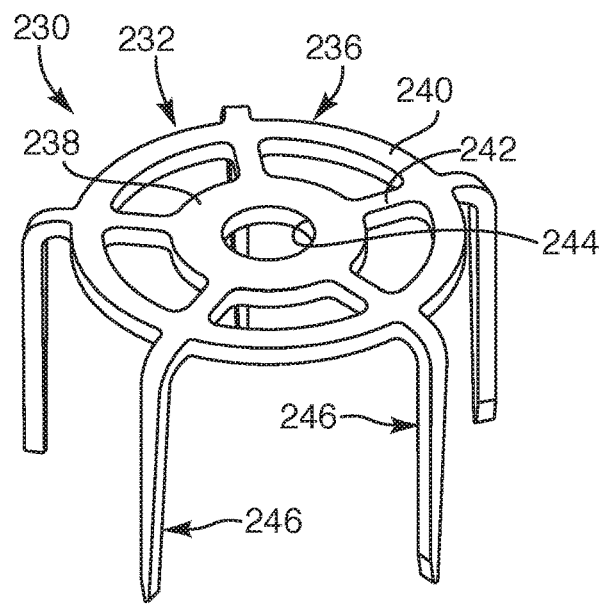
FIG. 18A is a perspective view of another embodiment of an anchor member of a repair device, according to the present invention.
Figure 18B:
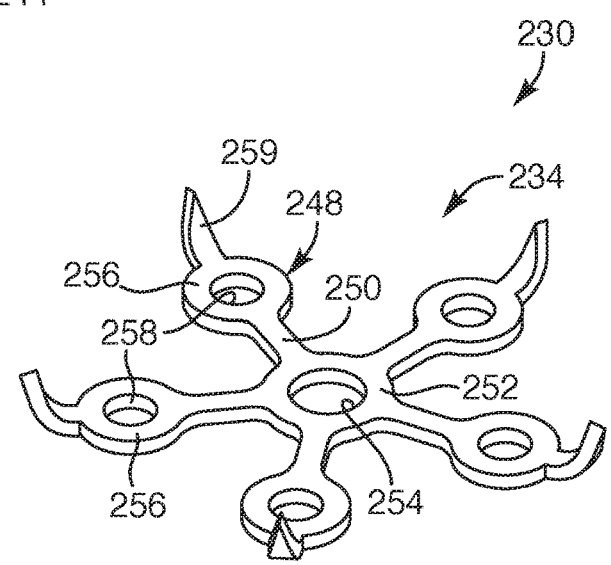
FIG. 18B is a perspective view of another embodiment of a capture member, according to the present invention.

With reference to FIGS. 18A and 18B, similar to the previous embodiment, another embodiment of a repair device 230 having an anchor 232 and a capture member 234 sized and configured to couple to soft tissue, such as tendon or ligament, is provided. The anchor 232 is similar to the previous embodiment, except the anchor 232 does not include the wing portions. The anchor 232 may include a base 236 having an inner ring portion 238 and an outer ring portion 240 with radially extending spokes 242 extending therebetween, the inner ring portion 238 defining a central opening 244 therein. Further, the base 236 may include legs 246 extending downward from the base 236 such that the legs 246 may be positioned along the base 236 in an aligned manner relative to the spokes 242, the legs 246 sized and configured to move to a curled position upon deploying the anchor 232 from a delivery device, similar to the previous embodiments described herein.

In this embodiment, the capture member 234 may include a base 248 with spokes 250, such as five spokes, extending from a central portion 252. The central portion 252 defines a central hole 254 configured to correspond with the central opening 244 of the anchor 232. The spokes 250 may extend radially from the central portion 252. Further, each spoke 250 may include structure 256 defining an aperture 258 at an outer end thereof. Further, the structure 256 defining the aperture 258 may include a tine 259 or spike extending therefrom sized and configured to engage and grab soft tissue. With this arrangement, the capture member 234 may be positioned on a cradle so that the legs 246 of the anchor 232 may be aligned with the apertures 258 of the capture member 234 such that, upon the anchor 232 being deployed from the cartridge, the legs 246 extend through the apertures 258 to then engage anvil buckets to curl around the structure 256 defining the apertures 258. In this manner, the anchor 232 and the capture member 234 may be coupled to soft tissue, similar to previous embodiments, which may be coupled to bone with one or more flexible members coupled to an embedded bone anchor, similar to that depicted in FIGS. 11-14. Such one or more flexible members may be threaded through the soft tissue and the central opening 244 of the anchor 232 and the central hole 254 of the capture member 234.

Figure 19A:
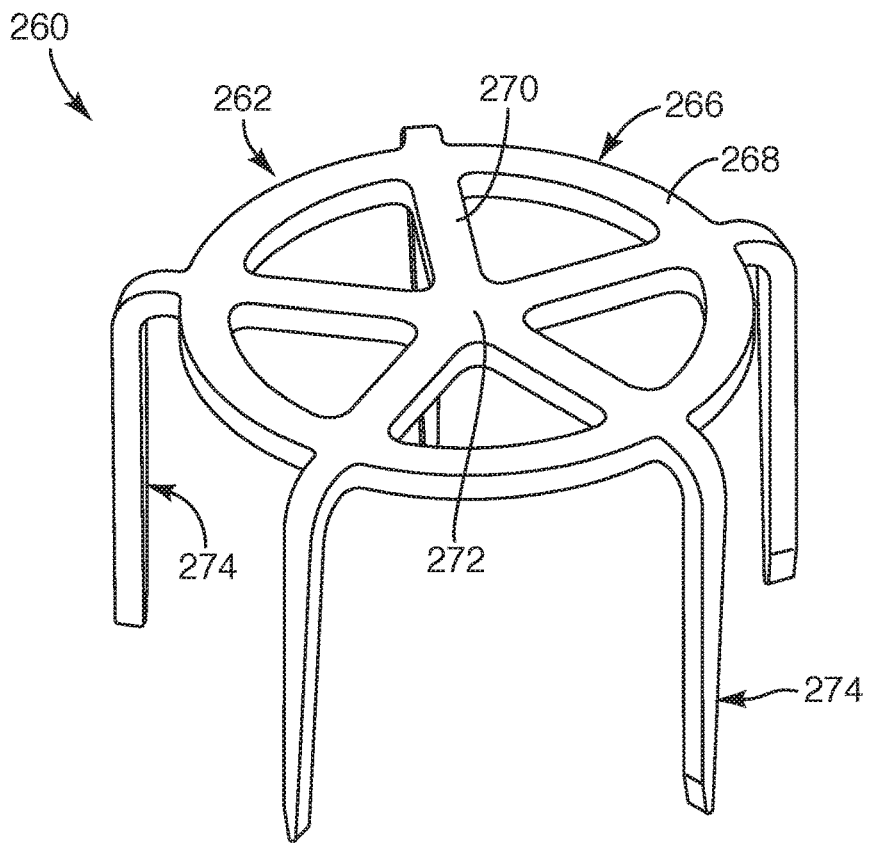
FIG. 19A is a perspective view of another embodiment of anchor member of a repair device, according to the present invention.
Figure 19B:
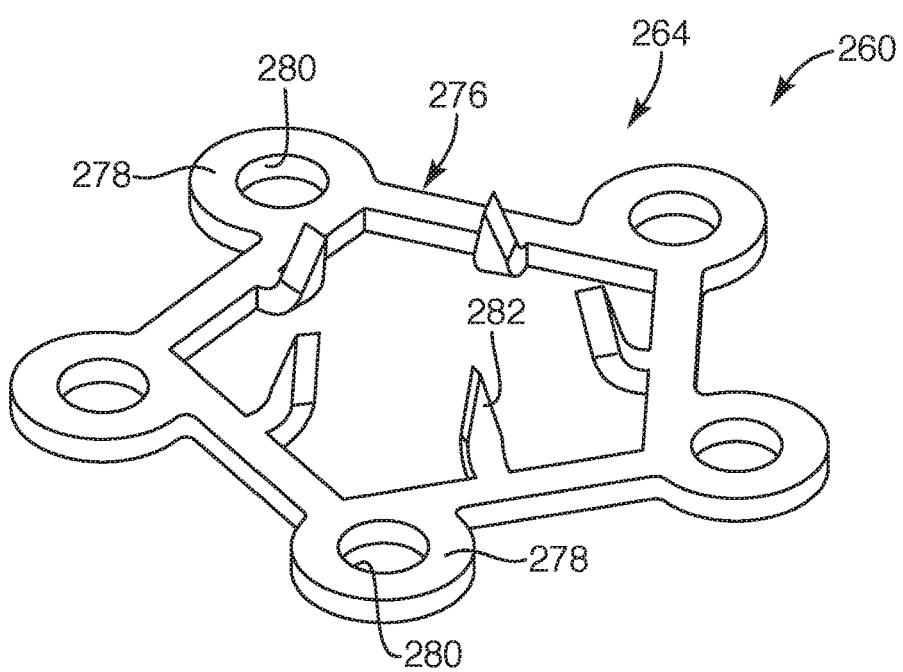
FIG. 19B is a perspective view of another embodiment of a capture member, according to the present invention.

With reference to FIGS. 19A and 19B, another embodiment of a repair device 260 having an anchor 262 and a capture member 264, similar to previous embodiments, is provided. The anchor 262 may include a base 266 having an outer circular portion 268 with spokes 270 extending radially inward to a central portion 272, the base 266 including legs 274 extending downward from the outer circular portion 268. The capture member 264 may include an outer frame portion 276 that may extend with a pentagon shape. The outer frame portion 276 may include structure 278 defining apertures 280 along an outer periphery of the outer frame portion 276, the structure 278 defining the apertures 280 may be positioned adjacent corners of the pentagon shaped outer frame portion 276. The apertures 280 may be sized to correspond with the legs 274 of the anchor 282 such that the legs 274 may extend through the apertures 280 and curl around the structure 278 defining the apertures 280, similar to the previous embodiment. Further, the outer frame portion 276 may include tines 282 extending inward and upward from the outer frame portion 276. As in previous embodiments, such tines 282 of the capture member 274 may be sized and configured to engage and grab into soft tissue.

Figure 20:
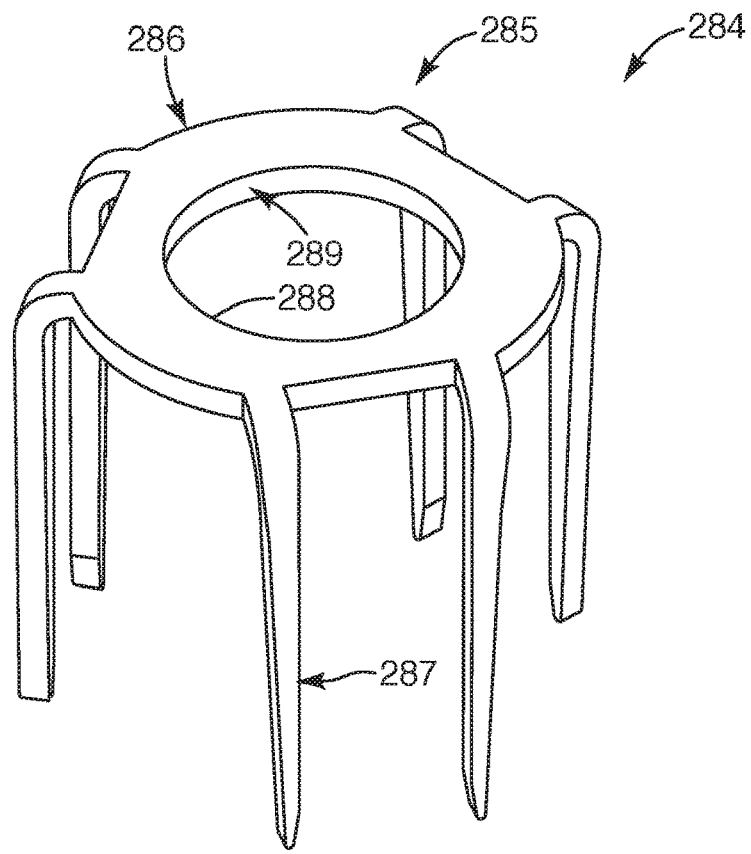
FIG. 20 is a perspective view of another embodiment of an anchor member of a repair device, according to the present invention.

With reference to FIG. 20, another embodiment of a repair device 284 that may be employed for fixating to soft tissue such that the repair device 284 may be coupled to bone with a bone anchor. Similar to previous embodiments, the repair device 284 may include an anchor 285 that may be employed alone to fixate to soft tissue and may also be employed to couple to a capture member, such as any one of the capture members described and depicted in FIGS. 2, 17B, 18B and 19B. Further, the anchor 285 may be deployed from a cartridge of a delivery device, similar to that described and depicted in FIGS. 8, 9A and 9B. The anchor 285 may include a base 286 with legs 287 extending therefrom, the legs 287 sized and configured to be moved to a curled and formed position for fixating to soft tissue. The base 286 may include an outer periphery and an inner periphery 288, the inner periphery 288 defining a central opening 289 of the anchor 284. The anchor 284 of this embodiment having the central opening 289 defined in the base 286 may be suitable to couple to a bone anchor, similar to that described and depicted relative to FIGS. 11 through 16. Further, the anchor 285 of this embodiment may include the one or more flexible members coupled to the base 286 or legs 287 of the anchor 285.

Figure 21:
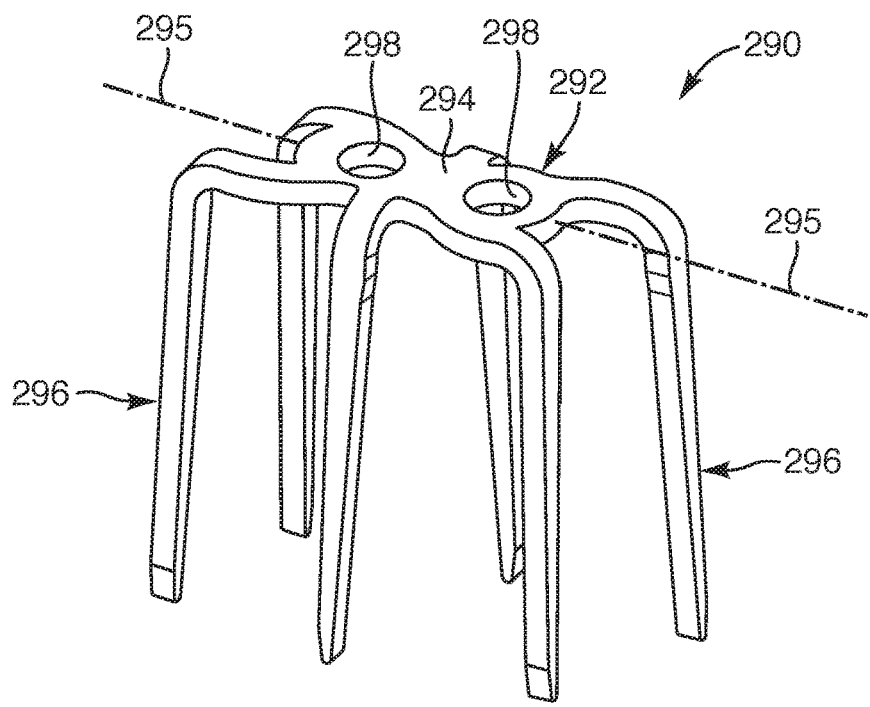
FIG. 21 is a perspective view of another embodiment of an anchor member of a repair device, according to the present invention.

With reference to FIG. 21, another embodiment of an anchor 292 of a repair device 290 is provided. The anchor 292 of this embodiment may be employed with a corresponding capture member, similar to that set forth in previous embodiments. The anchor 292 may also be employed alone or with a capture member, similar to previous embodiments. The anchor 292 of this embodiment may include a base 294 from which legs 296 may extend, such as six legs. In another embodiment, the anchor 292 may include at least four legs 296. In another embodiment, the anchor 292 may include at least five legs 296. The base 294 may include an elongated profile defining an axis 295 along the elongated profile such that the legs 296 may extend substantially perpendicular relative to the axis 295. The legs 296, as in previous embodiments, may be sized and configured to engage anvil buckets to move to a curled position that may wrap around portions of a capture member. In this embodiment, the base 294 may include one or more apertures 298, such as two apertures, extending through the base 294. Such apertures 298 may be sized and configured to extend one or more filaments therethrough for coupling the anchor 292 to a bone anchor. In this manner, upon the anchor 292 being coupled to soft tissue as set forth in previous embodiments, the anchor 292 and soft tissue may be coupled to a bone anchor via the one or more filaments extending through the one or more apertures 298 and being coupled to the anchor 292.

Figure 22:
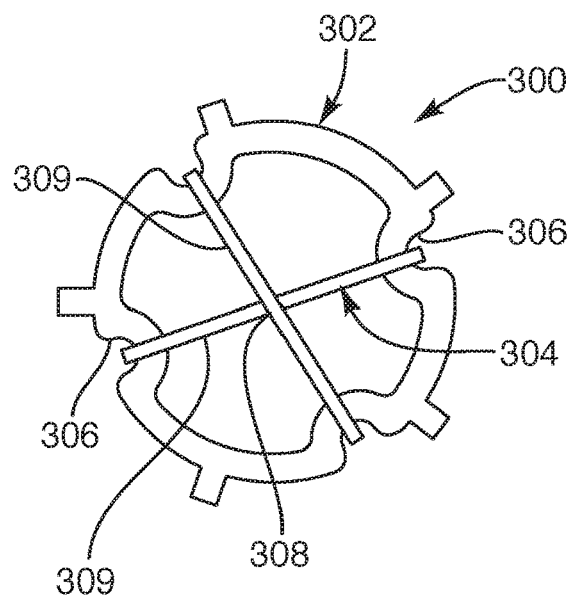
FIG. 22 is a top view of another embodiment of an anchor member of a repair device, depicting one or more flexible members coupled to the anchor member, according to the present invention.
Figure 23:
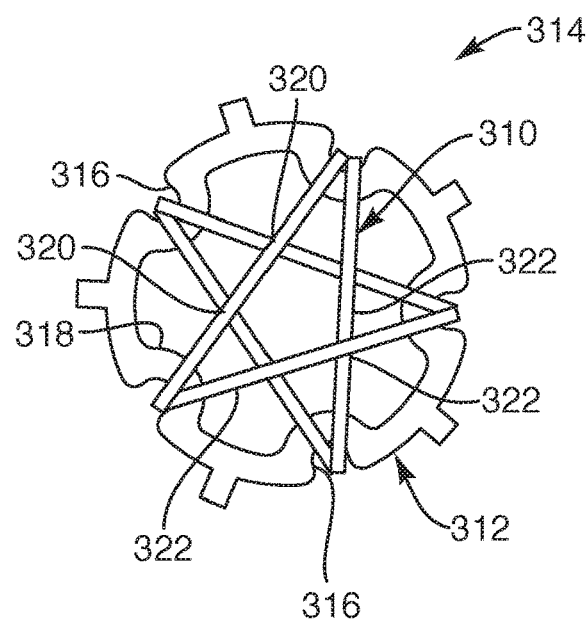
FIG. 23 is a top view of another embodiment of an anchor member of a repair device, depicting one or more flexible members coupled to the anchor member, according to the present invention.
Figure 24:
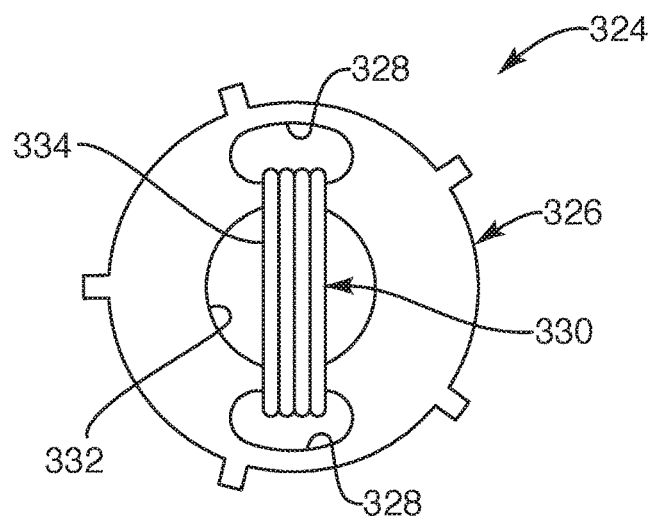
FIG. 24 is a top view of another embodiment of an anchor member of a repair device, depicting one or more flexible members coupled to the anchor member, according to the present invention.

Now with reference to FIGS. 22, 23 and 24, other embodiments of one or more flexible members coupled to a repair device and extending with various configurations, are provided. With respect to FIG. 22, the repair device may include an anchor member 300 similar to the anchor member depicted in FIG. 1, such that a base 302 of the anchor member 300 may include a similar top view profile. In this embodiment, a flexible member 304 may be coupled to the base 302 such that the flexible member 304 may extend between opposing recesses 306 defined in the base 302 so that the flexible member 304 extends in a crisscross manner to define an intersection 308 between length portions 309 of the flexible member 304. As previously set forth, a second flexible member 60 (FIG. 3) may then be passed over the intersection 308 of the flexible member 304 and extend downward from the flexible member 304 and the repair device. Further, as previously set forth, the suture may be coupled to a bone anchor (not shown), similar to that set forth herein.

With respect to FIG. 23, a flexible member 310 may be wrapped around a base 312 of an anchor member 314 to exhibit a star-like configuration. In this embodiment, the anchor member 314 may include multiple recesses 316 defined in the base 312, such as five recesses formed in a periphery of the base 312. With this arrangement, the flexible member 310 may extend across an expanse of a central opening 318 of the base 312 to crisscross at multiple locations to exhibit multiple intersections 320 of multiple length portions 322 of the flexible member 310. With this arrangement, the second flexible member (FIG. 3) may be coupled to the flexible member 310 to extend over one or more length portions 322 of the flexible member 310 at one or more intersections 320 of the flexible member 310.

With respect to FIG. 24, an anchor member 324 may include a base 326 with two apertures 328 or recesses defined therein. In this embodiment, a flexible member 330 may be wrapped through the apertures 328 so that the flexible member 330 extends between the two apertures 328 and over and under a central opening 332 defined in the base member 326 of the anchor member 324. With this arrangement, a second flexible member 60 (FIG. 3) may be coupled to a length portion 334 of the flexible member 330 by extending over the length portion 334 of the flexible member 330 and extending downward from the central opening 332 defined in the anchor member 324. In this manner, the various configurations of the flexible member (as depicted in FIGS. 22, 23 and 24) coupled to the anchor member of the repair device may be employed as a coupling for a second flexible member 60 (FIG. 3) to couple to the repair device and to a bone anchor, similar to that described in other embodiments herein.

Figure 25:
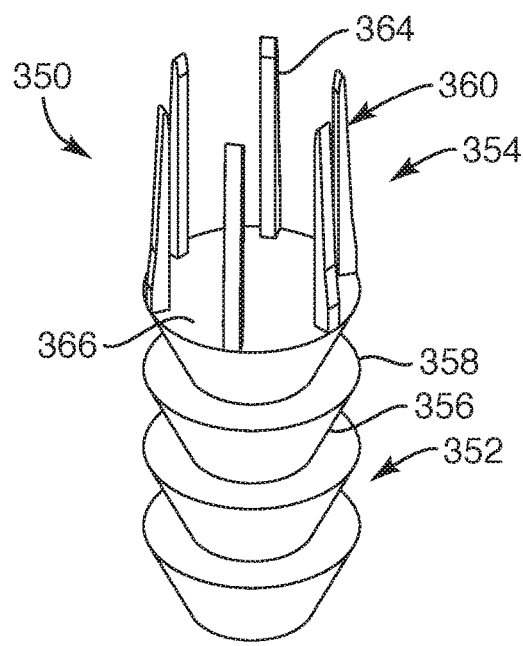
FIG. 25 is a perspective view of another embodiment of a repair device, depicting the repair device having a bone anchor portion with legs in an unformed first state, according to the present invention.
Figure 26:
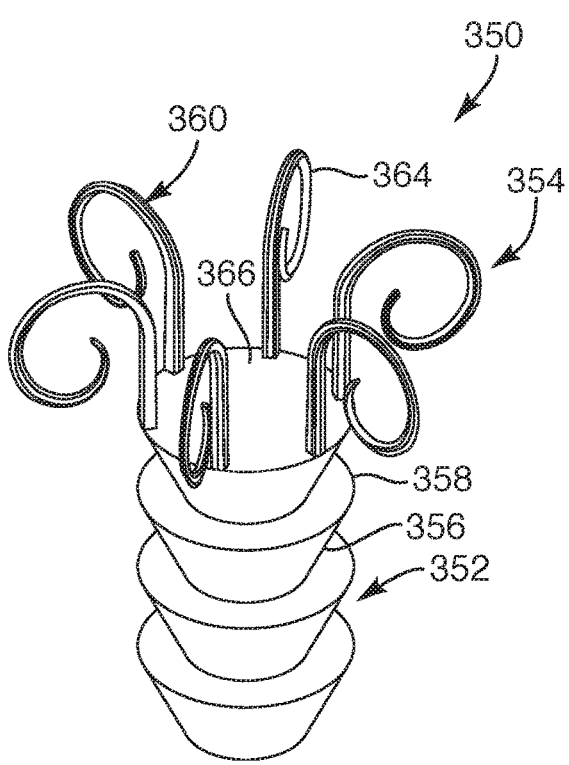
FIG. 26 is a perspective view of the repair device of FIG. 25, depicting the legs extending from the bone anchor portion in a formed second state, according to another embodiment of the present invention.
Figure 27:
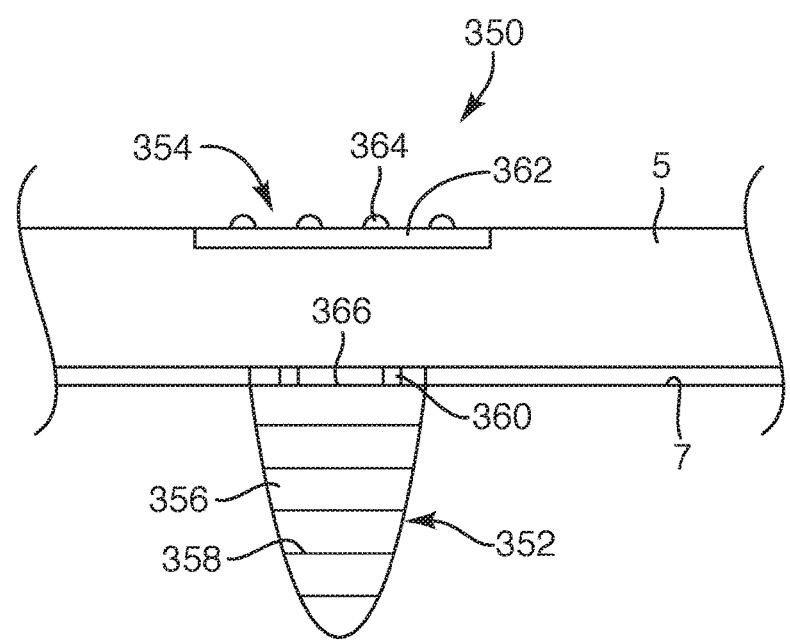
FIG. 27 is a simplified side view of the repair device of FIG. 26, depicting the bone anchor portion seated in bone with the legs coupled to soft tissue, according to another embodiment of the present invention.

Now with reference to FIGS. 25, 26 and 27, another embodiment of a repair device 350 is provided. In this embodiment, the repair device 350 may include a bone anchor portion 352 and a soft tissue anchor portion 354. The bone anchor portion 352 may be sized and configured couple to bone 7. The bone anchor portion 352 may include an outer surface 356 that defines ribs 358 or threads or the like sized and configured to couple to a base structure embedded in the bone or structure that effectively engages the bone 7 itself. Further, various bone cements may also be employed and other structures and procedures for ensuring strong connection of the bone anchor portion 352 in the bone 7, as known to one of ordinary skill in the art.

The soft tissue anchor portion 354 of the repair device 350 may include an anchor 360 and a capture member 362. The anchor 360 may include multiple legs 364 extending from a proximal side 366 or surface of the bone anchor portion 352. Such legs 364 may be embedded within the bone anchor portion 352 during, for example, a molding process of forming the bone anchor portion 352. The legs 364 may be moved from a first position to a second position, the first position being a linear elongated position (FIG. 25) and the second position being a curled position (FIG. 26). The legs 364 of the anchor 360 may include structural characteristics similar to legs 364 of previous embodiments set forth herein that may facilitate consistent movement of the legs 364 to the curled position, upon engaging anvil buckets of an anvil (not shown). The capture member 362 of the soft tissue anchor portion 354 may include, for example, structure to facilitate the legs 364 to curl around as well as provide stability for coupling to soft tissue 5, similar to previous embodiments utilizing a capture member with an anchor. Further, similar to previous embodiments set forth herein, the capture member 362 may be positioned on an anvil with corresponding sizing relative to the capture member 362 so that the legs 364 may be pushed against anvil buckets defined in the anvil to move the legs 364 in the curled position to wrap around structure defined in the capture member 362. In this manner, the bone anchor portion 352 may be coupled to bone 7 and the soft tissue anchor portion 354 may be coupled to soft tissue 5, such as tendon or ligament, for coupling soft tissue 5 to bone 7.

Figure 28:
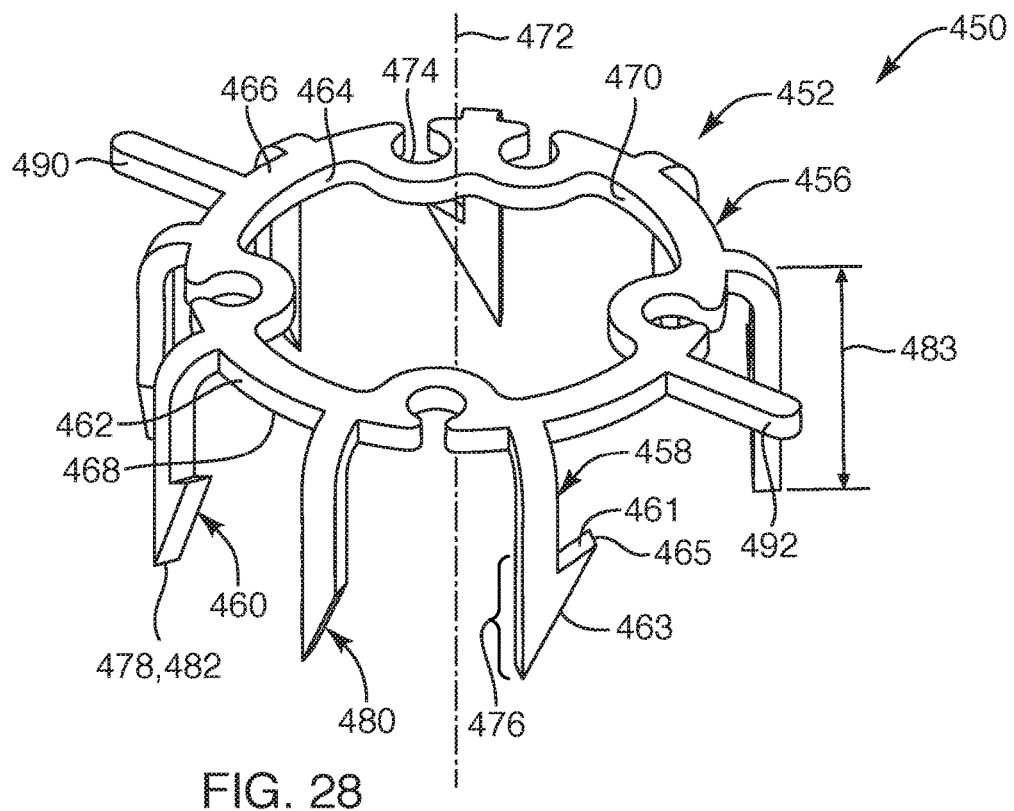
FIG. 28 is a perspective view of another embodiment of a repair device, depicting some of legs of the repair device having barbs, according to the present invention.
Figure 28A:
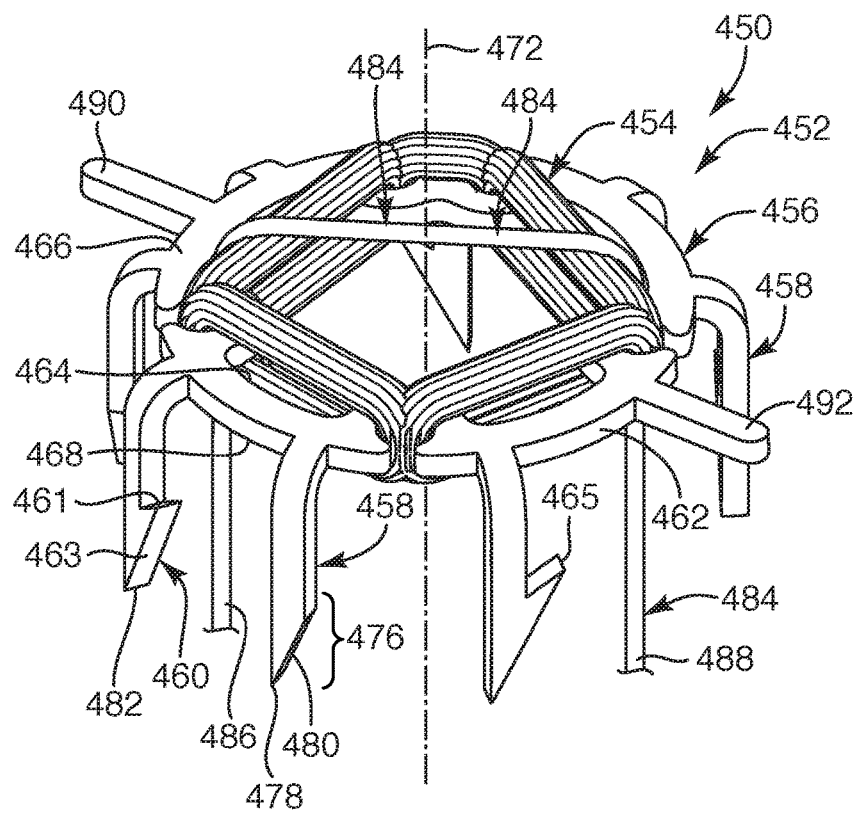
FIG. 28A is a perspective view of the repair device of FIG. 28, depicting the repair device having a flexible member and a flexible element coupled to the repair device, according to another embodiment of the present invention.

Now with reference to FIGS. 28 and 28A, another embodiment of a repair device 450 or a tissue fixating device for fixating to soft tissue is provided. As in previous embodiments, the repair device 450 may include an anchor member 452 and a flexible member 454. The anchor member 452 may include a base 456 with legs 458 extending from the base 456. In this embodiment, the repair device 450 may be delivered without an anvil such that the legs 458 may be maintained in a single fixed position or orientation (without being curled within tissue and/or being wrapped around a back plate or capture plate, as set forth in previous embodiments). In this manner, maintained in a single fixed position or orientation means that the legs 458 of the anchor member 452 remain in the same position prior and subsequent to being delivered into soft tissue. For example, in this embodiment, the legs 458 may be shorter than in previous embodiments, sized and configured to extend into soft tissue without extending completely through or out an opposing side of the soft tissue. Further, some or all of the legs 458 may include a barb 460 sized and configured to substantially prevent migration from the soft tissue. Such barb 460 may extend upward from a given leg 458 with first and second upward extending surfaces 461, 463 to an edge 465, the barb sized and configured to assist in fixating the repair device to soft tissue.

Similar to previous embodiments, the base 456 may extend with a generally circular configuration or any other suitable configuration. The generally circular configuration may also mean a generally oval configuration. The base 456 may define a substantially flat profile with upper and lower sides being planar. Such base 456 may extend to define an outer periphery 462 and an inner periphery 464 each extending between an upper surface 466 and an underside surface 468, the outer periphery 462 defining a generally circular profile. The base 456 may define a central opening 470 defined by the inner periphery 464 of the base 456. Further, the base 456 may define an axis 472 or central axis of the repair device 450 such that the axis 472 may extend centrally through the central opening 470 of the base 456. In one embodiment, the axis 472 may extend parallel relative to a surface of the outer periphery 462 and inner periphery 464 of the base 456. Further, the axis 472 may extend perpendicular relative to the upper and underside surfaces 466, 468 of the base 456.

Further, similar to previous embodiments, the base 456 may include multiple recesses 474 defined therein, the recesses 474 sized and configured to receive the flexible member 454 coupled to the base 456. For example, the recesses 474 may be defined in the outer periphery 462 of the base 456 and extend into the upper and underside surfaces 466, 468 of the base 456. As in previous embodiments, the flexible member 454 may be formed from one or more filaments. Such one or more filaments may be wound or wrapped around the base 456 through the recesses 474 with multiple windings so as to form the flexible member 454.

As set forth, the base 456 of the anchor member 452 may include multiple legs 458 extending downward from the base 456 and integrally formed with the base 456. For example, the legs 456 may extend from the outer periphery 462 of the base 456, extending radially from the outer periphery 462 and then extending downward relative to the underside surface 468 and may extend substantially parallel relative to the axis 472. Further, after the legs 458 extend radially directly from the base 456, the legs 458 may extend substantially straight with an elongated structure so as to extend substantially perpendicular relative to the underside surface 468 of the base 456. The legs 458 may each include an end portion 476 that may extend to a free end 478, the end portion 476 extending with a tapered portion 480 such that the free end 478 extends with a surface edge 482. As previously set forth, some of the legs 458 may include the barb 460. For example, the barb 460 may extend upward and away from along a length 483 of one of the legs 458 such as extending upward from the end portion 476 of the legs 458. Further, some of the legs 458 that do not include the barb 460 may extend downward with the tapered portion 480 and surface edge 482 along the end portion 476. In one embodiment, the anchor member 452 may include at least four legs 458.

As in previous embodiments, the repair device 450 may be employed to fixate to soft tissue and be coupled to a flexible element 484, such as a suture. The flexible element 484 may be elongated and may be employed to extend and couple to the flexible member 454 and to couple to a bone anchor, such as that depicted in FIGS. 14, 15 and 16 (see also FIGS. 40-45). For example, the flexible element 484 may extend over the flexible member 454 for coupling thereto such that the flexible element 484 may extend downward from the flexible member 454 with a first portion 486 and a second portion 488. Such first and second portions 486, 488 of the flexible element 484 may be coupled to a bone anchor (not shown), similar to the suture coupled to the bone anchor depicted and described in FIGS. 14, 15 and 16 (see also FIGS. 40-45). In another embodiment, the flexible element 484 may couple directly to the base 456 of the anchor member 452 and/or base portions of the legs 458 along the base 456, as depicted, for example, in FIG. 40.

The repair device 450 of this embodiment may be delivered with a delivery device (not shown) such that the flexible element 484 may be pre-loaded and coupled to the flexible member 454. The repair device 450 may be positioned with the delivery device such that the legs 458 may be forced into soft tissue by placing a force against the upper surface 466 of the base 456, the legs 458 maintaining a fixed position and the barbs 460 substantially preventing the repair device 450 from migrating from the soft tissue. The flexible element 484 may also be coupled to the bone anchor, the bone anchor fixated to the bone and the first and second portions 486, 488 of the flexible element 484 synched taught to pull the soft tissue and the repair device 450 adjacent the bone anchor. Further, the base 456 may also include first and second extensions 490, 492 that may extend from opposite sides of the outer periphery 462 of the base 456. Such first and second extensions 490, 492 may be employed to assist in holding the repair device 450 upon the repair device being delivered into the soft tissue.

Figure 29:
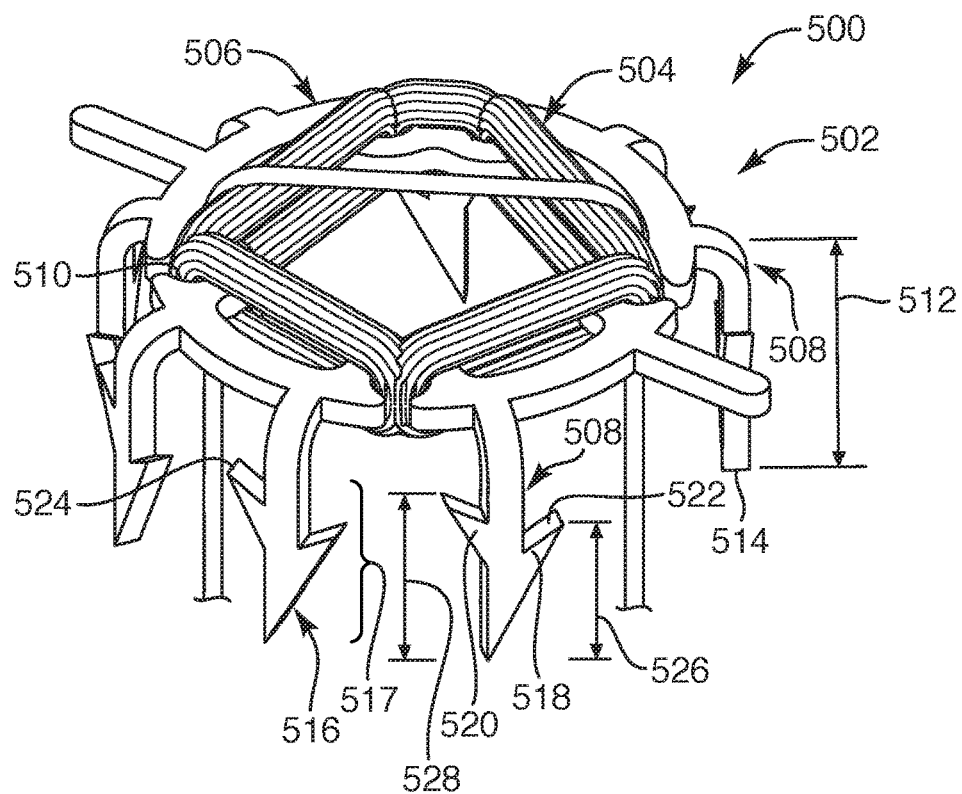
FIG. 29 is a perspective view of another embodiment of a repair device, depicting legs of the repair device having multiple barbs, according to the present invention.

With reference now to FIG. 29, another embodiment of a repair device 500, similar to the embodiment of FIG. 28A, is provided. Similar to the previous embodiment, the repair device 500 may include an anchor member 502 and a flexible member 504, the anchor member 502 having a base 506 with multiple legs 508 extending therefrom and the flexible member 504 coupled to the anchor member 502 with recesses 510 defined in the base. In this embodiment, the multiple legs 508 extending from the base 506 may each extend with a longitudinal length 512 to a free end 514 or free end edge, the legs 508 each extending with multiple barbs 516. For example, each leg 508 may include an end portion 517 or engaging portion along the length 512 of the legs 508. Further, each leg 508 may include a first barb 518 and a second barb 520, the first barb 518 extending upward from the downward extending leg 508 and the second barb 520 extending upward from the downward extending leg 508. In one embodiment, the first barb 518 and the second barb 520 may extend from opposite sides of each leg 508. In another embodiment, the first barb 518 may extend to a first barb edge 522 and the second barb 520 may extend to a second barb edge 524, the first barb edge 522 extending to a first height 526 and the second barb edge 524 extending to a second height 528. The second height 528 may be higher than the first height 526 relative to the free end 514 of each leg 508. In another embodiment, the first height 526 may be similar to the second height 528 relative to the free end 514 of each leg 508. In another embodiment, the first barb 518 and the second barb 520 may extend from a common side of a given leg 508. In another embodiment, some of the legs 508 may include multiple barbs and some of the legs may include a single barb.

Figure 30:
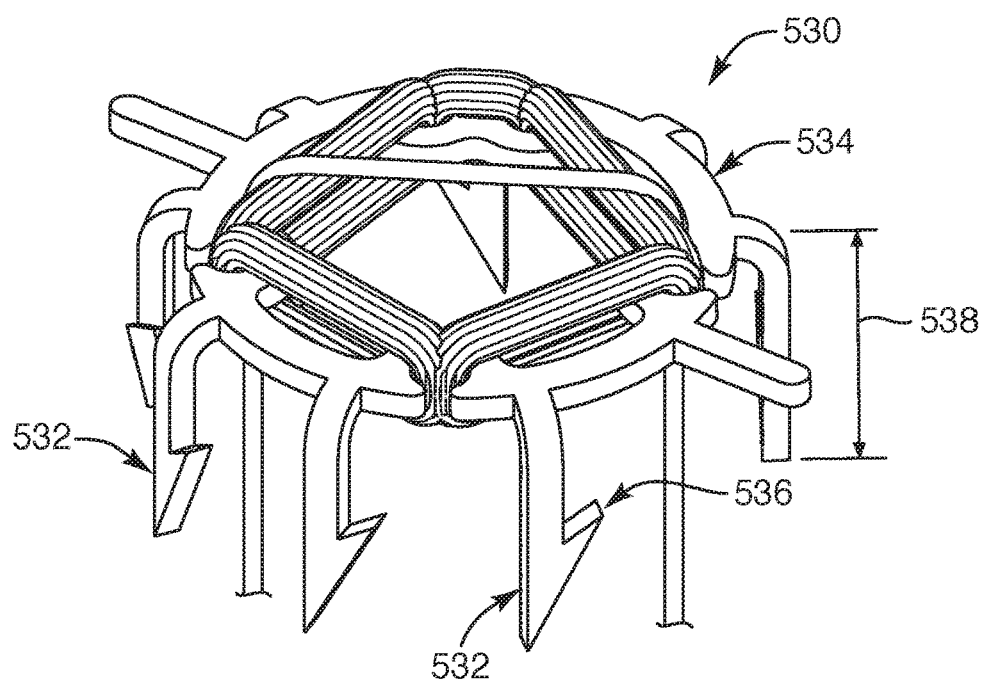
FIG. 30 is a perspective view of another embodiment of a repair device, depicting each of the legs of the repair device having a barb, according to the present invention.
Figure 31:
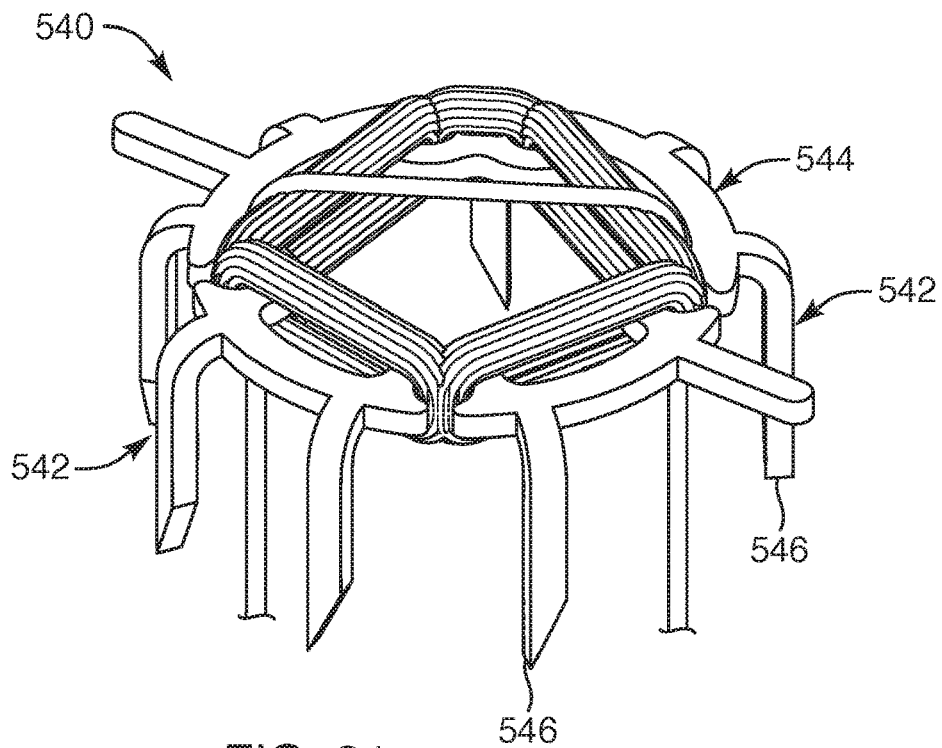
FIG. 31 is a perspective view of another embodiment of a repair device, depicting legs of the repair device without barbs, according to the present invention.

With reference now to FIG. 30, another embodiment of a repair device 530 is provided. This embodiment may be structurally similar to the repair device depicted in FIG. 28A, except in this embodiment, legs 532 extending from a base 534 of the repair device 530 may each include a single barb 536 along a length of the legs 532. In regard to FIG. 31, another embodiment of a repair device 540 is provided. The repair device 540 of this embodiment may also be structurally similar to the repair device of FIG. 28A, except legs 542 of the repair device 540 of this embodiment may not include barbs. As in previous embodiments, the legs 542 may extend downward from a base 544 with an end portion 546 and a free end 548 along a length of the legs 542, the free end sized and configured to engage soft tissue so that the repair device 540 may be fixated to soft tissue.

Figure 32:
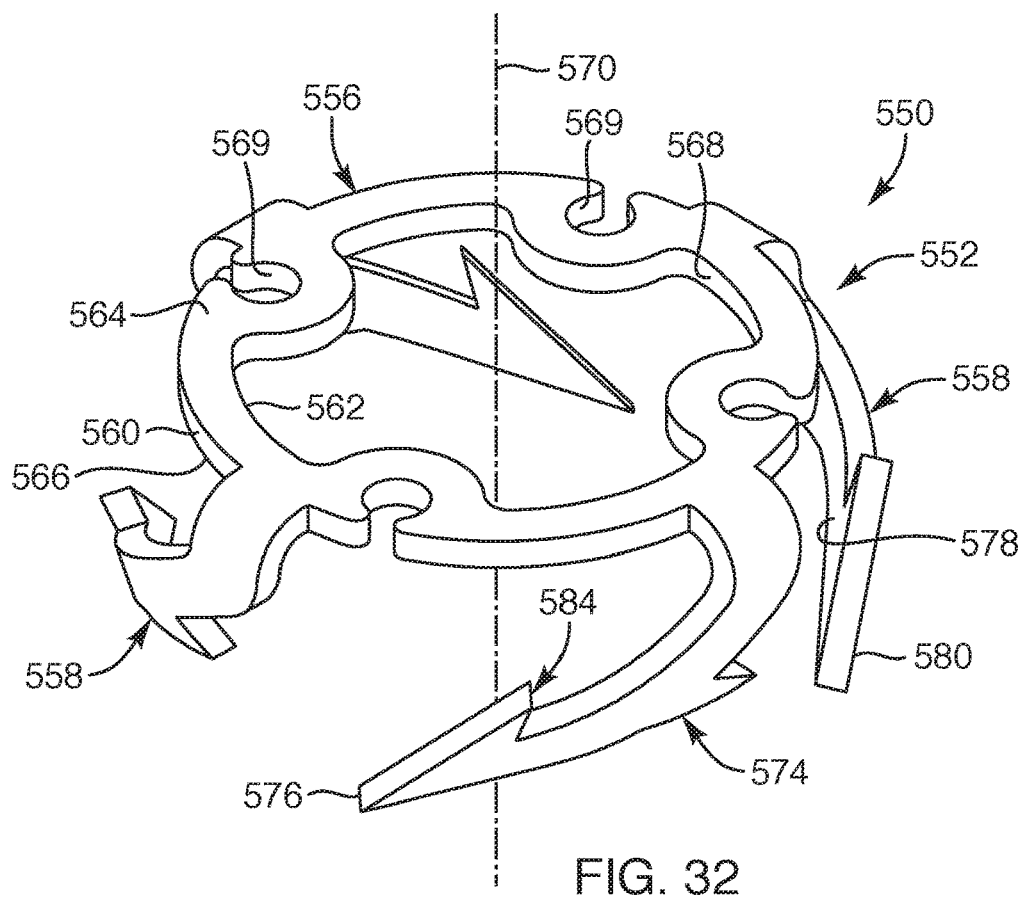
FIG. 32 is a perspective view of another embodiment of a repair device, depicting legs of the repair device extending downward and transverse, according to the present invention.
Figure 32A:
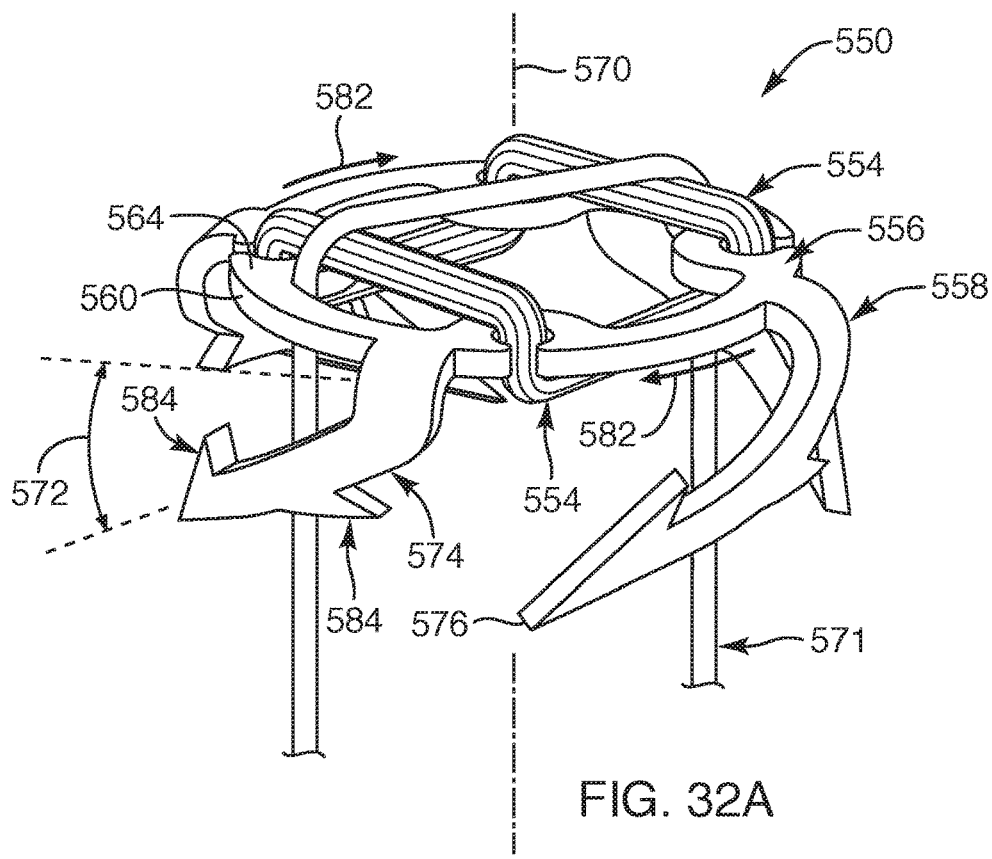
FIG. 32A is a perspective view of the repair device of FIG. 95, depicting the repair device having a flexible member and a flexible element coupled to the repair device, according to another embodiment of the present invention.

Now with reference to FIGS. 32 and 32A, another embodiment of a repair device 550 or tissue fixating device is provided. In this embodiment, the repair device 550 may be employed with a bone anchor similar to that described and depicted relative to FIGS. 28 and 28A and FIGS. 34-39. Similar to previous embodiments, the repair device 550 may include an anchor member 552 and a flexible member 554. The anchor member 552 includes a base 556 and legs 558 extending downward from the base 556, the legs 558 sized and configured to engage soft tissue for fixating the repair device 550 thereto. As in previous embodiments, the base may extend to define a flat profile. The base 556 may include a generally circular profile or configuration or any other suitable configuration, extending to define an outer periphery 560 and an inner periphery 562 defining an axis 570. The outer and inner periphery 560, 562 may extend between an upper surface 564 and an underside surface 566. The upper surface 564 and the underside surface 566 may be planar and extend to the legs 558 and the outer and inner peripheries 560, 562. The inner periphery 562 may define a central opening 568 with the axis 570 or central axis extending centrally through the central opening 568. Further, the base 556 may define multiple recesses 569 therein for coupling the flexible member 554 through the recesses 569 and to the base 556 or anchor member 552, as in previous embodiments. With this arrangement, the repair device 550 may be employed to fixate to soft tissue for tethering the soft tissue to a bone anchor via a flexible element 571, similar to that described and depicted in FIGS. 14, 15 and 16.

As previously set forth, the legs 558 may integrally extend downward from the base 556. Further, as in the embodiments set forth in FIGS. 28-31, the legs 558 may be maintained in a single fixed position. The repair device 550 of this embodiment may include, for example, four legs 558 or more so as to exhibit at least four legs 558. In another embodiment, the repair device 550 may include at least three legs 558. In this embodiment, each leg 558 may extend radially and downward from the outer periphery 560 of the base 556 and then extend downward at an angle 572 relative to the base 556 to extend with an angled portion 574 to a free end 576. In this manner, the elongated length of the angled portion 574 of the legs 558 may be oriented such that the angle 572 of such angled portion of the legs 558 may be less than seventy-five degrees relative to the underside surface 566 of the base and, preferably, the angle 572 may be in the range between about twenty-five degrees and about sixty-five degrees relative to the underside surface 566 of the base 556. The angled portion 574 of each of the legs 558 may extend with an inner surface 578 and an outer surface 580 such that the inner surface 578 extends substantially parallel with the axis 570.

Figure 33:
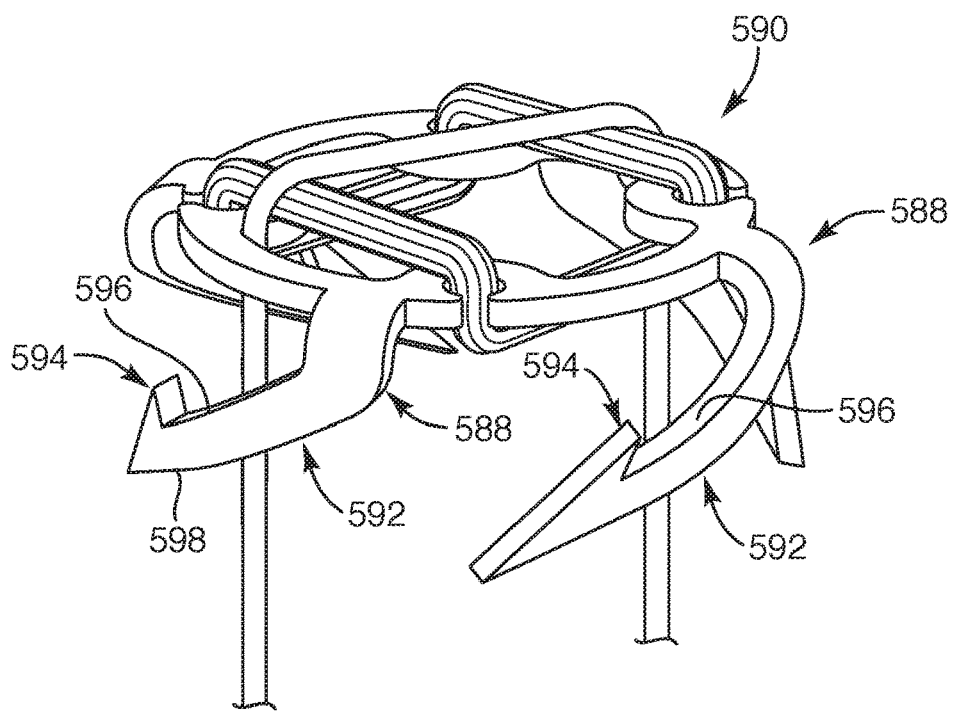
FIG. 33 is a perspective view of another embodiment of a repair device, depicting legs of the repair device having single barbs, according to the present invention.

In one embodiment, each of the legs 558 may extend with the angled portion 574 so that the repair device 550 may be coupled to soft tissue with a rotational force, as shown by arrow 582, so as to rotate about the axis 570 of the repair device 550. In other words, as the free ends 576 of the legs 558 contact tissue while the base 556 is being rotated with a delivery device, such as the delivery device 600 depicted in FIGS. 36-37, the free ends 576 of the legs 558 grab the tissue such that the angled portion 574 of the legs 558 sink and pull the repair device 550 into the soft tissue. Further, in one embodiment, the angled portion 574 of each of the legs 558 may include one or more barbs 584 extending therefrom such that the one or more barbs 584 may substantially prevent reverse rotation of the repair device 550 or migration of the repair device 550 from the soft tissue. In this manner, the barbs 584 may be sized and configured to assist in maintaining the repair device 550 in soft tissue. As depicted in FIG. 33, legs 588 of a repair device 590 may extend with an angled portion 592 having various types of barb configurations. For example, the legs 588 may each include a single barb 594. Such single barb 594 of the legs 588 may extend from an upper side 596 of the angled portion 592 of each leg 588. In another embodiment, the single barb 594 of the legs 588 may extend from an underside 598 of the angled portion 592 of the legs 588.

Now with reference to FIGS. 34-39, a method for fixating a repair device, such as the anchor member 522 of the repair device 550 (described and depicted in FIGS. 32 and 32A), to soft tissue and attaching the soft tissue to bone will now be described. With respect to FIGS. 34 and 35, the repair device 550 may be delivered and fixated to tissue with a delivery device 600. The delivery device 600 may include a shaft 602 extending between a handle (not shown) and an end portion 604 or engagement portion, the delivery device 600 being elongated to define an axis 606 along the length thereof. Each of the handle, the shaft 602 and the end portion 604 of the delivery device may be in a fixed arrangement relative to each other. The shaft 602 may include the handle or grip member at a proximal end thereof, the handle having a sphere like shape so as to be readily handled by the hand of the physician. The end portion 604 may include an abutment portion 608 and an insert portion 610, the insert portion 610 including a key portion 612. The end portion 604 may extend directly from the shaft 602, the shaft 602 having a circular cross-section. The abutment portion 608 may also define a circular cross-section with a larger diameter than the shaft 602. The abutment portion 608 may extend with a distal surface or abutment surface 614 sized and configured to directly contact the top side 616 or proximal side of the repair device 550. The insert portion 610 may extend distal the abutment surface 614 of the abutment portion 608. The insert portion 610 may be sized and configured to be inserted within the central opening 568 defined in the base 556 of the repair device 550. The insert portion 610 may extend distally from the abutment surface 614 to a distal surface 618 or distal side of the delivery device 600. The insert portion 610 may also extend to define the key portion 610 along one or more sides of the insert portion 610. The key portion 612 may also extend through the central opening 568 of the repair device 550. The key portion 612 may extend to define a protrusion or notch or the like, that may be elongated and sized and configured to be captured within the central opening 568 so as to be engagable with the inner periphery 562 of the anchor member 552. For example, the key portion 612 may be an elongated protrusion 620, extending distally from the abutment surface 614 to the distal surface 618. With this arrangement, the end portion 604 of the delivery device 600 may be sized and configured to engage with the anchor member 552 of the repair device 550 for fixating the anchor member 552 to soft tissue.

Figure 34:
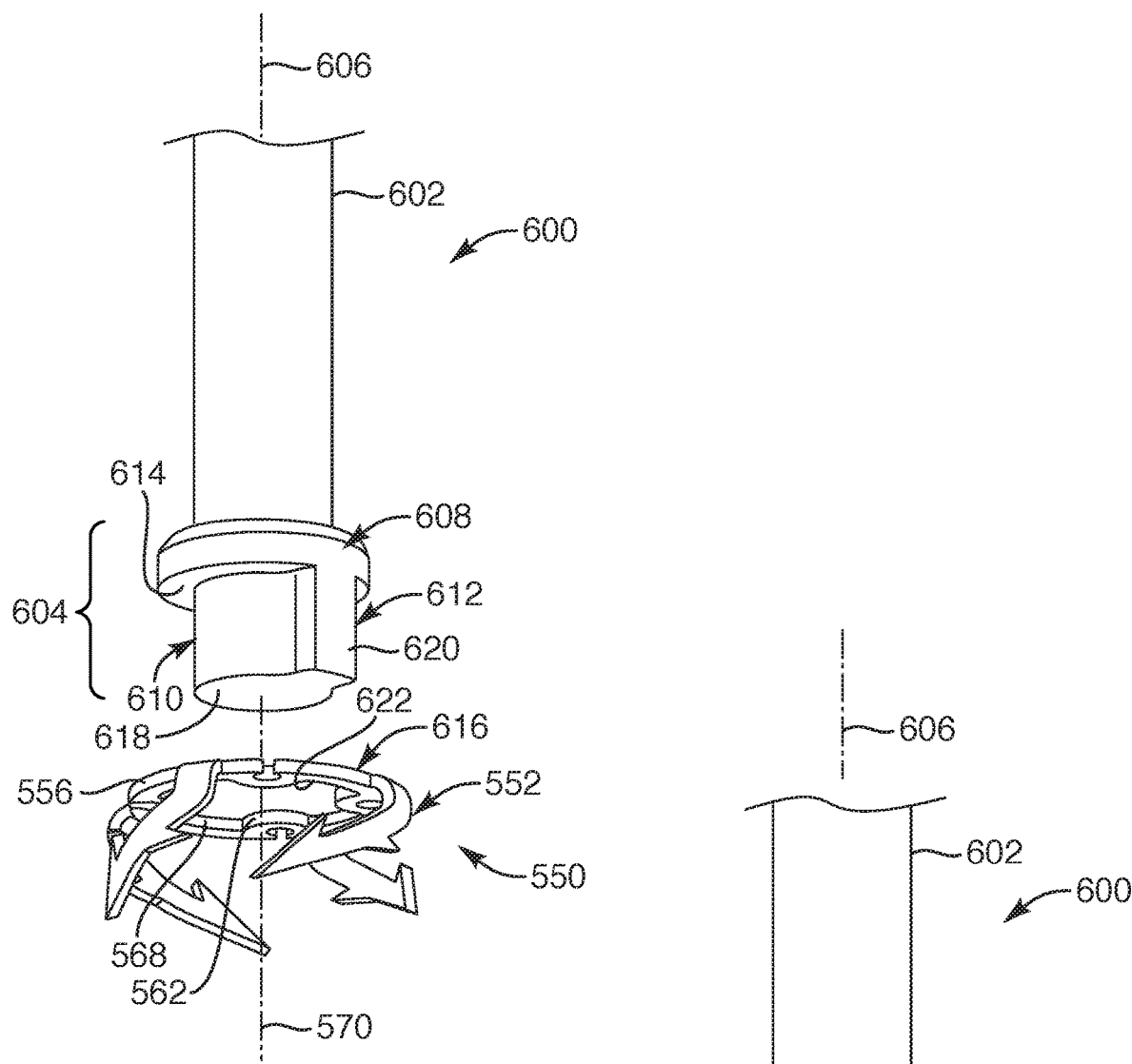
FIG. 34 is a perspective view of the repair device of FIG. 32 associated with a delivery device, according to another embodiment of the present invention.
Figure 35:
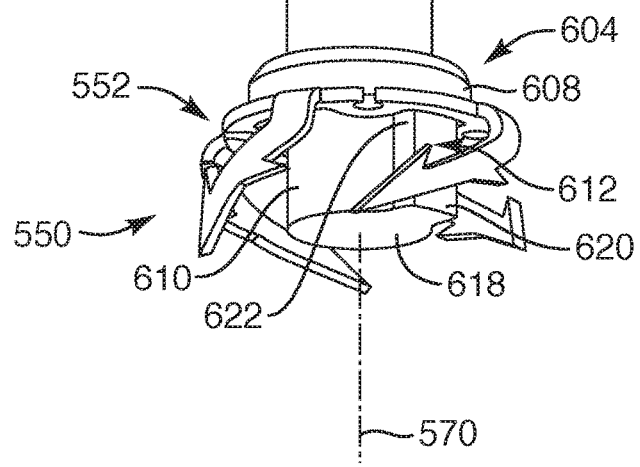
FIG. 35 is a perspective view of the delivery device positioned within a central opening of the repair device, according to another embodiment of the present invention.

To fixate the anchor member 552 to soft tissue, the anchor member 552 may be coupled to the delivery device 600. The anchor member 552 may be pre-assembled to the delivery device 600 or the physician may assemble the anchor member 552 to the delivery device 600. Such assembly may be employed by aligning the axis 606 of the delivery device 600 with the central axis 568 of the anchor member 552 and inserting the insert portion 610 through the central opening 568 of the anchor member 552 on a proximal side thereof, as depicted in FIGS. 34 and 35. Further, the key portion 612 may be aligned and correspond with a keyed structure 622, such as a notch or the like, defined along the inner periphery 562 defining the central opening 568 of the anchor member 552. Upon fully inserting the insert portion 610 through the central opening 568, the abutment surface 614 may directly contact the top side 616 of the anchor member 552 and/or the flexible member 554 (FIG. 32A). Such anchor member 552 may be held to the end portion 604 of the delivery device 600 with an interference fit or with clips or the like. With the anchor member 552 positioned on the end portion 604 of the delivery device 600, the anchor member 552 may be prepared for fixating to soft tissue.

Figure 36:
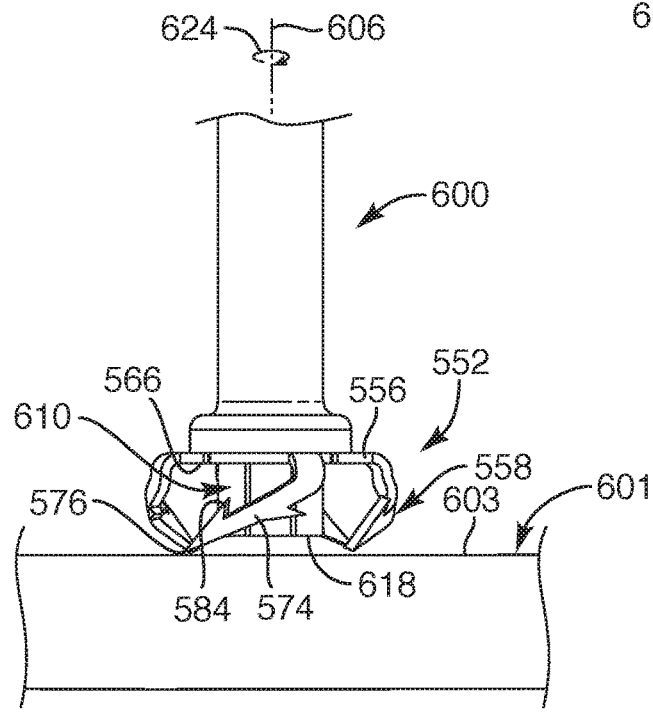
FIG. 36 is a side view of the delivery device engaged with the repair device, depicting the repair device positioned on soft tissue prior to rotating the delivery device, according to another embodiment of the present invention.
Figure 37:
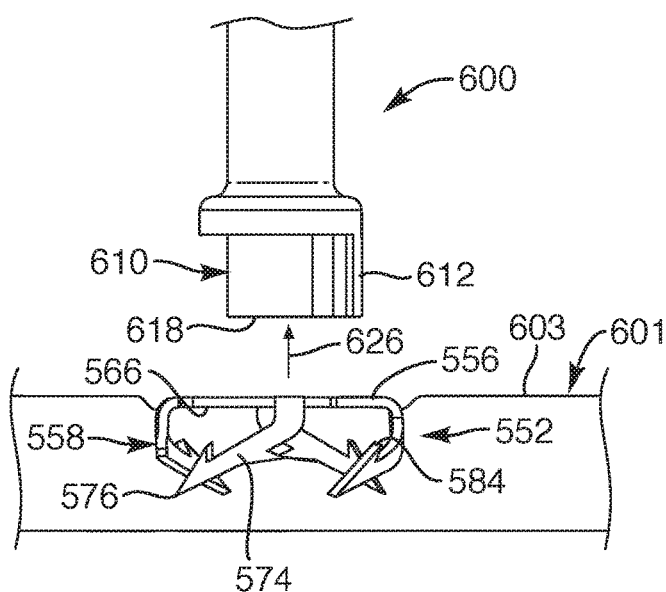
FIG. 37 is a side view of the repair device fixated to soft tissue subsequent to rotating the delivery device, depicting the delivery device withdrawn from the repair device, according to another embodiment of the present invention.

Now with reference to FIGS. 36 and 37, to fixate the anchor member 552 to soft tissue 601, the physician may position the free ends 576 or tips of the legs 558 of the anchor member 552 directly onto an upper surface 603 of the soft tissue 601 with enough pressure or force so that a distal surface 618 of the insert portion 610 of the delivery device 600 contacts or sits just above the soft tissue 601. The physician may then rotate the delivery device 600 by rotating the handle (not shown) so that the insert portion 610 rotates about the axis 606, as indicated by rotational arrow 624. Upon such rotation of the insert portion 610, the key portion 612 of the insert portion 610 may also laterally engage the keyed structure 622 defined in the inner periphery 562 (see FIG. 34) of the anchor member 552 to, therefore, rotate the anchor member 552. In this manner, the key portion 612 facilitates rotation of the anchor member 552 upon rotating the delivery device 600 about the axis 606. Further, upon such rotation of the anchor member 552, the legs 558 of the anchor member 552 may be substantially fixed at an angle 572 (FIG. 32A) so as to extend with the angled portion 574 so that free ends 576 of each of the legs 558 grab the soft tissue 601 and pull the soft tissue upward along the angled portion 574 of the legs 558 so as to sink the legs 558 of the anchor member 552 into the soft tissue 601. Otherwise said, as the physician manually rotates the delivery device 600, the distal surface 618 may contact the upper surface 603 of the soft tissue 601 while the legs 558 of the anchor member 552 rotatably sink into the soft tissue 601. As such, upon fully sinking the anchor member 552 into the soft tissue 601, the insert portion 610 may be pushed out of the central opening 568 of the anchor member 552, as indicated by arrow 626, or rather, the anchor member 552 pulls itself off the insert portion 610 of the delivery device 600 as the upper surface 603 of the soft tissue 601 abuts the underside surface 566 of the base 556 of the anchor member 552. The physician may recognize that the anchor member 552 is fully anchored so as to rotatably sink into the soft tissue 601 once the insert portion 610 is pushed out of the central opening 568 of the anchor member 552. Further, the one or more barbs 584 along the angled portion 574 of the legs 558 substantially prevent the anchor member 552 from becoming dislodged from the soft tissue 601.

Figure 38:
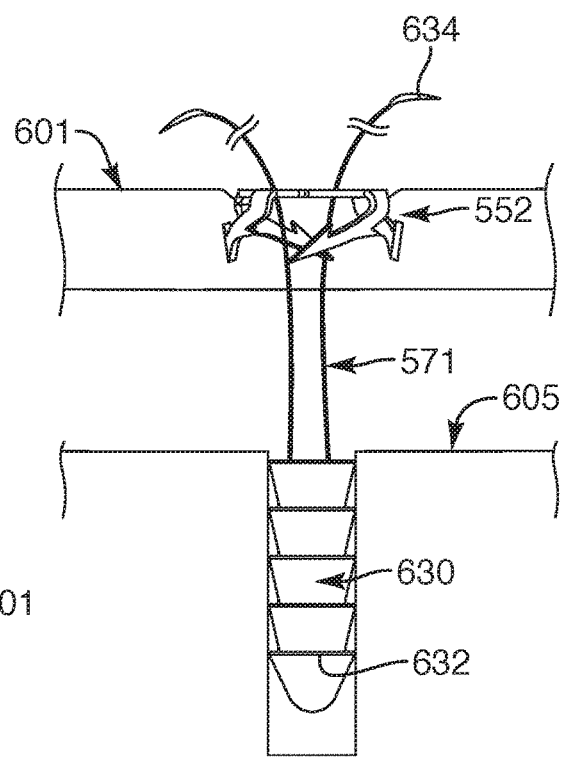
FIG. 38 is a side view of the repair device fixated to soft tissue and a bone anchor anchored to bone, depicting a flexible member coupled to the bone anchor and extending through the central opening of the repair device, according to another embodiment of the present invention.
Figure 39:
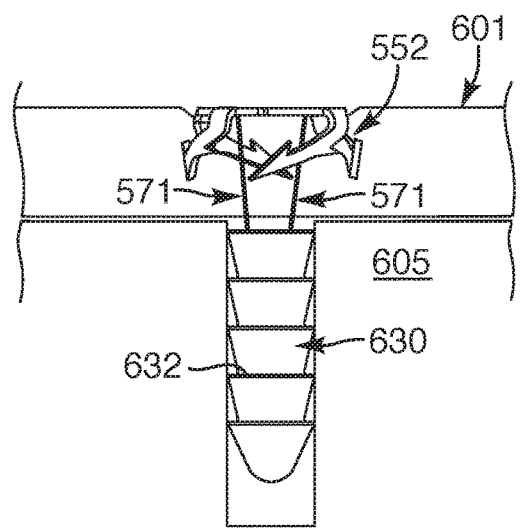
FIG. 39 is a side view of the repair device fixated to soft tissue coupled to the bone anchor fixated in bone, depicting the soft tissue cinched to the bone with the flexible member extending tautly between the repair device and the bone anchor, according to another embodiment of the present invention.

Now with reference to FIGS. 38 and 39, the physician may attach the anchor member 552 fixated to soft tissue 601 to a bone anchor 630 implanted into bone 605 with a flexible element 571 (see FIG. 32A), such as one or more sutures or the like. The bone anchor 630 may be implanted into the bone 605 prior or subsequent to fixating the anchor member 552 to the soft tissue 601, as set forth above. The bone anchor 630 may be an elongated structure with ribs 632 or windings along an external surface thereof. The bone anchor 630 may include coupling structure (not shown) for coupling to the flexible element 571. Such flexible element 571 may be coupled to the bone anchor 630 prior to implanting the bone anchor 630 or the flexible element 571 may be coupled to the bone anchor 630 subsequent to implanting the bone anchor 630. For example, the flexible element 571 may be coupled to the bone anchor 630 in a knotless arrangement using various knotless bone anchor techniques as known to one of ordinary skill in the art. The flexible element 571 may include suture needles 634 at ends of the flexible element 571. As depicted in FIG. 38, ends of the flexible element 571 may be threaded through the soft tissue 601 and through the central opening 568 (see FIGS. 32 and 32A) of the anchor member 552. The physician may wrap the flexible element 571 around, for example, the flexible member 554 (FIG. 32A) of the repair device 550 or around the base 556 of the anchor member 552. In another embodiment, the flexible element 571 may be coupled around base portions of the legs 558 and/or around the base 556 of the anchor member 552 to engage the outer and/or inner peripheries of the base 556. The physician may then synch down the anchor member 552 over the bone anchor 630 so that the soft tissue 601 is directly against and over the bone anchor 630 and bone 605. In another embodiment, the anchor member 552 may be synched down off-set relative to the bone anchor 630. The physician may then tie-off the flexible element 571 and remove/snip remaining unused portions of the flexible element 571 such that the flexible element 571 is left in a taut state, as depicted in FIG. 39, using various suture techniques as known to one of ordinary skill in the art. In this manner, the anchor member 552 may be fixated to soft tissue 601 so that the soft tissue may be synched down against the bone 605 so that the soft tissue 601 can eventually attach itself and heal against the bone 605. The above-described method of fixating soft tissue to bone may also be employed for the repair device 590, depicted in FIG. 33.

Referencing FIGS. 40-45, another embodiment of a method for fixating soft tissue to bone is provided. With respect to FIG. 40, in one embodiment, a repair device 640 employed for fixating soft tissue may exhibit an anchor member 642 similar to the repair device 540 of FIG. 31, except the repair device 640 of this embodiment may exhibit fewer legs 644 and may include a flexible member 646 that may wrap around portions of the anchor member 642 (that may be implemented similar to previous embodiments) such that the flexible member 646 may extend downward to couple to a bone anchor 670 (FIG. 42A). In one embodiment, the repair device 640 may include at least four legs 644. In another embodiment, the repair device 640 may include at least three legs 644. For example, the anchor member 642 may include a base 648 with the legs 644 extending downward from the base 648, the base 648 defining a central opening 650 therein that may define a central axis 652. Such legs 644 may also include one or more barbs associated with some or all of the legs 644, as set forth in previous embodiments of the repair device set forth herein. In one embodiment, the flexible member 646 may be a single suture. In another embodiment, the flexible member 646 may be one or more sutures. In another embodiment, the flexible member 646 may extend with one or more filaments. In another embodiment, the flexible member 646 may be coupled to the base 648 by wrapping around portions of the legs 644 with first and second portions 654, 656 extending downward from a distal side of the anchor member so as to extend through the central opening 650 of the anchor member 642 to extend to first and second ends 658, 660 of the flexible member 646. In another embodiment, the first and second ends 658, 660 of the flexible member 646 may include respective first and second suture needles 662, 664. In one embodiment, the flexible member 646 may be pre-assembled with the anchor member 642. In another embodiment, a flexible member 646 may be subsequently fixated to the anchor member 642 by a physician, similar to that described and depicted in FIGS. 38 and 39.

Figure 40:
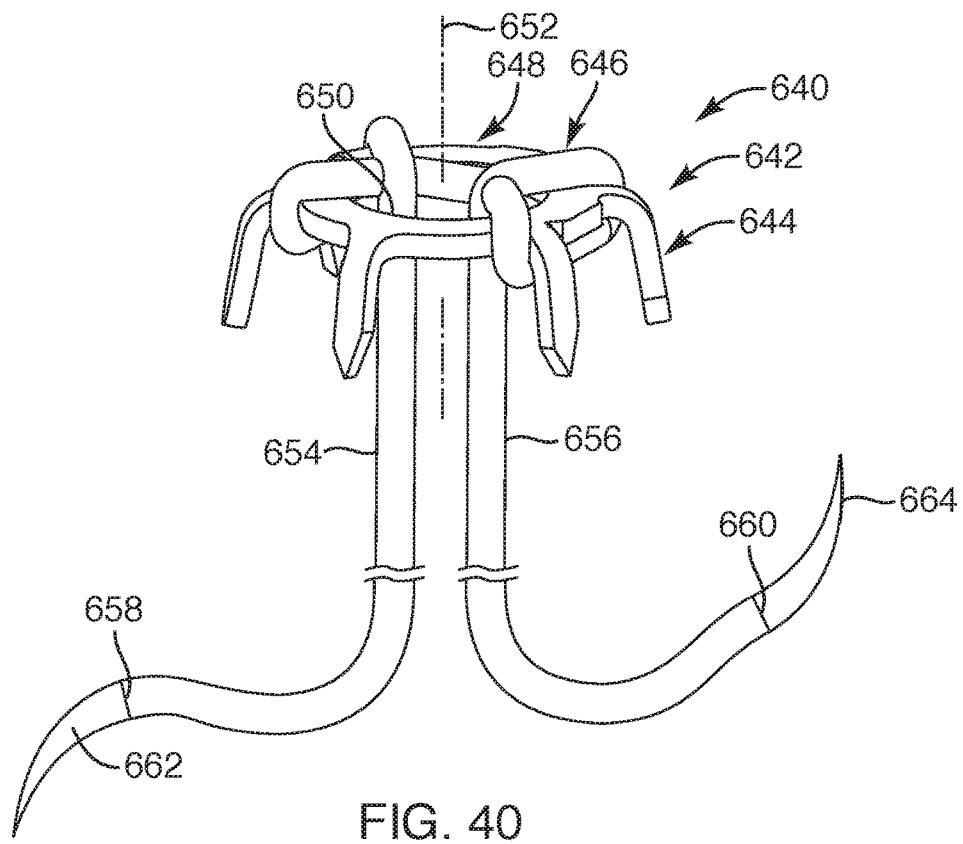
FIG. 40 is a perspective view of another embodiment of a repair device with a flexible member coupled to the repair device, according to the present invention.
Figure 41:
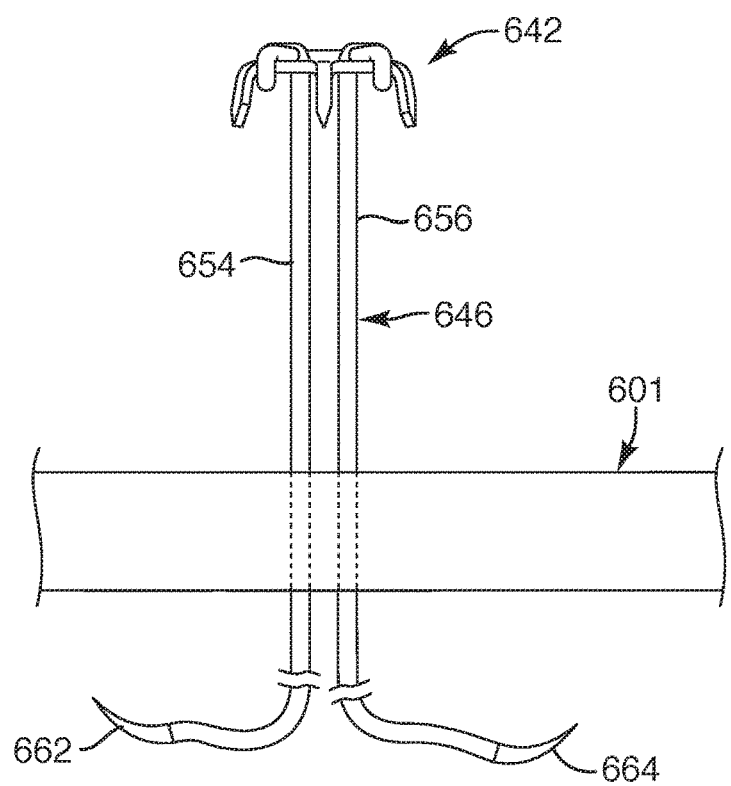
FIG. 41 is a side view of the repair device of FIG. 40, depicting ends of the flexible member extending through soft tissue, according to another embodiment of the present invention.

Now with reference to FIGS. 40 and 41, one step for fixating the anchor member 642 to soft tissue 601 may be threading the first and second needles 662, 664 of the flexible member 646 through the soft tissue 601. Such threading of the first and second portions 654, 656 may be inserted through the soft tissue 601 in close proximity to each other and in a region of the soft tissue 601 that the physician desires for the soft tissue 601 to be positioned against bone (not shown). Further, such threading of the flexible member 646 through the soft tissue 601 may be implemented with the first and second suture needles 662, 664, as depicted, and/or by employing a suture passer or a delivery instrument.

With reference to FIGS. 42 and 42A, another step for fixating the anchor member 642 and soft tissue 601 to bone may include engaging first and second portions 654, 656 of the flexible member 646 with a bone anchor 670. For example, the bone anchor 670 may include coupling structure, such as a laterally extending hole 672 (as shown with dashed line) and opposing first and second elongated notches 674, 676 defined in the bone anchor 670. Such first and second elongated notches 674, 676 may extend from opposing ends of the laterally extending hole 672 so as to extend parallel relative to each other and with a bone anchor axis 678. With this arrangement, the first portion 654 of the flexible member 646 may extend along the first elongated notch 674 and through the laterally extending hole 672 so as to extend therethrough. Similarly, the second portion 656 of the flexible member 646 may extend along the second elongated notch 676 and through the laterally extending hole 672 and out the opposite side of the bone anchor 670. Such first and second elongated notches 674, 676 may extend from or adjacent to a top surface of the bone anchor 670 to the laterally extending hole 672. The laterally extending hole 672 may be positioned along an elongated length of the bone anchor 670, such as a mid-portion of the bone anchor 670, and may extend between opposite sides of the bone anchor 670. With this arrangement, the first and second portions 654, 656 of the flexible member 646 may be engaged with the bone anchor 670 in a pre-anchoring state. In this pre-anchoring state, the first and second portions 654, 656 of the flexible member 646 may be freely pulled through the laterally extending hole 672 of the bone anchor 670.

Figure 44:
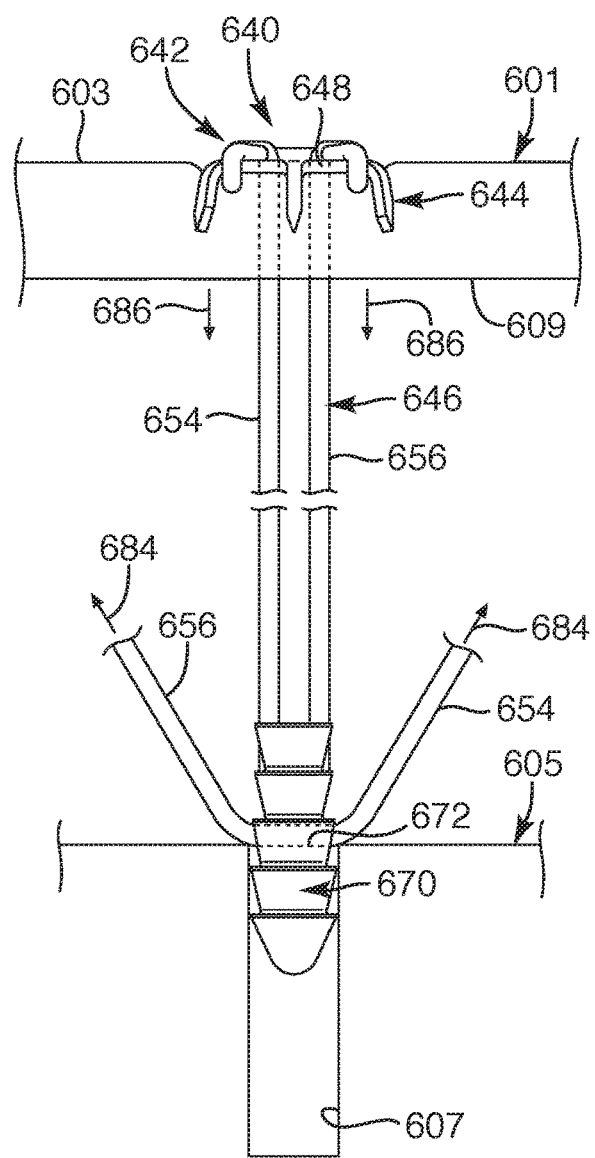
FIG. 44 is a side view of the repair device and the bone anchor with the flexible member extending therebetween, depicting the repair device fixated to soft tissue with the flexible member engaged with the bone anchor, according to another embodiment of the present invention.

With reference to FIGS. 42A and 43, the physician may then position a distal end 680 of the bone anchor 670 over a pre-drilled hole 607 in bone 605. The physician may then use an impacting device (not shown) to force the bone anchor 670 at least partially into the hole 607 defined in the bone 605, as depicted in FIG. 43. Further, the physician may then pull the first and second portions 654, 656 of flexible member 646 downward, as shown by arrow 682. As depicted in FIGS. 43 and 44, by drawing the first and second portions 654, 656 downward or away from an underside 609 of the soft tissue 601, the anchor member 642 may also be moved downward and pulled into so as to sink in the soft tissue 601. In this manner, the base 648 of the anchor member 642 may be positioned directly over an upper surface 603 of the soft tissue 601 and the legs 644 may be inserted and disposed within the soft tissue 601. Although the step of sinking the anchor member 642 into the soft tissue 601 is depicted as being after the bone anchor 670 is partially anchored in the bone 605, the anchor member 642 may be fixated to the soft tissue 601 prior to anchoring the bone anchor 670 in the bone 607.

Figure 45:
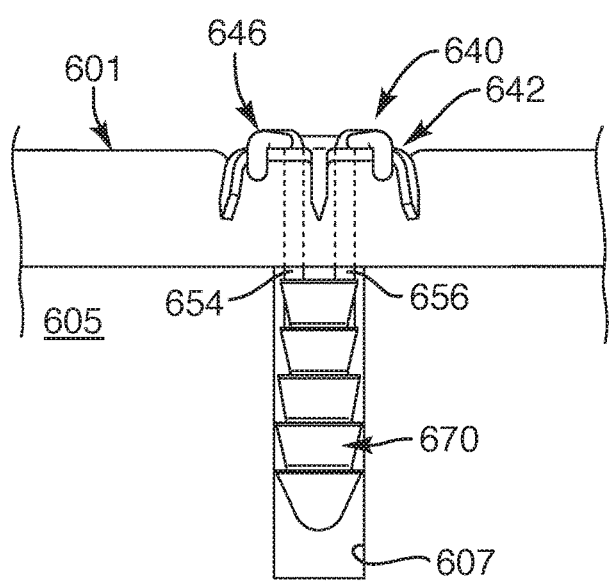
FIG. 45 is a side view of the repair device coupled to the bone anchor with the flexible member therebetween, depicting the soft tissue cinched against the bone with the repair device fixated to soft tissue and coupled in a knotless arrangement to the bone anchor with the flexible member, according to another embodiment of the present invention.

As depicted in FIGS. 44 and 45, upon at least partially inserting the bone anchor 670 into the pre-drilled hole 607 defined in the bone 605 and upon the anchor member 642 being fixated to the soft tissue 601, first and second portions 654, 656 of the flexible member 646 may be further pulled, as shown by arrows 684, to pull the first and second portions 654, 656 of the flexible member 646 from opposing ends of the laterally extending hole 672 of the bone anchor 670. By pulling such first and second portions 654, 656 of the flexible member 646, the anchor member 642 fixated to the soft tissue 601 may draw the soft tissue toward the bone anchor 670, as depicted by arrow 686, in a cinching manner. Once the soft tissue 601 is cinched against or adjacent a top surface of the bone anchor 670, the bone anchor 670 may be further forced into the bone 605 with a bone impacting instrument (not shown) so that the bone anchor 670 may be moved within the hole 607 in the bone 605 to a final or second anchored position therein, as depicted in FIG. 45. As the bone anchor 670 is forced into the hole 607, the position of the laterally extending hole 672 of the bone anchor 670 moves within the bone 605 so that the first and second portions 654, 656 of the flexible member 646 are pinched and anchored between the bone 605 and the bone anchor 670. The free end portions of the first and second portions 654, 656 of the flexible member 646 may be snipped and removed from the repair device 640 and tissue site. In this manner, the repair device 640 may be employed to fixate soft tissue 601 to bone 605 with the flexible member 646. Further, such flexible member 646 may be employed in a cinching arrangement and in a knotless manner to couple the repair device 640 to the bone anchor 670 with soft tissue 601 therebetween. With this arrangement, the flexible member 646 may be employed as a knotless coupling between the anchor member and the bone anchor, using any suitable knotless techniques as known to one of ordinary skill in the art. The soft tissue 601 fixated against the bone 607 may then undergo a healing process such that the soft tissue 601 eventually attaches itself to the bone 607. It should be further noted that the above-described method for fixating soft tissue to bone may be employed with any one of the repair devices described and depicted in FIGS. 28-31.

As set forth in previous embodiments, the anchor member of the repair device 450, 500, 530, 540, 550, 590 may be formed from metallic sheet material, such as stainless steel, titanium, or Nitinol, or any other suitable medical grade material or combinations of materials, so as to be laser cut from the sheet material or by employing any other suitable technique as known to one of ordinary skill in the art. In another embodiment, such repair device may be formed from a polymeric material or a bioresorbable material, formed and manufactured as known by one of ordinary skill in the art. Upon being cut from the sheet material, the legs of the repair devices 450, 500, 530, 540, 550, 590 may be bent to position the legs downward or moved to orient the legs to extend away from a single side or underside of the anchor member. Once the legs have been appropriately oriented and bent into position, the anchor member may undergo an electro polishing or chemical polishing process, as known to one of ordinary skill in the art. In this manner, the anchor members, set forth herein, may be a monolithic seamless structure formed as a single piece from sheet material. Further, the flexible member of the repair device 450, 500, 530, 540, 550, 590 may be formed from one or more filaments, such as a polymeric material or a natural fiber. In one embodiment, the flexible member may be formed from filaments or fibers made of a polyethylene material, such as ultra-high-molecular-weight polyethylene ("UHMWPE"), a polyester material, a polypropylene material, or the like. In another embodiment, the one or more filaments may be formed of a suture material. In still another embodiment, the polymeric filament or fiber may be a bioresorbable material, such as polylactide ("PLA"), polycaprolactone ("PCL"), polydioxanone ("PDX"), or the like, or any other suitable bioresorbable material as known to one of ordinary skill in the art. Such flexible member may be fixated to the anchor member of the repair device 450, 500, 530, 540, 550, 590 such that the one or more filaments may be formed in a woven or braided configuration or may extend with strands wound in a side-by-side configuration, or may extend with strands wound side-by-side and in a twisted configuration or any other suitable configuration to form the flexible member. In another embodiment, the flexible member may be a continuous loop. In another embodiment, the continuous loop may include a woven or braided structure. In another embodiment, the flexible member may extend with at least two free ends. In another embodiment, the flexible member may be formed from a suture or suture material. In another embodiment, the flexible member may be one or more sutures. In another embodiment, the one or more sutures may extend with two free ends.

The various repair device embodiments or other embodiments disclosed herein may be applied to any one of various soft tissue to soft tissue repairs as well as soft tissue to bone repairs. For example, the various repair device embodiments may be employed for flexor tendon repairs, patellar tendon repairs, Achilles tendon repairs, quadriceps tendon repairs, and/or bicep tendon repairs, or any other tendon, ligament, and tendon/ligament to bone repairs, such as kidner procedures or insertional Achilles repairs, or any other tendon/ligament to bone repairs. As such, the repair device may be appropriately sized for proper fixation to the different sized or types of soft tissue.

While the invention may be susceptible to various modifications and alternative forms, specific embodiments have been shown by way of example in the drawings and have been described in detail herein. Further, the structural features of any one embodiment disclosed herein may be combined or replaced by any one of the structural features of another embodiment set forth herein. As such, it should be understood that the invention is not intended to be limited to the particular forms disclosed. Rather, the invention includes employing any portion of one embodiment with another embodiment, all modifications, equivalents, and alternatives, falling within the spirit and scope of the invention as defined by the following appended claims.

What is claimed is:

1. A repair device for fixating to soft tissue at a soft tissue repair site, comprising:

an anchor member having a base with at least four legs extending from the base, the base extending with an upper side and an underside defining an outer periphery therebetween, the upper side of the base facing an opposite direction relative to the underside of the base, the upper side and underside defining an opening therein such that the base extends to define a ring like structure, the at least four legs each extend directly outward from the outer periphery and radially bend to extend downward in a maintained fixed orientation, the outer periphery defining a width between the upper side and the underside of the base, the width being less than an outer diameter of the ring like structure of the base; and one or more flexible filament members configured to be coupled to the base of the anchor member.

2. The repair device of claim 1, wherein at least one of the one or more flexible filament members is wrapped over the base so as to couple to the base and extend along the opening of the base.

3. The repair device of claim 1, wherein the one or more flexible filament members comprise one or more sutures with at least one of the one or more sutures extending downward from the base.

4. The repair device of claim 1, wherein the at least four legs comprise one or more barbs extending therefrom.

5. The repair device of claim 1, wherein the at least four legs extend downward from the base with an angled portion such that the angled portion extends at an angle that is less than seventy-five degrees relative to the underside of the anchor member.

6. The repair device of claim 1, wherein the at least four legs extend downward from the base with an angled portion such that the angled portion extends at an angle that is within the range of about twenty-five degrees and sixty-five degrees relative to the underside of the anchor member.

7. The repair device of claim 1, wherein the at least four legs extend radially from the outer periphery of the base and then extend straight downward at a right angle relative to the underside of the base.

8. A repair device for fixating to soft tissue at a soft tissue repair site, comprising:

an anchor member having a base with at least four legs extending from the base, the base extending with an outer radial surface extending between an upper surface and an underside surface with an opening extending through each of the upper surface and the underside surface so as to extend with a ring like structure, the upper surface of the base facing an opposite direction relative to the underside surface of the base, the outer radial surface defining a width between the upper surface and the underside surface of the base such that the width is less than an outer diameter of the ring like structure, the at least four legs extending directly from the outer radial surface of the base and extending downward with an elongated angled portion, the elongated angled portion being longitudinally oriented at an angle less than seventy-five degrees relative to the underside surface of the base; and one or more flexible filament members configured to be coupled to the base of the anchor member.

9. The repair device of claim 8, wherein at least one of the one or more flexible filament members is wrapped over the base so as to couple to the base and extend along the opening of the base.

10. The repair device of claim 8, wherein the one or more flexible filament members comprise one or more sutures.

11. The repair device of claim 8, wherein the one or more flexible filament members comprises a first flexible filament and a second flexible filament, the second flexible filament configured to be directly coupled to the first flexible filament.

12. The repair device of claim 8, wherein the angle of the elongated angled portion of the at least four legs extends within the range of about twenty-five degrees and sixty-five degrees relative to the underside of the anchor member.

13. The repair device of claim 8, wherein the at least four legs extends radially from an outer periphery of the base and then extends downward to the elongated angled portion.

14. The repair device of claim 8, wherein the at least four legs comprise one or more barbs extending therefrom.

15. The repair device of claim 8, wherein the at least four legs extend downward from the base in a maintained fixed orientation.

16. The repair device of claim 1, wherein the one or more flexible filament members comprises a first flexible filament and a second flexible filament, the second flexible filament configured to be directly coupled to the first flexible filament.

17. The repair device of claim 1, wherein the base extends with a flat circular profile defining a central axis, the central axis extending through the opening defined in the base.

18. The repair device of claim 8, wherein base extends with a flat circular profile defining a central axis, the central axis extending through the opening defined in the base.

* * * * *